United States Patent
Koestler et al.

(10) Patent No.: US 12,384,788 B2
(45) Date of Patent: *Aug. 12, 2025

(54) 1,4-DIHYDROBENZO[D]PYRAZOLO[3,4-F] [1,3]DIAZEPINE DERIVATIVES AND RELATED COMPOUNDS AS LRRK2, NUAK1 AND/OR TYK2 KINASE MODULATORS FOR THE TREATMENT OF E.G. AUTOIMMUNE DISEASE

(71) Applicant: Origenis GMBH, Martinsried (DE)

(72) Inventors: Roland Koestler, Martinsried (DE); Jean Tassel, Augsburg (DE); Michael Thormann, Planegg (DE); Nasser Yehia, Munich (DE); Andreas Treml, Bodenmais (DE); Michael Almstetter, Grasbrunn (DE)

(73) Assignee: Origenis GMBH, Martinsried (DE)

( * ) Notice: Subject to any disclaimer, the term of this patent is extended or adjusted under 35 U.S.C. 154(b) by 822 days.

This patent is subject to a terminal disclaimer.

(21) Appl. No.: 17/642,136

(22) PCT Filed: Sep. 11, 2020

(86) PCT No.: PCT/IB2020/000727
§ 371 (c)(1),
(2) Date: Mar. 10, 2022

(87) PCT Pub. No.: WO2021/048618
PCT Pub. Date: Mar. 18, 2021

(65) Prior Publication Data
US 2022/0380373 A1     Dec. 1, 2022

Related U.S. Application Data

(60) Provisional application No. 62/899,912, filed on Sep. 13, 2019.

(51) Int. Cl.
*A01N 43/00*     (2006.01)
*A01N 43/46*     (2006.01)
(Continued)

(52) U.S. Cl.
CPC .......... *C07D 487/04* (2013.01); *C07D 487/14* (2013.01)

(58) Field of Classification Search
None
See application file for complete search history.

(56) References Cited

U.S. PATENT DOCUMENTS

2014/0088117 A1   3/2014   Burch et al.

FOREIGN PATENT DOCUMENTS

| KR | 20190091534 A | 8/2019 |
|---|---|---|
| WO | 2012143143 A1 | 10/2012 |
| WO | 2013/164323 A1 | 11/2013 |

OTHER PUBLICATIONS

Bailey, 2005, Positron Emission Tomography: Basic Sciences, Secaucus, NJ: Springer-Verlag, ISBN 1-85233-798-2.
(Continued)

*Primary Examiner* — Layla Soroush
(74) *Attorney, Agent, or Firm* — Brown Rudnick LLP; Adam M. Schoen

(57) ABSTRACT

The present invention relates to compounds of formula (I) that are capable of modulating, e.g., inhibiting or activating, one or more kinases, especially LRRK2 and/or NUAK1 and/or TYK2 or mutants thereof. The compounds are useful for treating diseases, such as autoimmune diseases, inflammatory diseases, bone diseases, metabolic diseases, neurological and neurodegenerative diseases, cancer, cardiovascular diseases, allergies, asthma, Alzheimer's disease, Parkinson's disease, skin disorders, eye diseases, infectious diseases and hormone-related diseases. The present description discloses the synthesis and characterisation of exemplary compounds as well as pharmacological data thereof (e.g. pages 40 to 146; examples 1 to 63; compounds 1 to 248; tables 1 to 3). Preferred compounds are e.g. 1,4-dihydrobenzo[d]pyrazolo[3,4-f][1,3]diazepine derivatives and related compounds. An exemplary compound is e.g. 5-(2,6-difluorophenyl)-8-methoxy-1,4-dihydrobenzo[d]pyrazolo[3,4-f][1,3]diazepine (example 49). (Formula (II):

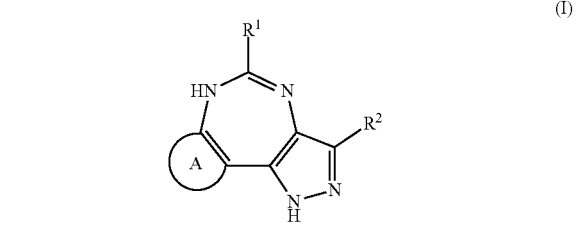

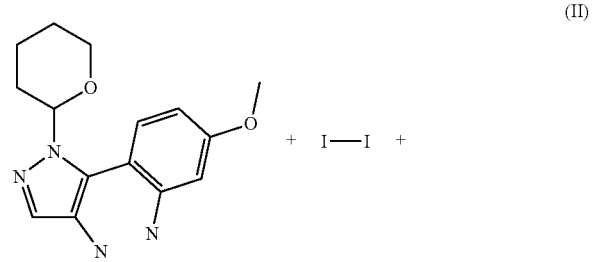

(Continued)

-continued

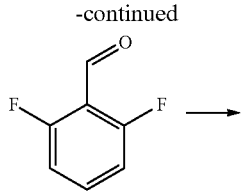

-continued

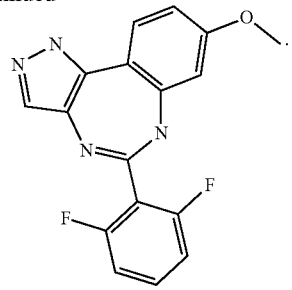

20 Claims, No Drawings

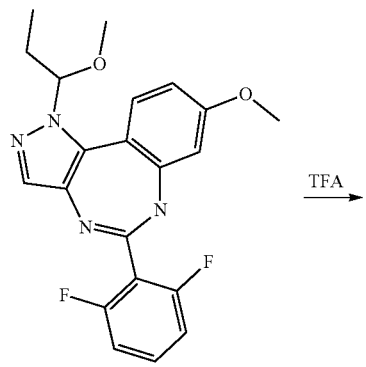

(51) Int. Cl.
   *A61K 31/55*   (2006.01)
   *C07D 487/04*  (2006.01)
   *C07D 487/14*  (2006.01)

(56) References Cited

OTHER PUBLICATIONS

Examination Report issued in Indian Application No. 202247020142, date of mailing: Sep. 23, 2022, 6 pages.
International Search Report and Written Opinion issued in International Application No. PCT/IB2020/000727, date of mailing: Nov. 5, 2020, 12 pages.
International Search Report and Written Opinion issued in International Application No. PCT/IB2020/000730, date of mailing: Nov. 5, 2020, 12 pages.

1,4-DIHYDROBENZO[D]PYRAZOLO[3,4-F][1,3]DIAZEPINE DERIVATIVES AND RELATED COMPOUNDS AS LRRK2, NUAK1 AND/OR TYK2 KINASE MODULATORS FOR THE TREATMENT OF E.G. AUTOIMMUNE DISEASE

CROSS-REFERENCE TO RELATED APPLICATIONS

This application is a national stage entry of PCT international application no. PCT/IB2020/000727, filed Sep. 11, 2020, which claims the benefit of, and priority to, U.S. Provisional Patent Application No. 62/899,912, filed Sep. 13, 2019, the contents of each of which are incorporated by reference.

FIELD OF THE INVENTION

The invention relates generally to compounds and their use in pharmacological composition for treatment of conditions as well as radio-labeled tracers in positron emission tomography (PET) for diagnostic uses.

BACKGROUND

A variety of medical conditions that affect millions of people are caused or exacerbated by unregulated activity of protein kinases. For example, aberrant kinase activity is associated with autoimmune diseases, inflammatory diseases, bone diseases, metabolic diseases, neurological and neurodegenerative diseases, cancer, cardiovascular diseases, allergies, asthma, Alzheimer's disease, Parkinson's disease, skin disorders, eye diseases, infectious diseases and hormone-related diseases. For many such disorders, however, no effective inhibitor or activator exists for the particular kinase that causes the disorder or its symptoms. Consequently, patients continue to suffer from an array of disorders due to the lack of a suitable drug for their conditions.

SUMMARY

The invention provides compounds that are useful in pharmacological composition for treatment of conditions as well as radio-labeled tracers in positron emission tomography (PET) for diagnostic uses. In certain embodiments, the compounds of the invention modulate, e.g., inhibit or activate, inhibit protein kinase activity, such as the activity of leucine-rich repeat kinase 2 (LRRK2), SNF1-like kinase 1 also known as AMPK-related protein kinase 5 (NUAK1) also known as (ARK5), and non-receptor tyrosine-protein kinase 2 (TYK2), that are associated with human diseases, disorders, and conditions. The compounds display improved pharmacological properties, such as tissue delivery, specificity, efficacy, and stability. For example, the invention includes compounds that are able to penetrate the blood-brain barrier and bind to kinase targets with high affinity. Additionally, radiolabeled forms of compounds of the invention are useful as PET tracers to identify anatomical locations of aberrant kinase activity.

Thus, compounds of the invention are useful as therapeutic and diagnostic agents for a wide variety of conditions, such as Parkinson's disease and autoimmune diseases.

Accordingly, the invention provides compositions containing compounds described herein, including pharmacological compositions and compositions for diagnostic applications.

The invention further provides methods of using such compositions to diagnose and/or treat a disorder in a subject.

In an aspect, the invention provides compounds of formula (I):

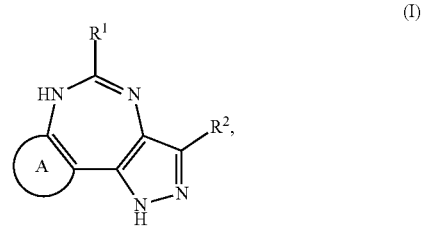

(I)

or a tautomer thereof, or a pharmaceutically acceptable salt thereof,
wherein:
$R^1$ is aryl or heteroaryl;
$R^2$ is H, halo, OH, CN, $CF_3$, $C_{1-6}$ alkyl, $C_{1-6}$ alkoxy, $C_{1-6}$ haloalkyl, $C_{1-6}$ thioalkyl, $C_{3-8}$ cycloalkyl, $C_{2-8}$ heterocycloalkyl, aryl, or heteroaryl; and
A is aryl or 5- or 6-membered heteroaryl;
wherein each of the $C_{1-6}$ alkyl, $C_{1-6}$ alkoxy, $C_{1-6}$ haloalkyl, $C_{1-6}$ thioalkyl, $C_{3-8}$ cycloalkyl, $C_{2-8}$ heterocycloalkyl, aryl, and heteroaryl is optionally substituted with one or more moieties selected from the group consisting of halo, OH, CN, $CF_3$, $NH_2$, $NO_2$, $C_{1-6}$ alkyl, $C_{1-6}$ haloalkyl, $C_{1-6}$ thioalkyl, $C_{3-8}$ cycloalkyl, $C_{2-8}$ heterocycloalkyl, $C_{2-8}$ heterocycloalkenyl, $C_{2-6}$ alkenyl, $C_{2-6}$ alkynyl, $C_{1-6}$ alkoxy, $C_{1-6}$ haloalkoxy, $C_{1-6}$ alkylamino, $C_{2-6}$ dialkylamino, $C_{7-12}$ aralkyl, $C_{1-12}$ heteroaralkyl, aryl, heteroaryl, —C(O)R, —C(O)OR, —C(O)NRR', —C(O)NRS(O)$_2$R', —C(O)NRS(O)$_2$NR'R", —OR, —OC(O)NRR', —NRR', —NRC(O)R', —NRC(O)NR'R", —NRS(O)$_2$R', —NRS(O)$_2$NR'R", —S(O)$_2$R, and —S(O)$_2$NRR', in which each of R, R', and R", independently, is H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, aryl, or heteroaryl, or R and R', or R' and R", together with the nitrogen to which they are attached, form $C_{2-8}$ heterocycloalkyl.

The compound of formula (I) may be represented by formula (II):

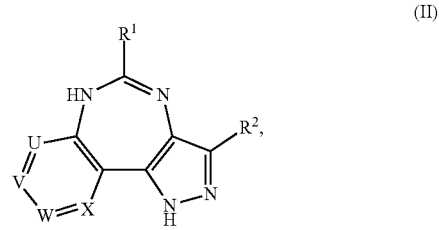

(II)

wherein
$R^1$ is aryl or heteroaryl;
$R^2$ is H, halo, OH, CN, $CF_3$, $C_{1-6}$ alkyl, $C_{1-6}$ alkoxy, $C_{1-6}$ haloalkyl, $C_{1-6}$ thioalkyl, or $C_{3-8}$ cycloalkyl;
U is N or $CR^3$;
V is N or $CR^4$;
W is N or $CR^5$;
X is N or $CR^6$; and
each of $R^3$—$R^6$, independently, is H, halo, OH, CN, $CF_3$, $CHF_2$, $CH_2F$, $NH_2$, $NO_2$, $C_{1-6}$ alkyl, $C_{1-6}$ haloalkyl, $C_{2-6}$ alkenyl, $C_{3-8}$ cycloalkyl, $C_{2-8}$ heterocycloalkyl, $C_{2-8}$ heterocycloalkenyl, aryl, heteroaryl, —C(O)R, —C(O)OR, —C(O)NRR', —C(O)NRS(O)$_2$R', —C(O)NRS(O)$_2$NR'R", —OR, —OC(O)NRR', —NRR', —NRC(O)R', —NRC(O)NR'R", —NRS(O)$_2$R', —NRS(O)$_2$NR'R", —S(O)$_2$R, or —S(O)$_2$NRR', wherein each of R, R', and R", independently, is H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, aryl, or heteroaryl, or R and R', or R' and R", together with the nitrogen to which they are attached, form $C_{2-8}$ heterocycloalkyl; and at most one N is assigned to U, V, W, and X.

One of U, V, W, and X may be N.

U may be N. V may be $CR^4$, W may be $CR^5$, and X may be $CR^6$, in which each of $R^4$, $R^5$, and $R^6$ is H. V may be $CR^4$, W may be $CR^5$, and X may be $CR^6$, $R^6$ being H and each of $R^4$ and $R^5$, independently, being F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR', in which each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl. V may be $CR^4$, W may be $CR^5$, and X may be $CR^6$, each of $R^4$ and $R^6$ being H and $R^5$ being F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR', in which each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

V may be N. U may be $CR^3$, W may be $CR^5$, and X may be $CR^6$, in which each of $R^3$, $R^5$, and $R^6$ is H. U may be $CR^3$, W may be $CR^5$, and X may be $CR^6$, $R^6$ being H and each of $R^3$ and $R^5$, independently, being F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR', in which each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl. U may be $CR^3$, W may be $CR^5$, and X may be $CR^6$, each of $R^3$ and $R^6$ being H and $R^5$ being F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR', in which each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

U may be N, V may be $CR^4$, W may be $CR^5$, and X may be $CR^6$, $R^6$ being H and each of $R^4$ and $R^5$, independently, being F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR', wherein each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

U may be $CR^3$, V may be N, W may be $CR^5$, and X may be $CR^6$, $R^6$ being H and each of $R^3$ and $R^5$, independently, being F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR', wherein each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

U may be N, V may be $CR^4$, W may be $CR^5$, and X may be $CR^6$, each of $R^4$ and $R^6$ being H and $R^5$ being F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR'; wherein each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

U may be $CR^3$, V may be N, W may be $CR^5$, and X may be $CR^6$, each of $R^3$ and $R^6$ being H and $R^5$ being F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR', wherein each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

$R^1$ may be aryl. $R^1$ may be

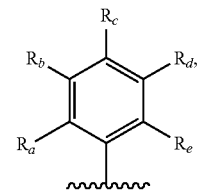

wherein each of $R_a$—$R_e$, independently, is H, halo, OH, CN, $CF_3$, $CHF_2$, $CH_2F$, $NH_2$, $NO_2$, $C_{1-6}$ alkyl, $C_{1-6}$ haloalkyl, $C_{2-6}$ alkenyl, $C_{3-8}$ cycloalkyl, $C_{2-8}$ heterocycloalkyl, $C_{2-8}$ heterocycloalkenyl, aryl, heteroaryl, —C(O)R, —C(O)OR, —C(O)NRR', —C(O)NRS(O)$_2$R', —C(O)NRS(O)$_2$NR'R", —OR, —OC(O)NRR', —NRR', —NRC(O)R', —NRC(O)NR'R", —NRS(O)$_2$R', —NRS(O)$_2$NR'R", —S(O)$_2$R, or —S(O)$_2$NRR', wherein each of R, R', and R", independently, is H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, aryl, or heteroaryl, or R and R', or R' and R", together with the nitrogen to which they are attached, form $C_{2-8}$ heterocycloalkyl.

At least two of $R_b$, $R_c$, and $R_d$ may each be H. Each of $R_b$, $R_c$, and $R_d$ may be H. Each of $R_a$ and $R_e$, may independently be halo or $C_{1-6}$ alkyl. Each of $R_a$ and $R_e$ may be halo. Each of $R_a$ and $R_e$ may be F or Cl. Each of $R_a$ and $R_e$ may be F, and each of $R_b$, $R_c$, and $R_d$ may be H. Each of $R_a$ and $R_e$ may be Cl, and each of $R_b$, $R_c$, and $R_d$ may be H.

$R^1$ may be a 5- or 6-membered heteroaryl. $R^1$ may be a 5-membered heteroaryl. $R^1$ may be a 5-membered heteroaryl containing at least one N. $R^1$ may be a 5-membered heteroaryl selected from the group consisting of pyrrolyl, pyrazolyl, indolyl, indazolyl, and azaindazolyl. $R^1$ may be a 5-membered heteroaryl containing O or S. $R^1$ may be a 5-membered heteroaryl selected from the group consisting of furanyl, thienyl, benzofuranyl, and benzothienyl. $R^1$ may be a 6-membered heteroaryl containing at least one N. $R^1$ may be an optionally substituted pyridine.

$R^2$ may be H, halo, $C_{1-6}$ alkyl, $C_{1-6}$ alkoxy, $C_{1-6}$ thioalkyl, or $C_{3-8}$ cycloalkyl. $R^2$ may be H, halo, —$CH_3$, —$SCH_3$, or cyclopropyl. $R^2$ may be H, Cl, —$CH_3$, or —$SCH_3$.

The compound of formula (I) may be represented by formula (III):

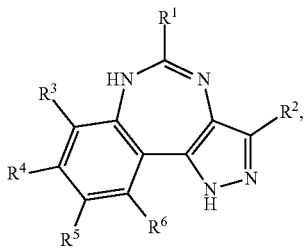

(III)

wherein

R¹ is aryl or heteroaryl;

R² is H, halo, OH, CN, CF₃, $C_{1-6}$ alkyl, $C_{1-6}$ alkoxy, $C_{1-6}$ haloalkyl, $C_{1-6}$ thioalkyl, or $C_{3-8}$ cycloalkyl; and each of R³—R⁶, independently, is H, halo, OH, CN, CF₃, CHF₂, CH₂F, NH₂, NO₂, $C_{1-6}$ alkyl, $C_{1-6}$ haloalkyl, $C_{2-6}$ alkenyl, $C_{3-8}$ cycloalkyl, $C_{2-8}$ heterocycloalkyl, $C_{2-8}$ heterocycloalkenyl, aryl, heteroaryl, —C(O)R, —C(O)OR, —C(O)NRR', —C(O)NRS(O)₂R', —C(O)NRS(O)₂NR'R'', —OR, —OC(O)NRR', —NRR', —NRC(O)R', —NRC(O)NR'R'', —NRS(O)₂R', —NRS(O)₂NR'R'', —S(O)₂R, or —S(O)₂NRR', or R⁴ and R⁵, together with atoms to which they are attached form a ring having between 5 and 10 members, wherein each of R, R', and R'', independently, is H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, aryl, or heteroaryl, or R and R', or R' and R'', together with the nitrogen to which they are attached, form $C_{2-8}$ heterocycloalkyl.

Each of R³—R⁶ may independently be H, halo, OH, CN, CF₃, NH₂, NO₂, $C_{1-6}$ alkyl, $C_{3-8}$ cycloalkyl, $C_{2-8}$ heterocycloalkyl, $C_{2-8}$ heterocycloalkenyl, aryl, heteroaryl, —C(O)OR, —C(O)NRR', —OR, —OC(O)NRR', —NRR', or —NRC(O)R'. At least three of R³—R⁶ may be H. Each of R³, R⁴, and R⁶ may be H. All of R³—R⁶ may be H. Each R³ and R⁶ is H, and each of R⁴ and R⁵ may independently be halo, OH, CN, CF₃, NH₂, NO₂, $C_{1-6}$ alkyl, $C_{3-8}$ cycloalkyl, $C_{2-8}$ heterocycloalkyl, $C_{2-8}$ heterocycloalkenyl, aryl, heteroaryl, —C(O)OR, —C(O)NRR', —OR, —OC(O)NRR', —NRR', or —NRC(O)R'. Each of R³, R⁴, and R⁶ may be H, and R⁵ may be halo, OH, CN, CF₃, NH₂, NO₂, $C_{1-6}$ alkyl, $C_{3-8}$ cycloalkyl, $C_{2-8}$ heterocycloalkyl, $C_{2-8}$ heterocycloalkenyl, aryl, heteroaryl, —C(O)OR, —C(O)NRR', —OR, —OC(O)NRR', —NRR', or —NRC(O)R'. Each of R³—R⁶ may independently be H, halo, CF₃, $C_{1-6}$ alkyl, $C_{2-8}$ heterocycloalkyl, $C_{2-8}$ heterocycloalkenyl, —OR, —C(O)OR, or —C(O)NRR'. Each of R³ and R⁶ may be H, and each of R⁴ and R⁵ may independently be halo, CF₃, $C_{1-6}$ alkyl, $C_{2-8}$ heterocycloalkyl, $C_{2-8}$ heterocycloalkenyl, —OR, —C(O)OR, or —C(O)NRR'. Each of R⁴ and R⁵ may independently be F, Cl, CF₃, $C_{1-6}$ alkyl, $C_{2-8}$ heterocycloalkyl, $C_{2-8}$ heterocycloalkenyl, —OR, —C(O)OR, or —C(O)NRR', in which each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl. Each of R³, R⁴, and R⁶ may be H, and R⁵ may be halo, CF₃, $C_{1-6}$ alkyl, $C_{2-8}$ heterocycloalkyl, $C_{2-8}$ heterocycloalkenyl, —OR, —C(O)OR, or —C(O)NRR'. R⁵ may be F, Cl, CF₃, $C_{1-6}$ alkyl, $C_{2-8}$ heterocycloalkyl, $C_{2-8}$ heterocycloalkenyl, —OR, —C(O)OR, or —C(O)NRR', in which each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

The compound of formula (I) may be represented by formula (III):

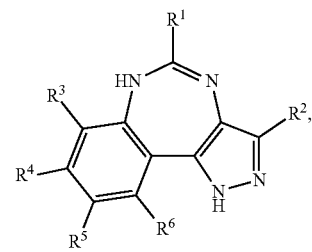

(III)

wherein:

R¹ represents

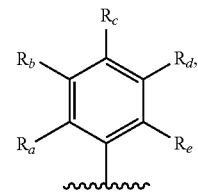

wherein:

each of $R_a$, $R_b$, $R_c$, $R_d$, and $R_e$ is H, Br, F, or Cl;

R² is H, Cl, —CH₃, or —SCH₃; and each of R³ and R⁶ is H, and each of R⁴ and R⁵, independently, is halo, OH, CN, CF₃, CHF₂, CH₂F, NH₂, NO₂, $C_{1-6}$ alkyl, $C_{3-8}$ cycloalkyl, $C_{2-8}$ heterocycloalkyl, $C_{2-8}$ heterocycloalkenyl, aryl, heteroaryl, —C(O)OR, —C(O)NRR', —OR, —OC(O)NRR', —NRR', or —NRC(O)R', or R⁴ and R⁵, together with atoms to which they are attached form a ring having between 5 and 10 members, in which each of R, R', and R'', independently, is H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, aryl, or heteroaryl, or R and R', or R' and R'', together with the nitrogen to which they are attached, form $C_{2-8}$ heterocycloalkyl.

The compound of formula (I) may be represented by formula (II):

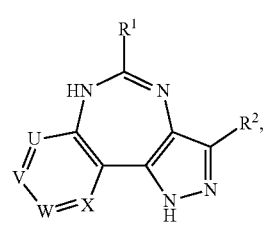

(II)

wherein:
R¹ represents

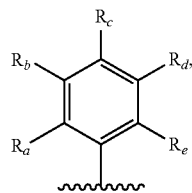

wherein:
each of $R_a$, $R_b$, $R_c$, $R_d$, and $R_e$ is H, Br, F, or Cl;
R² is H, Cl, —CH₃, or —SCH₃; and
U is N, V is CR⁴, W is CR⁵, and X is CR⁶, each of R⁴ and R⁶ being H and R⁵ being F, Cl, CF₃, CHF₂, CH₂F, C₁₋₆ alkyl, C₂₋₈ heterocycloalkyl, C₂₋₈ heterocycloalkenyl, —OR, —C(O)OR, or —C(O)NRR', in which each of R, R', and R", independently, is H, halo, OH, C₁₋₆ alkyl, C₁₋₆ haloalkyl, C₁₋₆ alkoxy, C₃₋₈ cycloalkyl, C₂₋₈ heterocycloalkyl, aryl, or heteroaryl, or R and R', or R' and R", together with the nitrogen to which they are attached, form C₂₋₈ heterocycloalkyl.

A may be a 5-membered heteroaryl containing at least one N. A may be a 5-membered heteroaryl selected from the group consisting of pyrazolyl, indazolyl, and azaindazolyl.

In another aspect, the invention provides pharmaceutical compositions that contain a compound, such as any of those described above, or a pharmaceutically acceptable salt of such a compound and a pharmaceutically acceptable carrier.

In another aspect, the invention provides a compound, such as any of those described above, for use in the manufacture of a medicament for treating a medical condition characterized by aberrant activity or expression of a kinase. The kinase may be overexpressed of underexpressed. The kinase may have increased activity or decreased activity. The kinase may be LRRK2, NUAK1, or TYK2.

In another aspect, the invention provides methods of modulating a kinase by contacting cells containing the kinase with a compound, such as any of those described above, or a pharmaceutically acceptable salt of such a compound. The method may include inhibiting a kinase. The method may include activating a kinase. The kinase may be LRRK2, NUAK1, or TYK2.

In another aspect, the invention provides methods of treating a medical condition characterized by overexpression of a kinase by administering to a subject in need thereof an effective amount of a compound, such as any of those described above, or a pharmaceutically acceptable salt of such a compound. The kinase may be LRRK2, NUAK1, or TYK2. The condition may be an autoimmune disease, inflammatory disease, bone disease, metabolic disease, neurological or neurodegenerative disease, cancer, cardiovascular disease, allergies, asthma, Alzheimer's disease, Parkinson's disease, skin disorder, eye disease, infectious disease, or hormone-related disease.

In another aspect, the invention provides methods of preparing compounds, such as any of those described above, by reacting a bis-amino compound with an aldehyde to form the compound.

DETAILED DESCRIPTION

Chemical Definitions

The expression cycloalkyl refers to a saturated or partially unsaturated (for example, a cycloalkenyl group) cyclic group that contains one or more rings and contains from 3 to 14 ring carbon atoms, such as from 3 to 10 (e.g., 3, 4, 5, 6 or 7) ring carbon atoms. The expression cycloalkyl refers furthermore to groups in which one or more hydrogen atoms have been replaced by fluorine, chlorine, bromine or iodine atoms or by OH, =O, SH, =S, NH₂, =NH, N₃ or NO₂ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbomyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group.

The expression heterocycloalkyl refers to a cycloalkyl group as defined above in which one or more (e.g., 1, 2 or 3) ring carbon atoms have been replaced by an oxygen, nitrogen, silicon, selenium, phosphorus or sulfur atom or a SO group or a SO₂ group. A heterocycloalkyl group has preferably 1 or 2 rings containing from 3 to 10 (e.g., 3, 4, 5, 6 or 7) ring atoms (e.g., C, O, N or S). The expression heterocycloalkyl refers furthermore to groups that are substituted by fluorine, chlorine, bromine or iodine atoms or by OH, =O, SH, =S, NH₂, =NH, N₃ or NO₂ groups. Examples are a piperidyl, prolinyl, imidazolidinyl, piperazinyl, morpholinyl, urotro pinyl, pyrrolidinyl, tetrahydrothiophenyl, tetrahydropyranyl, tetrahydrofuryl or 2-pyrazolinyl group and also lactams, lactones, cyclic imides and cyclic anhydrides.

The expression alkylcycloalkyl refers to groups that contain both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two rings having from 3 to 10 (e.g., 3, 4, 5, 6 or 7) ring carbon atoms, and one or two alkyl, alkenyl or alkynyl groups having 1 or 2 to 6 carbon atoms.

The expression heteroalkylcycloalkyl refers to alkylcycloalkyl groups as defined above in which one or more (e.g., 1, 2 or 3) carbon atoms have been replaced by an oxygen, nitrogen, silicon, selenium, phosphorus or sulfur atom or a SO group or a SO₂ group. A heteroalkylcycloalkyl group preferably contains 1 or 2 rings having from 3 to 10 (e.g., 3, 4, 5, 6 or 7) ring atoms, and one or two alkyl, alkenyl, alkynyl or heteroalkyl groups having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being saturated or mono-, di- or tri-unsaturated.

The expression aryl refers to an aromatic group that contains one or more rings containing from 6 to 14 ring carbon atoms, such as from 6 to 10 ring carbon atoms. The expression aryl refers furthermore to groups that are substituted by fluorine, chlorine, bromine or iodine atoms or by OH, SH, NH₂, N₃ or NO₂ groups. Examples are the phenyl, naphthyl, biphenyl, 2-fluorophenyl, anilinyl, 3-nitrophenyl or 4-hydroxyphenyl group.

The expression heteroaryl refers to an aromatic group that contains one or more rings containing from 5 to 14 ring atoms, such as from 5 to 10 ring atoms, and contains one or more (e.g., 1, 2, 3 or 4) oxygen, nitrogen, phosphorus or sulfur ring atoms. The expression heteroaryl refers furthermore to groups that are substituted by fluorine, chlorine, bromine or iodine atoms or by OH, SH, N₃, NH₂ or NO₂ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The expression aralkyl refers to groups containing both aryl and also alkyl, alkenyl, alkynyl and/or cycloalkyl groups in accordance with the above definitions, such as, for example, aryl-alkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic ring systems containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to an aralkyl group as defined above in which one or more (e.g., 1, 2, 3 or 4) carbon atoms have been replaced by an oxygen, nitrogen, silicon, selenium, phosphorus, boron or sulfur atom, that is to say to groups containing both aryl or heteroaryl, respectively, and also alkyl, alkenyl, alkynyl and/or heteroalkyl and/or cycloalkyl and/or heterocycloalkyl groups in accordance with the above definitions. A heteroaralkyl group preferably contains one or two aromatic ring systems containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, wherein 1, 2, 3 or 4 of these carbon atoms have been replaced by oxygen, sulfur or nitrogen atoms.

Examples are arylheteroalkyl, arylheterocycloalkyl, arylheterocycloalkenyl, arylalkyl heterocycloalkyl, arylalkenylheterocycloalkyl, arylalkynylheterocycloalkyl, arylalkylhetero cycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, hetero arylheterocycloalkenyl, heteroarylalkylcycloalkyl, heteroarylalkylheterocycloalkenyl, hetero arylheteroalkylcycloalkyl, heteroarylheteroalkylcycloalkenyl and heteroarylheteroalkylhetero cycloalkyl groups, the cyclic groups being saturated or mono-, di- or tri-unsaturated. Specific examples are a tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

As stated above, the expressions cycloalkyl, heterocycloalkyl, alkylcycloalkyl, heteroalkylcycloalkyl, aryl, heteroaryl, aralkyl and heteroaralkyl also refer to groups that are substituted by fluorine, chlorine, bromine or iodine atoms or by OH, =O, SH, =S, $NH_2$, =NH, $N_3$ or $NO_2$ groups.

The expression "optionally substituted" especially refers to groups that are optionally substituted by fluorine, chlorine, bromine or iodine atoms or by OH, =O, SH, =S, $NH_2$, =NH, $N_3$ or $NO_2$ groups. This expression refers furthermore to groups that may be substituted by one, two, three or more unsubstituted $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{16}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{18}$ aryl, $C_{1-17}$ heteroaryl, $C_7$-$C_{20}$ aralkyl or $C_2$-$C_{19}$ heteroaralkyl groups. This expression refers furthermore to groups that may be substituted by one, two, three or more unsubstituted $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl or $C_2$-$C_{11}$ heteroaralkyl groups.

Exemplary substituents are F, Cl, Br, OH, SH, =O, $NH_2$, $C_{1-4}$ alkyl, $C_{1-4}$ heteroalkyl cyclopropyl, $SF_5$, NO and $NO_2$.

Other exemplary substituents are F, Cl, Br, OH, SH, =O, $NH_2$, $C_{1-4}$ alkyl (e.g. methyl, ethyl, t-butyl), $NMe_2$, $CONH_2$, $CH_2NMe_2$, $NHSO_2Me$, $C(CH_3)_2CN$, COMe, OMe, SMe, COOMe, COOEt, $CH_2COOH$, $OCH_2COOH$, COOH, SOMe, $SO_2Me$, cyclopropyl, $SO_2NH_2$, $SO_2NHMe$, $SO_2CH_2CH_2OH$, $NHCH_2CH_2OH$, $CH_2CH_2OCH_3$, $SF_5$, $SO_2NMe_2$, NO, $NO_2$, $OCF_3$, $SO_2CF_3$, CN or $CF_3$.

Other exemplary substituents are F, Cl, Br, Me, OMe, CN or $CF_3$.

The term halogen preferably refers to F, Cl, Br or I.

According to certain embodiments, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may optionally be substituted.

When an aryl, heteroaryl, cycloalkyl, alkylcycloalkyl, heteroalkylcycloalkyl, heterocycloalkyl, aralkyl or heteroaralkyl group contains more than one ring, these rings may be bonded to each other via a single or double bond or these rings may be annulated.

Compounds

In an aspect, the invention provides compounds of formula (I):

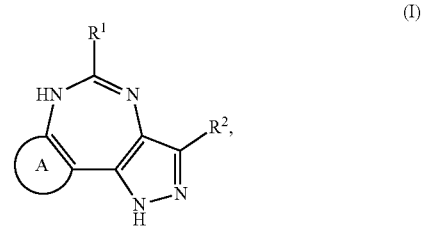

(I)

or a tautomer thereof, or a pharmaceutically acceptable salt thereof, wherein:

$R^1$ is aryl or heteroaryl;

$R^2$ is H, halo, OH, CN, $CF_3$, $C_{1-6}$ alkyl, $C_{1-6}$ alkoxy, $C_{1-6}$ haloalkyl, $C_{1-6}$ thioalkyl, $C_{3-8}$ cycloalkyl, $C_{2-8}$ heterocycloalkyl, aryl, or heteroaryl; and A is aryl or 5- or 6-membered heteroaryl;

wherein each of the $C_{1-6}$ alkyl, $C_{1-6}$ alkoxy, $C_{1-6}$ haloalkyl, $C_{1-6}$ thioalkyl, $C_{3-8}$ cycloalkyl, $C_{2-8}$ heterocycloalkyl, aryl, and heteroaryl is optionally substituted with one or more moieties selected from the group consisting of halo, OH, CN, $CF_3$, $NH_2$, $NO_2$, $C_{1-6}$ alkyl, $C_{1-6}$ haloalkyl, $C_{1-6}$ thioalkyl, $C_{3-8}$ cycloalkyl, $C_{2-8}$ heterocycloalkyl, $C_{2-8}$ heterocycloalkenyl, $C_{2-6}$ alkenyl, $C_{2-6}$ alkynyl, $C_{1-6}$ alkoxy, $C_{1-6}$ haloalkoxy, $C_{1-6}$ alkylamino, $C_{2-6}$ dialkylamino, $C_{7-12}$ aralkyl, $C_{1-12}$ heteroaralkyl, aryl, heteroaryl, —C(O)R, —C(O)OR, —C(O)NRR', —C(O)NRS(O)$_2$R', —C(O)NRS(O)$_2$NR'R", —OR, —OC(O)NRR', —NRR', —NRC(O)R', —NRC(O)NR'R", —NRS(O)$_2$R', —NRS(O)$_2$NR'R", —S(O)$_2$R, and —S(O)$_2$NRR', in which each of R, R', and R", independently, is H, halo, OH, $C_{1-6}$ alkyl, $C_{1-6}$ haloalkyl, $C_{1-6}$ alkoxy, $C_{3-8}$ cycloalkyl, C$_{2-8}$ heterocycloalkyl, aryl, or heteroaryl, or R and R', or R' and R", together with the nitrogen to which they are attached, form C$_{2-8}$ heterocycloalkyl.

R$^1$ may be a group of formula X$^1$-L$^1$-Y$^1$ or a group of formula X$^1$-L$^1$-Y$^1$-LA-Z$^1$ wherein X$^1$ is an optionally substituted phenyl group or an optionally substituted heteroaryl group containing 5 or 6 ring atoms and 1, 2, 3 or 4 heteroatoms selected from O, S and N; L$^1$ is a bond or a group of formula —CH$_2$—, —C(=O)—, —SO—, —SO$_2$—, —NH—C(=O)—, —C(=O)—NH—; —C(=O)—O—, —O—C(=O)—, —NH—C(=O)—O—, —O—C(=O)—NH—, —NH—SO$_2$—NH—, —CH$_2$—NH—CH$_2$—, —NH SO$_2$—, —SO$_2$—NH— or —NH—C(=O)—NH—;

Y$^1$ is an optionally substituted phenyl group, an optionally substituted heteroaryl group containing 5 or 6 ring atoms and 1, 2, 3 or 4 heteroatoms selected from O, S and N, an optionally substituted C$_3$-C$_7$ cycloalkyl group or an optionally substituted heterocycloalkyl group containing 3, 4, 5, 6 or 7 ring atoms and 1, 2, 3 or 4 heteroatoms selected from O, S and N; L$^2$ is a bond or a group of formula —CH$_2$—, —C(=O)—, —SO—, —SO$_2$—, —NH—C(=O)—, —C(=O)—NH—; —C(=O)—O—, —O—C(=O)—, —NH—C(=O)—O—, —O—C(=O)—NH—, —NH—SO$_2$—NH—, —CH$_2$—NH—CH$_2$—, —NH SO$_2$—, —SO$_2$—NH— or —NH—C(=O)—NH—; and Z$^1$ is an optionally substituted phenyl group, an optionally substituted heteroaryl group containing 5 or 6 ring atoms and 1, 2, 3 or 4 heteroatoms selected from O, S and N, an optionally substituted C$_3$-C$_7$ cycloalkyl group or an optionally substituted heterocycloalkyl group containing 3, 4, 5, 6 or 7 ring atoms and 1, 2, 3 or 4 heteroatoms selected from O, S and N.

R$^1$ may be selected from the following groups:

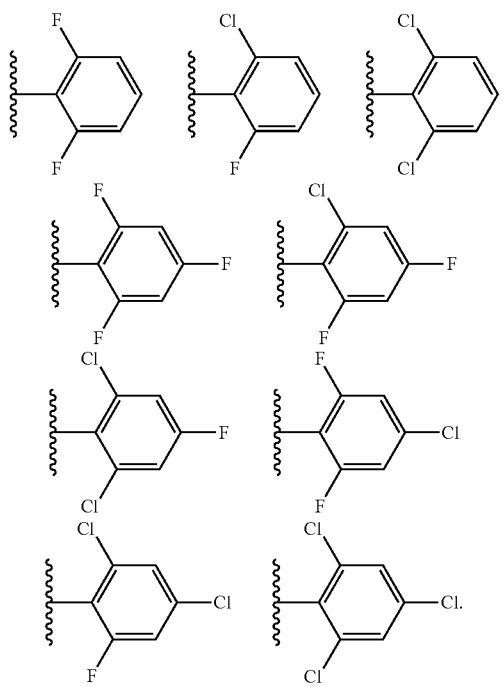

The compound of formula (I) may be represented by formula (II):

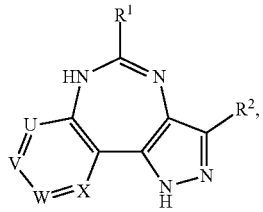

wherein
R$^1$ is aryl or heteroaryl;
R$^2$ is H, halo, OH, CN, CF$_3$, C$_{1-6}$ alkyl, C$_{1-6}$ alkoxy, C$_{1-6}$ haloalkyl, C$_{1-6}$ thioalkyl, or C$_{3-8}$ cycloalkyl;
U is N or CR$^3$;
V is N or CR$^4$;
W is N or CR$^5$;
X is N or CR$^6$; and
each of R$^3$—R$^6$, independently, is H, halo, OH, CN, CF$_3$, CHF$_2$, CH$_2$F, NH$_2$, NO$_2$, C$_{1-6}$ alkyl, C$_{1-6}$ haloalkyl, C$_{2-6}$ alkenyl, C$_{3-8}$ cycloalkyl, C$_{2-8}$ heterocycloalkyl, C$_{2-8}$ heterocycloalkenyl, aryl, heteroaryl, —C(O)R, —C(O)OR, —C(O)NRR', —C(O)NRS(O)$_2$R', —C(O)NRS(O)$_2$NR'R", —OR, OC(O)NRR', —NRR', —NRC(O)R', —NRC(O)NR'R", —NRS(O)$_2$R', —NRS(O)$_2$NR'R", —S(O)$_2$R, or —S(O)$_2$NRR',
wherein
each of R, R', and R", independently, is H, halo, OH, C$_{1-6}$ alkyl, C$_{1-6}$ haloalkyl, C$_{1-6}$ alkoxy, C$_{3-8}$ cycloalkyl, C$_{2-8}$ heterocycloalkyl, aryl, or heteroaryl, or
R and R', or R' and R", together with the nitrogen to which they are attached, form C$_{2-8}$ heterocycloalkyl; and
at most one N is assigned to U, V, W, and X.
One of U, V, W, and X may be N.
U may be N. V may be CR$^4$, W may be CR$^5$, and X may be CR$^6$, in which each of R$^4$, R$^5$, and R$^6$ is H. V may be CR$^4$, W may be CR$^5$, and X may be CR$^6$, R$^6$ being H and each of R$^4$ and R$^5$, independently, being F, Cl, CF$_3$, C$_{1-6}$ alkyl, C$_{2-8}$ heterocycloalkyl, C$_{2-8}$ heterocycloalkenyl, —OR, —C(O) OR, or —C(O)NRR', in which each of R and R', independently, is H, C$_{1-6}$ alkyl, C$_{1-6}$ haloalkyl, C$_{3-8}$ cycloalkyl, or C$_{2-8}$ heterocycloalkyl, or R and R', together with the nitrogen to which they are attached, form C$_{2-8}$ heterocycloalkyl. V may be CR$^4$, W may be CR$^5$, and X may be CR$^6$, each of R$^4$ and R$^6$ being H and R$^5$ being F, Cl, CF$_3$, C$_{1-6}$ alkyl, C$_{2-8}$ heterocycloalkyl, C$_{2-8}$ heterocycloalkenyl, —OR, —C(O) OR, or —C(O)NRR', in which each of R and R', independently, is H, C$_{1-6}$ alkyl, C$_{1-6}$ haloalkyl, C$_{3-8}$ cycloalkyl, or C$_{2-8}$ heterocycloalkyl, or R and R', together with the nitrogen to which they are attached, form C$_{2-8}$ heterocycloalkyl.
V may be N. U may be CR$^3$, W may be CR$^5$, and X may be CR$^6$, in which each of R$^3$, R$^5$, and R$^6$ is H. U may be CR$^3$, W may be CR$^5$, and X may be CR$^6$, R$^6$ being H and each of R$^3$ and R$^5$, independently, being F, Cl, CF$_3$, C$_{1-6}$ alkyl, C$_{2-8}$ heterocycloalkyl, C$_{2-8}$ heterocycloalkenyl, —OR, —C(O) OR, or —C(O)NRR', in which each of R and R', independently, is H, C$_{1-6}$ alkyl, C$_{1-6}$ haloalkyl, C$_{3-8}$ cycloalkyl, or C$_{2-8}$ heterocycloalkyl, or R and R', together with the nitrogen to which they are attached, form C$_{2-8}$ heterocycloalkyl. U may be CR$^3$, W may be CR$^5$, and X may be CR$^6$, each of R$^3$ and R$^6$ being H and R$^5$ being F, Cl, CF$_3$, C$_{1-6}$ alkyl, C$_{2-8}$ heterocycloalkyl, C$_{2-8}$ heterocycloalkenyl, —OR, —C(O) OR, or —C(O)NRR', in which each of R and R', independently, is H, C$_{1-6}$ alkyl, C$_{1-6}$ haloalkyl, C$_{3-8}$ cycloalkyl, or $C_{2-8}$ heterocycloalkyl, or R and R', together with the nitrogen to which they are attached, form $C_{2-8}$ heterocycloalkyl.

U may be N, V may be $CR^4$, W may be $CR^5$, and X may be $CR^6$, $R^6$ being H and each of $R^4$ and $R^5$, independently, being F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR', wherein each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

U may be $CR^3$, V may be N, W may be $CR^5$, and X may be $CR^6$, $R^6$ being H and each of $R^3$ and $R^5$, independently, being F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR', wherein each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

U may be N, V may be $CR^4$, W may be $CR^5$, and X may be $CR^6$, each of $R^4$ and $R^6$ being H and $R^5$ being F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR'; wherein each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

U may be $CR^3$, V may be N, W may be $CR^5$, and X may be $CR^6$, each of $R^3$ and $R^6$ being H and $R^5$ being F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR', wherein each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

$R^1$ may be aryl. $R^1$ may be

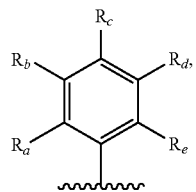

wherein each of $R_a$—$R_e$, independently, is H, halo, OH, CN, $CF_3$, $CHF_2$, $CH_2F$, $NH_2$, $NO_2$, $C_{1-6}$ alkyl, $C_{1-6}$ haloalkyl, $C_{2-6}$ alkenyl, $C_{3-8}$ cycloalkyl, $C_{2-8}$ heterocycloalkyl, $C_{2-8}$ heterocycloalkenyl, aryl, heteroaryl, —C(O)R, —C(O)OR, —C(O)NRR', —C(O)NRS(O)$_2$R', —C(O)NRS(O)$_2$NR'R", —OR, —OC(O)NRR', —NRR', —NRC(O)R', —NRC(O)NR'R", —NRS(O)$_2$R', —NRS(O)$_2$NR'R", —S(O)$_2$R, or —S(O)$_2$NRR', wherein each of R, R', and R", independently, is H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, aryl, or heteroaryl, or R and R', or R' and R", together with the nitrogen to which they are attached, form $C_{2-8}$ heterocycloalkyl.

At least two of $R_b$, $R_c$, and $R_d$ may each be H. Each of $R_b$, $R_c$, and $R_d$ may be H. Each of $R_a$ and $R_e$, may independently be halo or $C_{1-6}$ alkyl. Each of $R_a$ and $R_e$ may be halo. Each of $R_a$ and $R_e$ may be F or Cl. Each of $R_a$ and $R_e$ may be F, and each of $R_b$, $R_c$, and $R_d$ may be H. Each of $R_a$ and $R_e$ may be Cl, and each of $R_b$, $R_c$, and $R_d$ may be H.

$R^1$ may be a 5- or 6-membered heteroaryl. $R^1$ may be a 5-membered heteroaryl. $R^1$ may be a 5-membered heteroaryl containing at least one N. $R^1$ may be a 5-membered heteroaryl selected from the group consisting of pyrrolyl, pyrazolyl, indolyl, indazolyl, and azaindazolyl.

$R^1$ may be a 5-membered heteroaryl containing O or S. $R^1$ may be a 5-membered heteroaryl selected from the group consisting of furanyl, thienyl, benzofuranyl, and benzothienyl. $R^1$ may be a 6-membered heteroaryl containing at least one N. $R^1$ may be an optionally substituted pyridine.

$R^2$ may be H, halo, $C_{1-6}$ alkyl, $C_{1-6}$ alkoxy, $C_{1-6}$ thioalkyl, or $C_{3-8}$ cycloalkyl. $R^2$ may be H, halo, —$CH_3$, —$SCH_3$, or cyclopropyl. $R^2$ may be H, Cl, —$CH_3$, or —$SCH_3$.

The compound of formula (I) may be represented by formula (III):

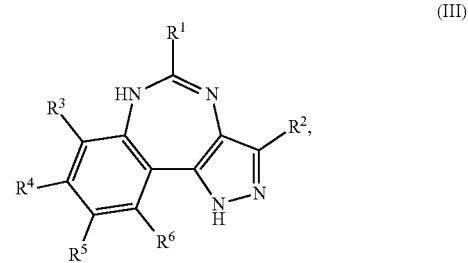

(III)

wherein $R^1$ is aryl or heteroaryl;

$R^2$ is H, halo, OH, CN, $CF_3$, $C_{1-6}$ alkyl, $C_{1-6}$ alkoxy, $C_{1-6}$ haloalkyl, $C_{1-6}$ thioalkyl, or $C_{3-8}$ cycloalkyl; and each of $R^3$—$R^6$, independently, is H, halo, OH, CN, $CF_3$, $CHF_2$, $CH_2F$, $NH_2$, $NO_2$, $C_{1-6}$ alkyl, $C_{1-6}$ haloalkyl, $C_{2-6}$ alkenyl, $C_{3-8}$ cycloalkyl, $C_{2-8}$ heterocycloalkyl, $C_{2-8}$ heterocycloalkenyl, aryl, heteroaryl, —C(O)R, —C(O)OR, —C(O)NRR', —C(O)NRS(O)$_2$R', —C(O)NRS(O)$_2$NR'R", —OR, —OC(O)NRR', —NRR', —NRC(O)R', —NRC(O)NR'R", —NRS(O)$_2$R', —NRS(O)$_2$NR'R", —S(O)$_2$R, or —S(O)$_2$NRR', wherein each of R, R', and R", independently, is H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, aryl, or heteroaryl, or R and R', or R' and R", together with the nitrogen to which they are attached, form $C_{2-8}$ heterocycloalkyl.

Each of $R^3$—$R^6$ may independently be H, halo, OH, CN, $CF_3$, $NH_2$, $NO_2$, $C_{1-6}$ alkyl, $C_{3-8}$ cycloalkyl, $C_{2-8}$ heterocycloalkyl, $C_{2-8}$ heterocycloalkenyl, aryl, heteroaryl, —C(O)OR, —C(O)NRR', —OR, —OC(O)NRR', —NRR', or —NRC(O)R'. At least three of $R^3$—$R^6$ may be H. Each of $R^3$, $R^4$, and $R^6$ may be H. All of $R^3$—$R^6$ may be H. Each $R^3$ and $R^6$ is H, and each of $R^4$ and $R^5$ may independently be halo, OH, CN, $CF_3$, $NH_2$, $NO_2$, $C_{1-6}$ alkyl, $C_{3-8}$ cycloalkyl, $C_{2-8}$ heterocycloalkyl, $C_{2-8}$ heterocycloalkenyl, aryl, heteroaryl, —C(O)OR, —C(O)NRR', —OR, —OC(O)NRR', NRR', or NRC(O)R'. Each of $R^3$, $R^4$, and $R^6$ may be H, and $R^5$ may be halo, OH, CN, $CF_3$, $NH_2$, $NO_2$, $C_{1-6}$ alkyl, $C_{3-8}$ cycloalkyl, $C_{2-8}$ heterocycloalkyl, $C_{2-8}$ heterocycloalkenyl, aryl, heteroaryl, —C(O)OR, —C(O)NRR', —OR, —OC(O)NRR', —NRR', or —NRC(O)R'. Each of $R^3$—$R^6$ may independently be H, halo, $CF_3$, $C_{1-6}$ alkyl, $C_{2-8}$ heterocycloalkyl, $C_{2-8}$ heterocycloalkenyl, —OR, —C(O)OR, or —C(O)NRR'. Each of $R^3$ and $R^6$ may be H, and each of $R^4$ and $R^5$ may independently be halo, $CF_3$, $C_{1-6}$ alkyl, $C_{2-8}$ heterocycloalkyl, $C_{2-8}$ heterocycloalkenyl, —OR, —C(O)OR, or —C(O)NRR'. Each of $R^4$ and $R^5$ may independently be F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR', in which each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl. Each of $R^3$, $R^4$, and $R^6$ may be H, and $R^5$ may be halo, $CF_3$, $C_{1-6}$ alkyl, $C_{2-8}$ heterocycloalkyl, $C_{2-8}$ heterocycloalkenyl, —OR, —C(O)OR, or —C(O)NRR'. $R^5$ may be F, Cl, $CF_3$, $C_{1-6}$ alkyl, $C_{2-8}$ heterocycloalkyl, $C_{2-8}$ heterocycloalkenyl, —OR, —C(O)OR, or —C(O)NRR', in which each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

The compound of formula (I) may be represented by formula (III):

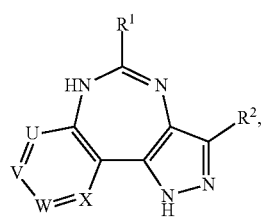

(III)

wherein:
R¹ represents

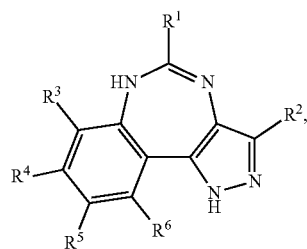

wherein:
each of $R_a$, $R_b$, $R_c$, $R_d$, and $R_e$ is H, Br, F, or Cl;
$R^2$ is H, Cl, —$CH_3$, or —$SCH_3$; and
each of $R^3$ and $R^6$ is H, and each of $R^4$ and $R^5$, independently, is halo, OH, CN, $CF_3$, $CHF_2$, $CH_2F$, $NH_2$, $NO_2$, $C_{1-6}$ alkyl, $C_{3-8}$ cycloalkyl, $C_{2-8}$ heterocycloalkyl, $C_{2-8}$ heterocycloalkenyl, aryl, heteroaryl, —C(O)OR, —C(O)NRR', —OR, —OC(O)NRR', —NRR', or —NRC(O)R', or $R^4$ and $R^5$, together with atoms to which they are attached form a ring having between 5 and 10 members, in which each of R, R', and R", independently, is H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, aryl, or heteroaryl, or R and R', or R' and R", together with the nitrogen to which they are attached, form $C_{2-8}$ heterocycloalkyl.

The compound of formula (I) may be represented by formula (II):

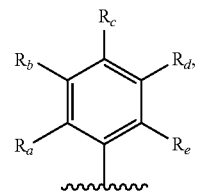

(II)

wherein:
R¹ represents

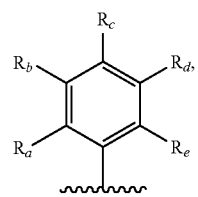

wherein:
each of $R_a$, $R_b$, $R_c$, $R_d$, and $R_e$ is H, Br, F, or Cl;
$R^2$ is H, Cl, —$CH_3$, or —$SCH_3$; and
U is N, V is $CR^4$, W is $CR^5$, and X is $CR^6$, each of $R^4$ and $R^6$ being H and $R^5$ being F, Cl, $CF_3$, $CHF_2$, $CH_2F$, $C_{1-6}$ alkyl, $C_{2-8}$ heterocycloalkyl, $C_{2-8}$ heterocycloalkenyl, —OR, —C(O)OR, or —C(O)NRR', in which each of R, R', and R", independently, is H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, aryl, or heteroaryl, or R and R', or R' and R", together with the nitrogen to which they are attached, form $C_{2-8}$ heterocycloalkyl.

A may be a 5-membered heteroaryl containing at least one N. A may be a 5-membered heteroaryl selected from the group consisting of pyrazolyl, indazolyl, and azaindazolyl.

The compound of formula (I) may be represented by one of the following structures:

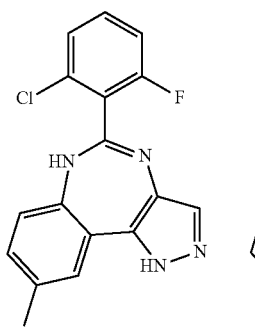 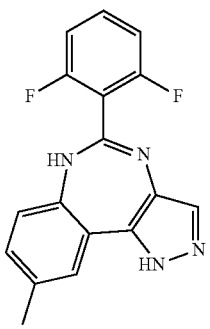

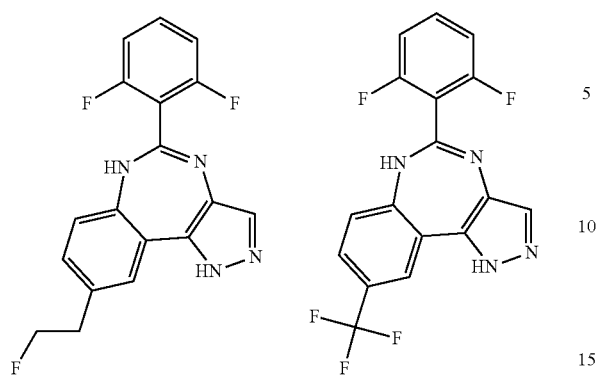
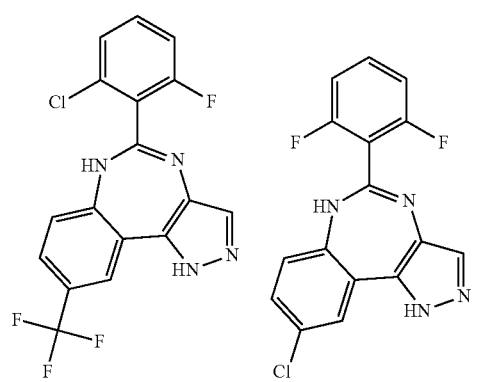
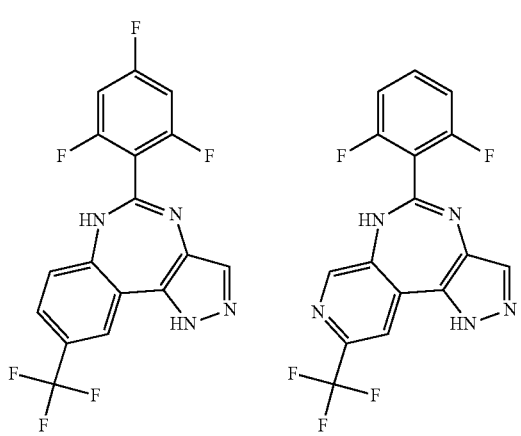
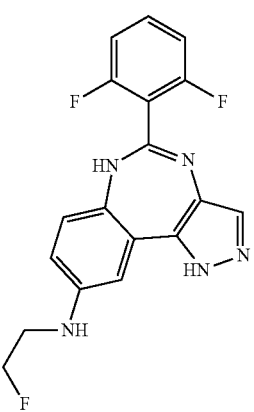
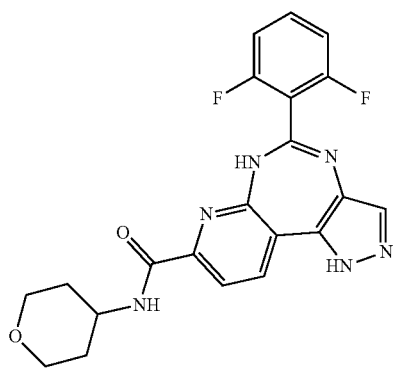
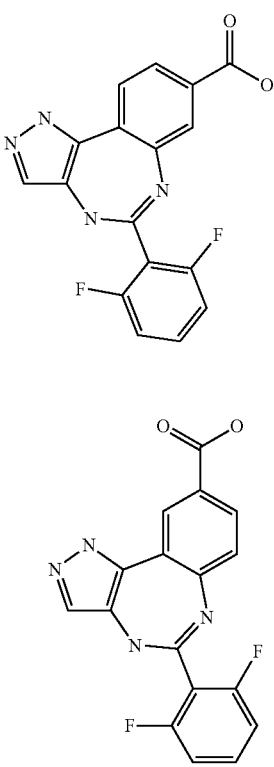
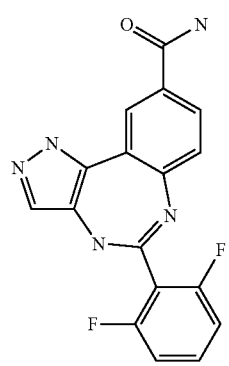

-continued

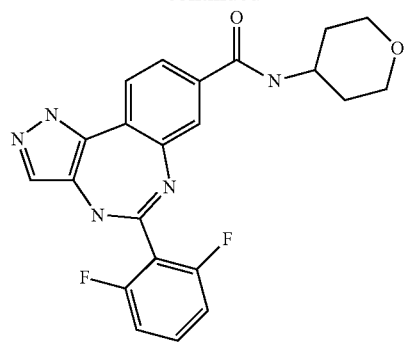

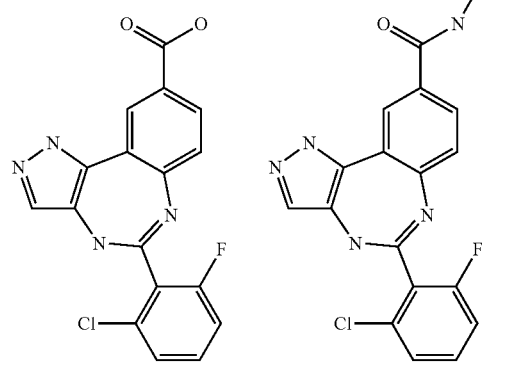

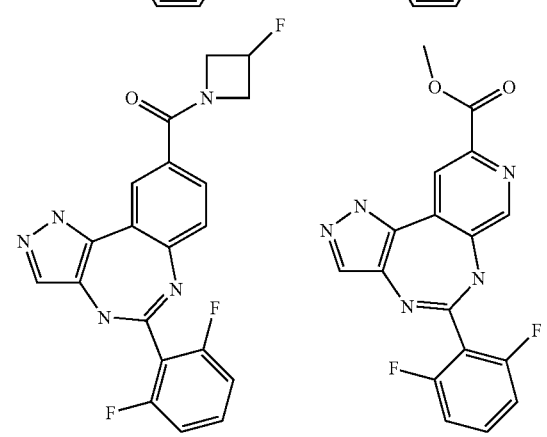

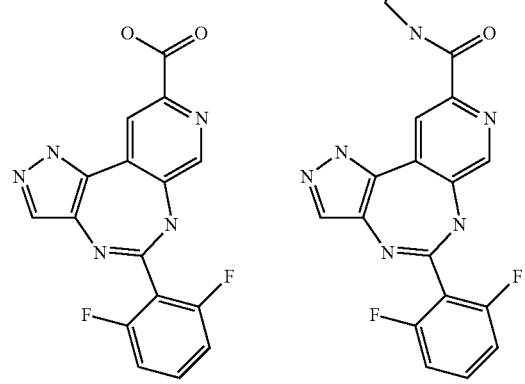

-continued

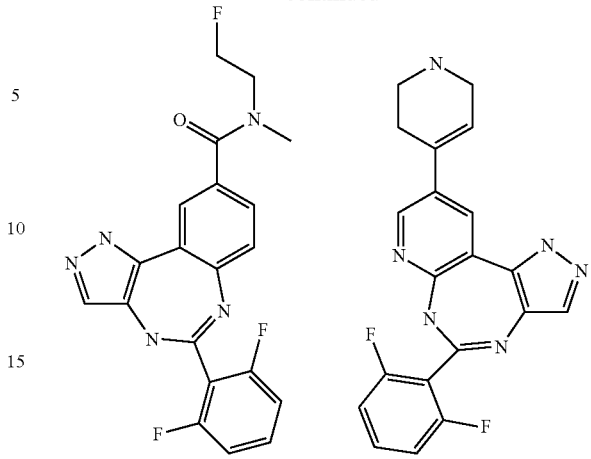

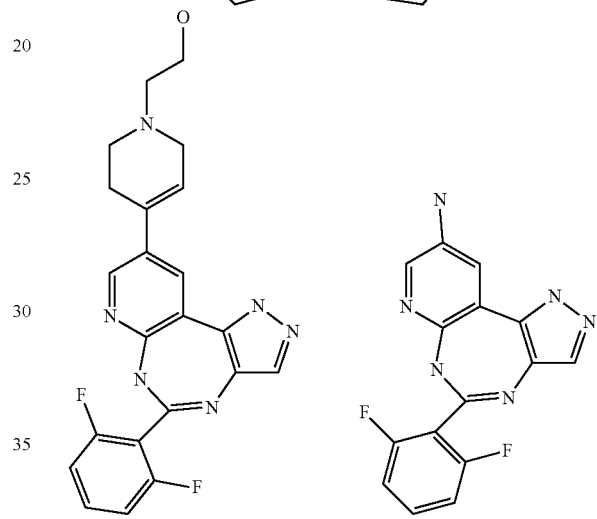

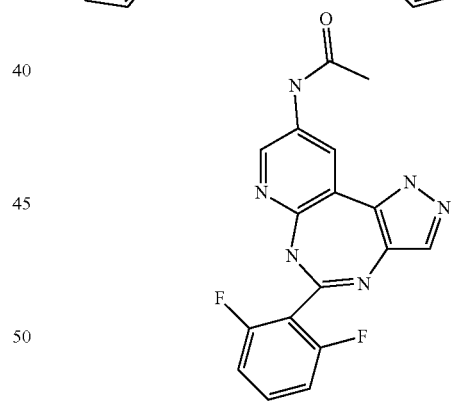

Pharmaceutical Compositions

The present invention provides pharmaceutical compositions comprising one or more compounds of described above or a pharmaceutically acceptable ester, prodrug, hydrate, solvate or salt thereof, optionally in combination with a pharmaceutically acceptable carrier. The invention further provides such compounds for the preparation of a medicament for the treatment of one or more diseases mentioned herein.

A pharmaceutical composition may contain one or more compounds of the invention in a therapeutically effective amount. A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage may be adjusted to the individual requirements in each particular case including the specific compound being administered, the route of administration, the condition being treated, as well as the patient being treated.

Compositions of the invention may include a vehicle for delivery of one or more compounds of the invention. For example, the composition may contain particles, such as nanoparticles, microparticles, liposomes, micelles, and virus particles.

Examples of pharmacologically acceptable salts of sufficiently basic compounds of of the invention are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound of the invention may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl) amine, lysine or arginine salts; all of which are also further examples of salts of the invention. Compounds of the invention may be solvated, especially hydrated. The hydratization/hydration may occur during the process of production or as a consequence of the hygroscopic nature of the initially water free compounds of the invention. The solvates and/or hydrates may e.g. be present in solid or liquid form.

It should be appreciated that certain compounds of the invention may have tautomeric forms from which only one might be specifically mentioned or depicted in the following description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). All these tautomeric forms, geometrical or optical isomers (as well as racemates and diastereomers) and polymorphous forms are included in the invention. Since the compounds of the invention may contain asymmetric C-atoms, they may be present either as achiral compounds, mixtures of diastereomers, mixtures of enantiomers or as optically pure compounds. The present invention comprises both all pure enantiomers and all pure diastereomers, and also the mixtures thereof in any mixing ratio.

According to a further embodiment of the present invention, one or more hydrogen atoms of the compounds of the present invention may be replaced by deuterium. Deuterium modification improves the metabolic properties of a drug with little or no change in its intrinsic pharmacology. Deuterium substitution at specific molecular positions improves metabolic stability, reduces formation of toxic metabolites and/or increases the formation of desired active metabolites. Accordingly, the present invention also encompasses the partially and fully deuterated compounds of the invention. The term hydrogen also encompasses deuterium.

The therapeutic use of compounds according to the invention, their pharmacologically acceptable salts, solvates and hydrates, respectively, as well as formulations and pharmaceutical compositions also lie within the scope of the present invention. The pharmaceutical compositions according to the present invention may comprise at least one compound of the invention as an active ingredient and, optionally, carrier substances and/or adjuvants.

The present invention also relates to pro-drugs which are composed of a compound of the invention and at least one pharmacologically acceptable protective group which will be cleaved off under physiological conditions, such as an alkoxy-, arylalkyloxy-, acyl-, acyloxymethyl group (e.g. pivaloyloxymethyl), an 2-alkyl-, 2-aryl- or 2-arylalkyl oxycarbonyl-2-alkylidene ethyl group or an acyloxy group as defined herein, e.g. ethoxy, benzyloxy, acetyl or acetyloxy or, especially for a compound of the invention, carrying a hydroxy group (—OH): a sulfate, a phosphate (—$OPO_3$ or —$OCH_2OPO_3$) or an ester of an amino acid. For example, compositions may contain pro-drugs of the hydroxy group of a compound of the invention.

As used herein, the term pharmaceutically acceptable ester especially refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The present invention also relates to a prodrug, a biohydrolyzable ester, a biohydrolyzable amide, a polymorph, tautomer, stereoisomer, metabolite, N-oxide, biohydrolyzable carbamate, biohydrolyzable ether, physiologically functional derivative, atropisomer, or in vivo-hydrolysable precursor, diastereomer or mixture of diastereomers, chemically protected form, affinity reagent, complex, chelate and a stereoisomer of the compounds of the invention.

As mentioned above, therapeutically useful agents that contain compounds of the invention, their solvates, salts or formulations are also comprised in the scope of the present invention. In general, compounds of the invention will be administered by using the known and acceptable modes known in the art, either alone or in combination with any other therapeutic agent.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules, the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Particularly useful are lipids, such as phospholipids (e.g., natural origin and/or with a particle size between 300 to 350 nm) in phosphate buffered saline (pH=7 to 8, e.g., 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 10 mg to about 10,000 mg, or from about 20 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

Methods of Making Compounds

The invention also provides methods of making compounds of the invention, such as those described above. Synthesis schemes for making specific compounds of formula (I) are provided in the Examples below.

Methods of Treating Diseases, Disorders and Condition

The compounds and compositions of the invention may be used to diagnose, treat, or prevent a disease, disorder, or condition. The invention further provides methods of using the compounds or compositions of the invention to diagnose or treat a disease, disorder, or condition.

Diseases, disorders, and conditions that can be diagnosed and/or treated using compositions and methods of the invention include those associated with aberrant activity, e.g., increased activity or decreased activity, of one or more kinases. The kinase may be a serine-threonine kinase or a tyrosine kinase, e.g., a receptor tyrosine kinase or non-receptor tyrosine kinase. For example and without limitation, the kinase may be leucine-rich repeat kinase 2 (LRRK2), NUAK family SNF1-like kinase 1 (NUAK1, also known as AMNIPK-related protein kinase 5 or ARK5), or non-receptor tyrosine-protein kinase TYK2 (TYK2), including mutants of any of the aforementioned kinases.

The disease, disorder, or condition may be associated with aberrant LRRK2 activity, such as Alzheimer's disease, Crohn's disease, inflammatory bowel disease, an inflammatory disease, leprosy, neurodegenerative diseases, a non-skin cancer, or Parkinson's disease, including familial Parkinson's disease, sporadic Parkinson's disease, late-onset Parkinson's disease (PD), and type 8 Parkinson's disease.

The disease, disorder, or condition may be associated with aberrant NUAK1 activity, such as cancer, e.g., colorectal cancer, stomach cancer, endometrial cancer, or multiple myeloma, diabetes, fibrosis, a neurodegenerative disease, or omphalocele.

The disease, disorder, or condition may be associated with aberrant TYK2 activity, such as autoimmune disorders, Crohn's disease, hyperimmunoglobulin E syndrome, inflammatory bowel disease, multiple sclerosis (MS), multiple sclerosis (MS), psoriasis, rheumatoid arthritis, systemic lupus erythematosus (SLE), type 1 diabetes (T1D), or ulcerative colitis.

The disease, disorder, or condition may be or include a respiratory tract/obstructive airways disease or disorder, such as rhinorrhea, tracheal constriction, airway contraction, acute-, allergic, atrophic rhinitis or chronic rhinitis (such as rhinitis caseosa, hypertrophic rhinitis, rhinitis purulenta, rhinitis sicca), rhinitis medicamentosa, membranous rhinitis (including croupous, fibrinous and pseudomembranous rhinitis), scrofulous rhinitis, perennial allergic rhinitis, seasonal rhinitis (including rhinitis nervosa (hay fever) and vasomotor rhinitis), pollinosis, asthma (such as bronchial, atopic, allergic, intrinsic, extrinsic, exercise-induced, cold air-induced, occupational, bacterial infection-induced, and dust asthma particularly chronic or inveterate asthma (e.g. late asthma and airways hyper-responsiveness)), bronchitis (including chronic, acute, arachidic, catarrhal, croupus, phthinoid and eosinophilic bronchitis), cardiobronchitis, pneumoconiosis, chronic inflammatory disease of the lung which result in interstitial fibrosis, such as interstitial lung disease (ILD) (e.g., idiopathic pulmonary fibrosis, or ILD associated with rheumatoid arthritis, or other autoimmune conditions), acute lung injury (ALI), adult respiratory distress syndrome (ARDS), chronic obstructive pulmonary, airways or lung disease (CORD, COAD, COLD or COPD, such as irreversible COPD), chronic sinusitis, conjunctivitis (e.g. allergic conjunctivitis), cystic fibrosis, extrinsic allergic alveolitis (like farmer's lung and related diseases), fibroid lung, hypersensitivity lung diseases, hypersensitivity pneumonitis, idiopathic interstitial pneumonia, nasal congestion, nasal polyposis, otitis media, and cough (chronic cough associated with inflammation or iatrogenic induced), pleurisy, pulmonary congestion, emphysema, bronchiectasis, sarcoidosis, lung fibrosis, including cryptogenic fibrosing alveolitis, fibrosis complicating anti-neoplastic therapy and chronic infection, including tuberculosis and aspergillosis and other fungal infections, vasculitic and thrombotic disorders of the lung vasculature, and pulmonary hypertension, acute viral infection including the common cold, and infection due to respiratory syncytial virus, influenza, coronavirus (including SARS) and adenovirus, allergic bronchopulmonary mycosis, emphysema, diffuse panbronchiolitis, systemic anaphylaxis or hypersensitivity responses, drug allergies (e.g., to penicillin, cephalosporins), insect sting allergies, and food related allergies which may have effects remote from the gut (such as migraine, rhinitis and eczema), anaphylactic shock, or vascular spasms.

The disease, disorder, or condition may be or include a bone and joint related disease or disorder, such as osteoporosis, arthritis (including rheumatic, infectious, autoimmune, chronic, malignant), seronegative spondyloarthropathies (such as ankylosing spondylitis, rheumatoid spondylitis, psoriatic arthritis, enthesopathy, Bechet's disease, Marie-Strumpell arthritis, arthritis of inflammatory bowel disease, and Reiter's disease), systemic sclerosis, osteoarthritis, osteoarthrosis, both primary and secondary to e.g. congenital hip dysplasia, cervical and lumbar spondylitis, and low back and neck pain, Still's disease, reactive arthritis and undifferentiated spondarthropathy, septic arthritis and other infection-related arthropathies and bone disorders such as tuberculosis, including Pott's disease and Poncet's syndrome, acute and chronic crystal-induced synovitis including urate gout, calcium pyrophosphate deposition disease, and calcium apatite related tendon, bursar and synovial inflammation, primary and secondary Sjogren's syndrome, systemic sclerosis and limited scleroderma, mixed connective tissue disease, and undifferentiated connective tissue disease, inflammatory myopathies including, polymalgia rheumatica, juvenile arthritis including idiopathic inflammatory arthritides of whatever joint distribution and associated syndromes, other joint disease (such as intervertebral disc degeneration or temporomandibular joint degeneration), rheumatic fever and its systemic complications, vasculitides including giant cell arteritis, Takayasu's arteritis, polyarteritis nodosa, microscopic polyarteritis, and vasculitides to associated with viral infection, hypersensitivity reactions, cryoglobulins, paraproteins, low back pain, Familial Mediterranean fever, Muckle-Wells syndrome, and Familial Hibenian Fever, Kikuchi disease, drug-induced arthalgias, tendonititides, polychondritis, and myopathies, osteoporosis, osteomalacia like osteoporosis, osteopenia, osteogenesis imperfects, osteopetrosis, osteofibrosis, osteonecrosis, Paget's disease of bone, hypophosphatemia, Felty's syndrome, Still's disease, slack of artificial joint implant, sprain or strain of muscle or joint, tendinitis, fasciitis, periarthritis humeroscapularis, cervico-omo-brachial syndrome, or tenosynovitis.

The disease, disorder, or condition may be or include a skin or eye related disease or disorder, such as glaucoma, ocular hypertension, cataract, retinal detachment, psoriasis (including psoriasis vulgaris, pustular psoriasis, arthritic psoriasis, erythroderma psoriaticum), palmoplantar pustulosis, xerodoma, eczematous diseases (like atopic dermatitis, ultraviolet radiation dermatitis, contact dermatitis, and seborrheic dermatitis), phytodermatitis, photodermatitis, cutaneous eosinophilias, chronic skin ulcers, cutaneous lupus erythematosus, contact hypersensitivity/allergic contact dermatitis (including sensitivity to poison ivy, sumac, or oak), and eosinophilic folliculitis (Ofuji's disease), pruritus, drug eruptions, urticaria (acute or chronic, allergic or non-allergic), acne, erythema, dermatitis herpetiformis, scleroderma, vitiligo, lichen planus, lichen sclerosus et atrophica, pyodenna gangrenosum, skin sarcoid, pemphigus, ocular pemphigus, pemphigoid, epidermolysis bullosa, angioedema, vasculitides, toxic erythemas, cutaneous eosinophilias, alopecia areata, male-pattern baldness, Sweet's syndrome, Stevens-Johnson syndrome, Weber-Christian syndrome, erythema multiforme, cellulitis, both, infective and non infective, panniculitis, cutaneous Lymphomas, non-melanoma skin cancer and other dysplastic lesions, blepharitis, iritis, anterior and posterior uveitis, choroiditis, autoimmune, degenerative or inflammatory disorders affecting the retina, ophthalmitis including sympathetic ophthalmitis, sarcoidosis, xerosis infections including viral, fungal, and bacterial, allergic conjunctivitis, increased fibrosis, keloids, keloplasty, post surgical scars, epidermolysis bullosa, dry eye, ocular inflammation, allergic conjunctivitis, vernal conjunctivitis, vernal keratoconjunctivitis, and giant papillary conjunctivitis, ocular angiogenesis, cornea damage and scar, all forms of macular degeneration, macular edema, macular dystrophy, abnormal wound healing, scleritis, episcleritis, pachydermia, peripheral ulcerative keratitis, fungal keratitis, herpetic keratitis, invasive aspergillosis; conical cornea, dystorphia epithelialis comeae, or severe intraocular inflammation.

The disease, disorder, or condition may be or include a gastrointestinal tract and abdominal related disease or disorder, such as celiac/coeliac disease (e.g. celiac sprue), cholecystitis, enteritis (including infectious, ischemic, radiation, drug-induced, and eosinophilic gastroenteritis), eosinophilic esophagitis, eosinophilic gastrointestinal inflammation, allergen induced diarrhea, enteropathy associated with seronegative arthropathies, gastritis, autoimmune atrophic gastritis, ischemic bowel disease, inflammatory bowel disease (Crohn's disease and ulcerative colitis), colitis, Mooren's ulcer, irritable bowel syndrome, necrotizing enterocolitis, gut ischemia, glossitis, gingivitis, periodontitis, oesophagitis, including reflex, proctitis, fibrosis and cirrhosis of the liver, pancreatitis, both acute and chronic, pancreatic fibrosis, pancreatic sclerosis, pancreatolithiasis, hepatic cirrhosis, hepatitis (congestive, autoimmune, acute, fulminant, chronic, drug-induced, alcoholic, lupoid, steatohepatitis and chronic viral), fatty liver, primary biliary cirrhosis, hepatic porphyria, and gastrointestinal related allergic disorders, spastic colon, diverticulitis, gastroenteric bleeding, Behcet's disease; partial liver resection, acute liver necrosis (e.g. necrosis caused by toxins, viral hepatitis, shock or anoxia), or hemolytic uremic syndrome.

The disease, disorder, or condition may be or include a hematological disease or disorder, such as anemias, coagulation, myeloproliferative disorders, hemorrhagic disorders, leukopenia, eosinophilic disorders, leukemias (e.g. myelogenous, lymphomas, plasma cell dyscrasias, disorders of the spleen, Band's disease, hemophilia, purpura (including idiopathic thrombocytopenic purpura), or Wiskott-Aldrich syndrome.

The disease, disorder, or condition may be or include a metabolic disease or disorder, such as obesity, amyloidosis, disturbances of the amino and acid metabolism like branched chain disease, hyperaminoacidemia, hyperaminoaciduria, disturbances of the metabolism of urea, hyperammonemia, mucopolysaccharidoses e.g. Maroteaux-Lamy syndrome, storage disease like glycogen storage diseases and lipid storage diseases, glycogenosis I diseases like Cori's disease, malabsorption diseases like intestinal carbohydrate malabsorption, oligosaccharidase deficiency like maltase-, lactase-, sucrase-insufficiency, disorders of the metabolism of fructose, disorders of the metabolism of galactose, galactosaemia, disturbances of carbohydrate utilization like diabetes, hypoglycemia, disturbances of pyruvate metabolism, hypolipidemia, hypolipoproteinemia, hyperlipidemia, hyperlipoproteinemia, carnitine or carnitine acyltransferase deficiency, disturbances of the porphyrin metabolism, porphyrins, disturbances of the purine metabolism, lysosomal diseases, metabolic diseases of nerves and nervous systems like gangliosidoses, sphingolipidoses, sulfatidoses, leucodystrophies, or Lesch Nyhan syndrome.

The disease, disorder, or condition may be or include a cerebellar dysfunction or disturbance of brain metabolism, such as dementia, Alzheimer's disease, Huntington's chores, Parkinson's disease, Pick's disease, toxic encepha-lopathy, demyelinating neuropathies like inflammatory neuropathy, Guillain-Barre syndrome; Meniere's disease and radiculopathy, primary and secondary metabolic disorders associated with hormonal defects like any disorder stemming from either an hyperfunction or hypofunction of some hormone-secreting endocrine gland and any combination thereof. Sipple's syndrome, pituitary gland dysfunction and its effects on other endocrine glands, such as the thyroid, adrenals, ovaries, and testes, acromegaly, hyper- and hypothyroidism, euthyroid goiter, euthyroid sick syndrome, thyroiditis, and thyroid cancer, over or underproduction of the adrenal steroid hormones, adrenogenital syndrome, Cushing's syndrome, Addison's disease of the adrenal cortex, Addison's pernicious anemia, primary and secondary aldosteronism, diabetes insipidus, diabetes mellitus, carcinoid syndrome, disturbances caused by the dysfunction of the parathyroid glands, pancreatic islet cell dysfunction, diabetes, disturbances of the endocrine system of the female like estrogen deficiency, resistant ovary syndrome; muscle weakness, myotonia. Duchenne's and other muscular dystrophies, dystrophia myotonica of Steinert, mitochondrial myopathies like disturbances of the catabolic metabolism in the muscle, carbohydrate and lipid storage myopathies, glycogenoses, myoglobinuria, malignant hyperthermia, polymyalgia rheumatics, dermatomyositis, multiple myositis, primary myocardial disease, cardiomyopathy; disorders of the ectoderm, neurofibromatosis, scleroderma and polyar teritis, Louis-Bar syndrome, von Hippel-Lindau disease, Sturge-Weber syndrome, tuberous sclerosis, amyloidosis, porphyria; sexual dysfunction of the male and female; confused states and seizures due to inappropriate secretion of antidiuretic hormone from the pituitary gland, Liddle's syndrome, Bartter's syndrome, Fanconi's I syndrome, or renal electrolyte wasting.

The disease, disorder, or condition may be or include a transplant rejection related condition, such as acute and chronic allograft rejection following solid organ transplant, for example, transplantation of kidney, heart, liver, lung, and cornea, chronic graft versus host disease, skin graft rejection, and bone marrow transplant rejection, or immunosuppression.

The disease, disorder, or condition may be or include a genitourinary related condition, such as nephritis (interstitial, acute interstitial (allergic), and glomerulonephritis), nephrotic syndrome, cystitis including acute and chronic (interstitial) cystitis and Hunner's ulcer, acute and chronic urethritis, prostatitis, epididymitis, oophoritis, salpingitis, vulvo vaginitis, vulvovaginal candidiasis, Peyronie's disease, and erectile dysfunction, renal disease, renal fibrosis, nephropyelitis, secondary contracted kidney, steroid dependent and steroid-resistant nephrosis, or Goodpasture's syndrome.

The disease, disorder, or condition may be or include a CNS related disease or disorder, such as neurodegenerative diseases, Alzheimer's disease and other cementing disorders including CJD and nvCJD, amyloidosis, and other demyelinating syndromes, cerebral atherosclerosis and vasculitis, temporal arteritis, myasthenia gravis, acute and chronic so pain (acute, intermittent or persistent, whether of central or peripheral origin) including post-operative, visceral pain, headache, migraine, neuralgia (including trigeminal), atypical facial pain, joint and bone pain, pain arising from cancer and tumor invasion, neuropathic pain syndromes including diabetic, post-herpetic, and HIV-associated neuropathies, neurosarcoidosis, to brain injuries, cerebrovascular diseases and their consequences, Parkinson's disease, corticobasal degeneration, motor neuron disease, dementia, including ALS (Amyotrophic-lateral sclerosis), multiple sclerosis, traumatic brain injury, stroke, post-stroke, post-traumatic brain injury, and small-vessel cerebrovascular disease, dementias, vascular dementia, dementia with Lewy bodies, frontotemporal dementia and Parkinsonism linked 1 to chromosome 17, frontotemporal dementias, including Pick's disease, progressive supranuclear palsy, corticobasal degeneration, Huntington's disease, thalamic degeneration, HIV dementia, schizophrenia with dementia, and Korsakoffs psychosis, within the meaning of the definition are also considered to be CNS disorders central and peripheral nervous system complications of malignant, infectious or autoimmune processes, algesia, cerebral infarction, attack, cerebral ischemia, head injury, spinal cord injury, myelopathic muscular atrophy, Shy-Drager syndrome, Reye's syndrome, progressive multifocal leukoencephalopathy, normal pressure hydrocephalus, sclerosing panencephalitis, frontal lobe type dementia, acute anterior poliomyelitis (poliomyelitis), poliomyelitis neurosis, viral encephalitis, allergic encephalomyelitis, epileptic encephalopathies, Creutzfeldt-Jakob disease, Kuru disease, bovine spongiform encephalopathy (mad cow disease), scrapie, epilepsy, cerebral amyloid angiopathy, depression, mania, manic-depressive psychosis, hereditary cerebellar ataxia, peripheral neuropathy, Nasu-Hakola syndrome, or Machado-Joseph disease.

The disease, disorder, or condition may be or include an inflammatory or immunological disease or disorder, such as general inflammation (of the ocular, nasal, pulmonary, and gastrointestinal passages), mastocytosis/mast cell disorders (cutaneous, systemic, mast cell activation syndrome, and pediatric mast cell diseases), mastitis (mammary gland), vaginitis, vasculitis (e.g., necrotizing, cutaneous, and hypersensitivity vasculitis), Wegener granulamatosis, myyositis (including polymyositis, dermatomyositis), basophil related diseases including basophilic leukemia and basophilic leukocytosis, and eosinophil related diseases such as Churg-Strauss syndrome, eosinophilic granuloma, lupus erythematosus (such as, systemic lupus erythematosus, subacute cutaneous lupus erythematosus, and discoid lupus erythematosus), chronic thyroiditis, Hashimoto's thyroiditis, Grave's disease, type I diabetes, complications arising from diabetes mellitus, other immune disorders, eosinophilia fasciitis, hyper IgE syndrome, Addison's disease, antiphospholipid syndrome, immunodeficiency disease, acquired immune deficiency syndrome (AIDS), leprosy, Sezary syndrome, paraneoplastic syndromes, and other autoimmune disorders, fervescence, myositis, nervous diseases selected from multiple myositis, bursitis, Evans syndrome, leukotriene B4-mediated diseases, idiopathic hypoparathyroidism, nephrotic syndrome lupus, or immunosuppression.

The disease, disorder, or condition may be or include a cardiovascular disease or disorder, such as congestive heart failure, myocardial infarction, ischemic diseases of the heart, all kinds of atrial and ventricular arrhythmias, hypertension, cerebral trauma, occlusive vascular disease, stroke, cerebrovascular disorder, atherosclerosis, restenosis, affecting the coronary and peripheral is circulation, pericarditis, myocarditis, inflammatory and auto-immune cardiomyopathies including myocardial sarcoid, endocarditis, valvulitis, and aortitis including infective (e.g. syphilitic), hypertensive vascular diseases, peripheral vascular diseases, and atherosclerosis, vasculitides, disorders of the proximal and peripheral veins including phlebitis and thrombosis, including deep vein thrombosis and complications of varicose veins, aortic aneurism, periarteritis nodosa, cardiac fibrosis, post-myocardial infarction, idiopathic cardiomyopathy, or angioplasty.

The disease, disorder, or condition may be or include an oncological disease or disorder, such as common cancers (prostrate, breast, lung, ovarian, pancreatic, bowel and colon, abdomen, stomach (and any other digestive system cancers), liver, pancreas, peritoneum, endocrine glands (adrenal, parathyroid, pituitary, testicles, ovary, thymus, thyroid), eye, head, neck, nervous system (central and peripheral), lymphatic system, blood, pelvic, skin, bone, soft tissue, spleen, thoracic, urogenital, and brain tumors), breast cancer, genitourinary cancer, lung cancer, gastrointestinal cancer, epidermoid cancer, melanoma, ovarian cancer, pancreas cancer, neuroblastoma, malignancies affecting the bone marrow (including the leukaemias) and lymphoproliferative systems, such as Hodgkin's and non-Hodgkin's lymphoma, B-cell lymphoma, follicular lymphoma, metastatic disease and tumour recurrences, and paraneoplastic syndromes, as well as hypergammaglobulinemia, lymphoproliferative diseases, disorders, and/or conditions, paraproteinemias, purpura (including idiopathic thrombocytopenic purpura), Waldenstron's Macroglobulinemia, Gaucher's Disease, histiocytosis, retinoblastoma and any other hyperproliferative disease, sarcomata, cachexia, tumor growth, tumor invasion, metastasis, AIDS-related lymphomas, malignant immunoproliferative diseases, multiple myeloma and malignant plasma cell neoplasms, lymphoid leukemia, acute or chronic myeloid leukemia, acute or chronic lymphocytic leukemia, monocytic leukemia, other leukemias of specified cell type, leukemia of unspecified cell type, other and unspecified malignant neoplasms of lymphoid, haematopoietic and related tissues, for example diffuse large cell lymphoma, T-cell lymphoma or cutaneous T-cell lymphoma). Myeloid cancer includes e.g. acute or chronic myeloid leukaemia, or keratoleukoma.

The disease, disorder, or condition may be or include another disease or disorder, such as pain, migraine, sleep disorders, fever, sepsis, idiopathic thrombocytopenia pupura, post-operative adhesions, flushing, ischemic/reperfusion injury in the heart, brain, peripheral limbs, bacterial infection, viral infection, fungal infection, thrombosis, endotoxin shock, septic shock, thermal regulation including fever, Raynaud's disease, gangrene, diseases requiring anticoagulation therapy, congestive heart failure, mucus secretion disorders, pulmonary hypotension, prostanoid-induced smooth muscle contract associated with dysmenorrhea and premature labor, premature delivery, reperfusion injury, burn, thermal injury, hemorrhage or traumatic shock, menstrual pain, menstrual cramp, dysmenorrhea, periodontosis, rickettsial infectious disease, protozoal disease, reproduction disease, toothache, pain after tooth extraction, Herpes zoster, Herpes simplex, retroperitoneal fibrosis, or various radiation injuries.

In certain embodiments, the disease is selected from the group consisting of an inflammatory disease, an autoimmune disease, an allergic disorder, and an ocular disorder. In certain embodiments, the disease is selected from the group consisting of pruritus, eczema, asthma, rhinitis, dry eye, ocular inflammation, allergic conjunctivitis, vernal conjunctivitis, vernal keratoconjunctivitis, giant papillary conjunctivitis, fungal keratitis and uveitis.

The method may include modulating the activity of one or more kinases in a subject, such as any of the kinase described above. The method may include inhibiting a kinase. The method may include activating, e.g., stimulating or enhancing the activity of, a kinase. The method may include modulating a single kinase or preferentially modulating a specific kinase over others. The method may include modulating multiple kinases or preferentially modulating two more specific kinases over others.

The method may include providing a compound of the invention. The method may include providing multiple compounds of the invention.

The method may include contacting cells containing a kinase with one or more compounds of the invention. For example and without limitation, contacting a cell with a compound may include exposing a cell to a compound, e.g., in a formulation, such as any of those described above; delivering a compound inside a cell; providing a compound to a subject and allowing a cell in the subject to become exposed to the compound. Contacting may be performed in vivo or in vitro. In vitro contact may include exposure of cells or tissue isolated from a subject. The method may include contacting cells with a single compound of the invention. The method may include contact cells with multiple compounds of the invention.

The method may include administration of a composition to a subject. The compositions may be provided by any suitable route of administration. For example and without limitation, the compositions may be administered buccally, by injection, dermally, enterally, intraarterially, intravenously, intranasally, e.g., by inhalation, intraocularly, orally, parenterally, pulmonarily, rectally, subcutaneously, systemically, topically, e.g., to the skin or eye, transdermally, or with or on an implantable medical device (e.g., stent or drug-eluting stent or balloon equivalents).

The method may include using a composition of the invention to diagnose a disease, disorder, or condition in a subject. For example, a radiolabeled form of a compound may be used a tracer in positron emission tomography (PET)

to identify anatomical locations of aberrant kinase activity. PET is known in the art and described in, for example, Wadsak Wolfgang, Mitterhauser Markus (2010), "Basics and principles of radiopharmaceuticals for PET/CT", European Journal of Radiology, 73 (3): 461-469. doi:10.1016/j.ejrad.2009.12.022; Bailey, D. L; D. W. Townsend; P. E. Valk; M. N. Maisey (2005), Positron Emission Tomography: Basic Sciences. Secaucus, N.J.: Springer-Verlag, ISBN 1-85233-798-2; and Carlson, Neil (Jan. 22, 2012). Physiology of Behavior. Methods and Strategies of Research, 11th edition, Pearson, p. 151, ISBN 0205239390, the contents of each of which are incorporated herein by reference. The invention may include administering one or more compositions of the invention for both diagnostic and therapeutic purposes.

EXAMPLES

Example 1

The following methods were used in synthesis of compounds described herein.

Flash chromatography: Flash chromatography is performed on a Biotage Isolera® system using SNAP silica cartridges and ethylacetate/cyclohexan/methanol or dichloromethane/methanol gradients as eluent.

Microwave conditions: Reactions under microwave conditions are performed in a Biotage Initiator® microwave system.

SEMIprep reversed phase chromatography: The following instrumentation was used for SEMIprep reversed phase chromatography: 2× Varian PrepStar SD-1, 1× Dionex P580 Pump 1 Channel(MakeUP I), 1× Dionex AXP-MS (MakeUP II), 1× Dionex MSQ, 1× Dionex UVD 340V—Prep Flow Cell, and Gilson 215 Liquid Handler. A SunFire Prep C18 OBD 5 μm, 19×50 mm column was used.

In a typical experiment, column flow was 30 mL/min, Solvent A was methanol containing 0.3% acetic acid, and Solvent B was water containing 0.3% acetic acid. Typical times and relative volumes of Solvent and Solvent B were as follows:

| Time (min) | Solv. A | Solv. B |
|---|---|---|
| 0.0 | 30.00 | 70.00 |
| 10.0 | 100.00 | 0.00 |
| 14.0 | 100.00 | 0.00 |
| 14.4 | 30.00 | 70.00 |
| 16.4 | 30.00 | 70.00 |

A Mass Spectrometer Detector (API-ES, positive) at UV 254 nm was used for detection.

Example 2

Terms and abbreviations used in the Examples are provided in Table 1.

TABLE 1

Pd dppf - [1,1'-Bis(diphenylphosphino)ferrocene]dichloropalladium(II), complex with dichloromethane CAS 95464-05-4
DCM - dichloromethan
THF- tetrahydofuran
MeOH- methanol
celite - Diatomaceous earth, celite (R) CAS 61790-53-2
diborolan - 4,4,5,5,4',4',5',5'-Octamethyl-[2,2']bi[[1,3,2]dioxaborolanyl] CAS 73183-34-3
pinacolboran - 4,4,5,5-Tetramethyl-[1,3,2]dioxaborolane CAS 25015-63-8
o.n. - over night
r.t. - room temperature
eq. - equivalent
dioxan - 1,4-dioxane
brine - saturated aqueous solution of NaCl
h - hour
TFA - trifluoro acetic acid
catacxium- cataCXium ® A, Di(1-adamantyl)-n-butylphosphine, CAS 321921-71-5
LiHMDS - Lithium bis(trimethylsilyl)amide CAS 4039-32-1
Pd(PPh$_3$)$_4$ - Palladium-tetrakis(triphenylphosphine) CAS 14221-01-3
PYBOP - (Benzotriazol-1-yloxy)tripyrrolidinophosphonium hexafluorophosphate CAS 128625-52-5
DIPEA - N,N-Diisopropylethylamine CAS 7087-68-5
DMF - N,N-Dimethylformamide CAS 68-12-2
DBAD - Di-tert-butyl azodicarboxylate CAS 870-50-8
PPh$_3$ - Triphenylphosphine CAS 603-35-0
HOBT - 1-Hydroxybenzotriazole hydrate CAS 123333-53-9
EDCI - N-(3-Dimethylaminopropyl)-N'-ethylcarbodiimide hydrochloride CAS 25952-53-8
T3P - T3P ® 2,4,6-Tripropyl-1,3,5,2,4,6-trioxatriphosphorinane-2,4,6-trioxide CAS 68957-94-8

Example 3

Methods of synthesis of certain molecules that were used as reagents in synthesis schemes described herein are known in the art and described in references as provided in Table 2.

TABLE 2

| Compound | Reference |
|---|---|
| (structure: tetrahydropyranyl-pyrazole with Cl and NO$_2$) | WO2013/164323A1 |
| (structure: 4-methoxybenzyl-pyrazole with Cl and NO$_2$) | US2014/088117A1 |

TABLE 2-continued

| Compound | Reference |
|---|---|
| 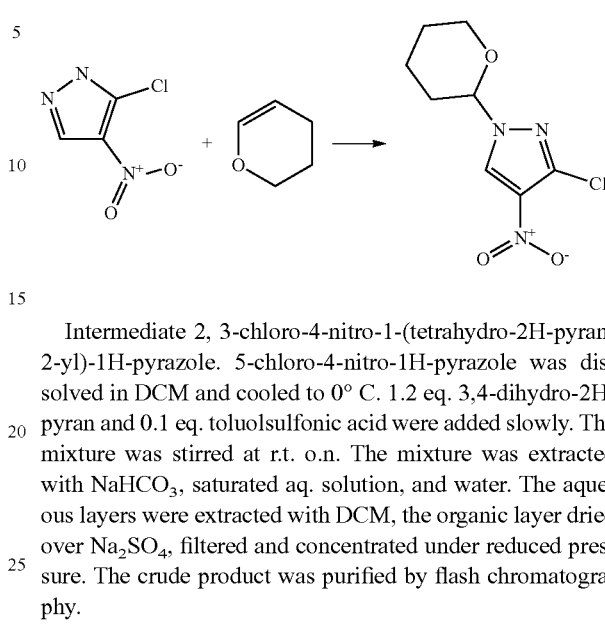 | WO2013/164323A1 (synthesized analog using 1,2-Dibromo-1,1,2,2-Tetrachloroethan instead of 1,1,1,2,2,2-Hexachloroethan) |
| 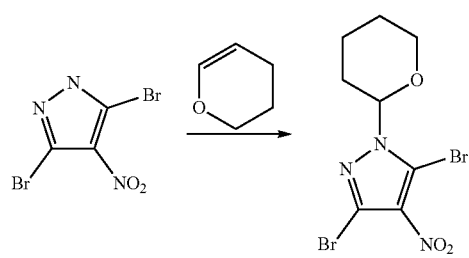 | J. P. H. Juffermans and Clarisse L. Habraken, The Journal of Organic Chemistry 1986, 51, 24, 4656-4660, Nov. 1, 1986 |
| 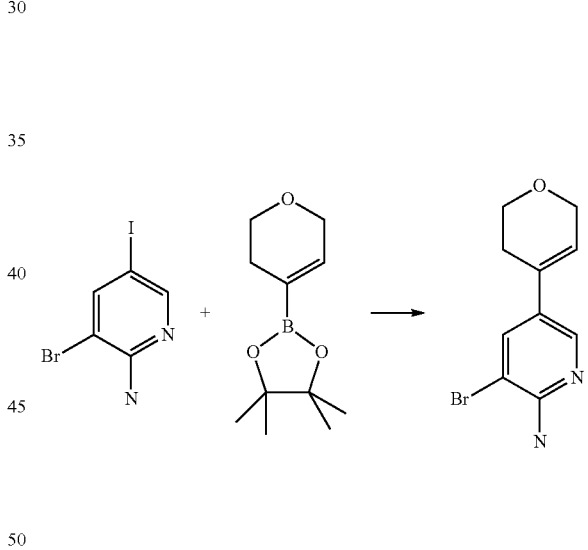 | |

Example 4

Intermediate 1. 1 eq. 3,5-dibromo-4-nitropyrazole was suspend in dichloromethane, THF was added until complete solution. Then 1.3 eq. dihydropyran and a catalytic amount of toluolsulfonic acid mono hydrate were added. The mixture was stirred o.n., then diluted with DCM, washed with NaHCO₃, saturated aq. solution, and water. The combined organics were dried over Na₂SO₄, filtered and evaporated under reduced pressure to give the desired product as white solid. The product was used without further purification. See J. P. H. Juffermans and Clarisse L. Habraken, The Journal of Organic Chemistry 1986, 51, 24, 4656-4660, Nov. 1, 1986

Example 5

Intermediate 2, 3-chloro-4-nitro-1-(tetrahydro-2H-pyran-2-yl)-1H-pyrazole. 5-chloro-4-nitro-1H-pyrazole was dissolved in DCM and cooled to 0° C. 1.2 eq. 3,4-dihydro-2H-pyran and 0.1 eq. toluolsulfonic acid were added slowly. The mixture was stirred at r.t. o.n. The mixture was extracted with NaHCO₃, saturated aq. solution, and water. The aqueous layers were extracted with DCM, the organic layer dried over Na₂SO₄, filtered and concentrated under reduced pressure. The crude product was purified by flash chromatography.

Example 6

Intermediate 3, 3-bromo-5-(3,6-dihydro-2H-pyran-4-yl)pyridin-2-amine. 3-bromo-5-iodopyridin-2-amine is dissolved in dioxane and water. 1 eq. 2-(3,6-dihydro-2H-pyran-4-yl)-4,4,5,5-tetramethyl-1,3,2-dioxaborolane and 3 eq. Na₂CO₃ were added. The mixture was degassed with N₂ before 0.05 eq. Pd(PPh₃)₄ was added. The mixture was degassed again and stirred at 80° C. o.n. Additional 0.02 eq. Pd(PPh₃)₄ were added and the mixture stirred for 4 h at 80° C. The mixture was cooled to r.t. and filtered over celite. The solids were washed with MeOH and water. The filtrate was concentrated under reduced pressure, diluted with water and extracted with DCM. The organic layer was dried over Na₂SO₄, filtered and evaporated. The crude material was purified by flash chromatography.

Example 7

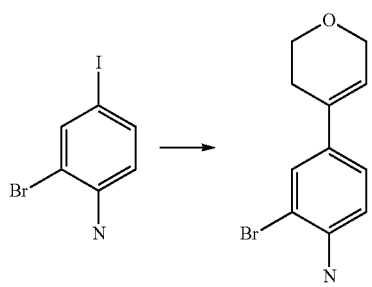 [SMILES: Nc1ccc(I)cc1Br ; Nc1ccc(C2=CCOCC2)cc1Br]

Intermediate 4, 2-bromo-4-(3,6-dihydro-2H-pyran-4-yl) aniline. Synthesized as described in Intermediate 3 using 2-bromo-4-iodoaniline as starting material.

Example 8

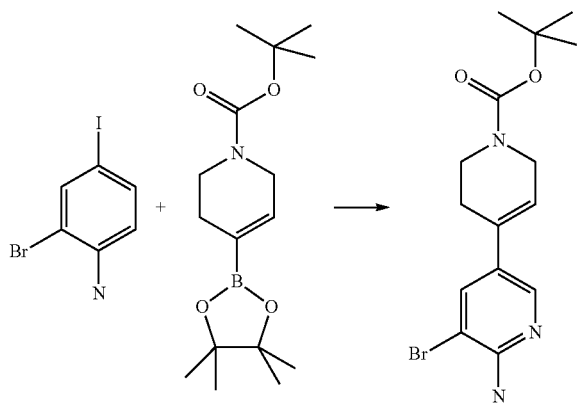 [SMILES: Nc1ccc(I)cc1Br ; CC(C)(C)OC(=O)N1CC=C(B2OC(C)(C)C(C)(C)O2)CC1 ; CC(C)(C)OC(=O)N1CC=C(c2cnc(N)c(Br)c2)CC1]

Intermediate 5, tert-butyl 6-amino-5-bromo-5',6'-dihydro-[3,4'-bipyridine]-1'(2'H)-carboxylate. Synthesized as described in Intermediate 3 using tert-butyl 4-(4,4,5,5-tetramethyl-1,3,2-dioxaborolan-2-yl)-5,6-dihydropyridine-1 (2H)-carboxylate as a starting material.

Example 9

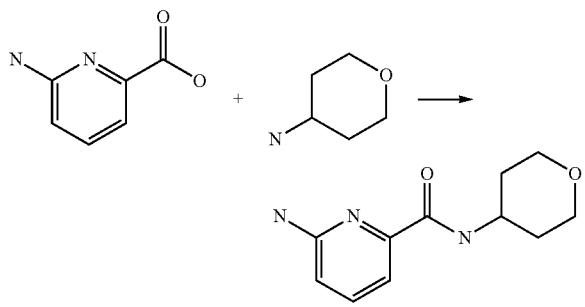

Intermediate 6, 6-amino-pyridine-2-carboxylic acid (tetrahydro-pyran-4-yl)-amide. 1 eq. 6-amino-pyridine-2-carboxylic acid and tetrahydro-pyran-4-ylamine was dissolved in dry DMF. 1.05 eq. PYBOP and 2.1 eq. DIPEA were added. The mixture was stirred at r.t. for 3 h. The mixture was diluted with ethyl acetate, washed with NaHCO$_3$, saturated aq. solution, and water. The combined organics were dried over Na$_2$SO$_4$, filtered and concentrated under reduced pressure. The crude product was purified by flash chromatography.

Example 10

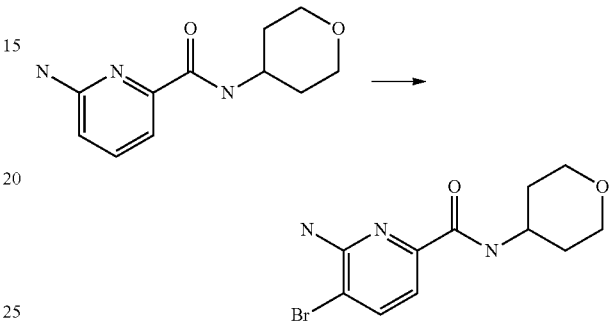

Intermediate 7. 6-Amino-pyridine-2-carboxylic acid (tetrahydro-pyran-4-yl)-amide was dissolved in chloroform/DCM 3/1. The mixture was cooled to 0° C. 1.3 eq. bromine were added drop wise and the mixture stirred at r.t. for 3 days. The mixture was quenched with Na$_2$S2O3, 5% w/v aq. solution, basified with NaOH aq., extracted with DCM. The combined organics were dried over Na$_2$SO$_4$, filtered and concentrated under reduced pressure. The crude mixture was purified by flash chromatography.

Example 11

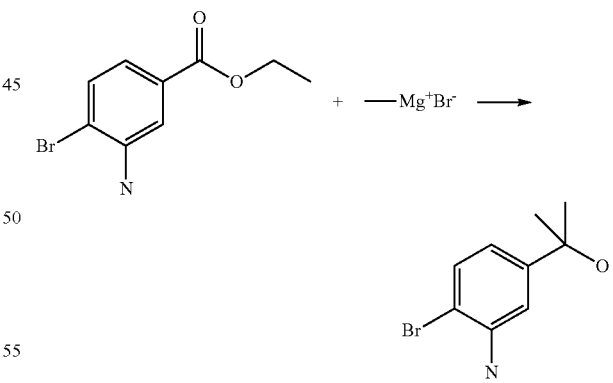

Intermediate 8, 2-(3-amino-4-bromophenyl)propan-2-ol. Ethyl 3-amino-4-bromobenzoate was dissolved in dry THE and cooled to 0° C. 6 eq. 1.4M methyl magnesium bromide in THF/toluene (1/3) were added and the mixture stirred for 30 min at 0° C. The reaction mix was quenched by addition of NH$_4$C$_1$ sat. aq. and extracted with ethyl acetate. The organic layer was dried over Na$_2$SO$_4$, filtered and concentrated under reduced pressure. The crude product was purified by flash chromatography.

Example 12

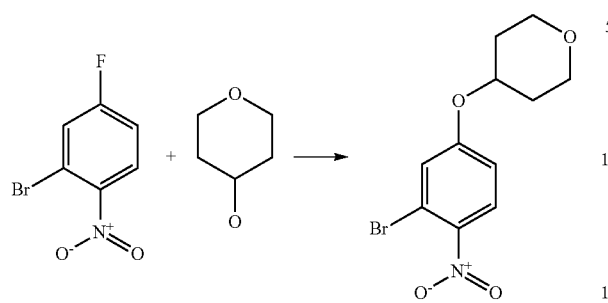

Intermediate 9, 4-(3-bromo-4-nitrophenoxy)tetrahydro-2H-pyran. Tetrahydro-2H-pyran-4-ol was dissolved in dry DMF and cooled to 0° C. 1.8 eq. NaH, 60% dispersion in oil, was added, followed by drop wise addition of 2-bromo-4-fluoro-1-nitrobenzene. The mixture was heated to reflux for 45 min then cooled to r.t. and quenched by adding water. The precipitate was collected by filtration. The filtrate was extracted with ethyl acetate, the organic layer washed with brine, dried over $Na_2SO_4$, filtered and concentrated under reduced pressure. The combined crude product was purified by flash chromatography.

Example 13

General procedure for iron reductions: An aryl nitro compound is dissolved in ethanol/water 4/1, 10 eq. iron and 10 eq. $NH_4Cl$, and some drops of 2M HCl are added. The mixture is heated at 50° C. for 1 h. The mixture is filtered over celite, the solids are washed with MeOH and water. The filtrate is concentrated and then basified with NaOH 15% w/v. The aqueous layer is extracted with ethyl acetate, the combined organic layers are dried over $Na_2SO_4$, filtered and concentrated under reduced pressure. The product is used without further purification.

Example 14

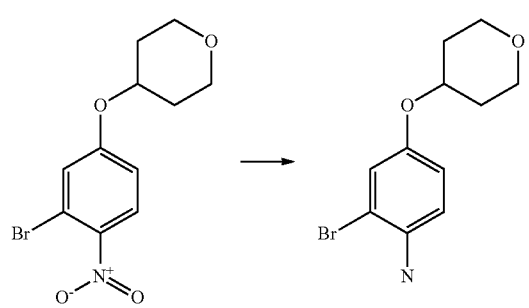 [SMILES: O=[N+]([O-])c1ccc(OC2CCOCC2)cc1Br ; Nc1ccc(OC2CCOCC2)cc1Br]

Intermediate 10, 4-(3-bromo-4-aminophenoxy)tetrahydro-2H-pyran (representative example of iron reduction reaction). 4-(3-bromo-4-nitrophenoxy)tetrahydro-2H-pyran was dissolved in ethanol/water 4/1, 10 eq. iron and 10 eq. $NH_4Cl$, and some drops of 2M HCl were added. The mixture wash heated at 50° C. for 1 h. The mixture was filtered over celite, the solids washed with MeOH and water. The filtrate was concentrated and then basified with NaOH 15% w/v. The aqueous layer was extracted with ethyl acetate, the combined organic layers dried over $Na_2SO_4$, filtered and concentrated under reduced pressure. The product was used without further purification.

Example 15

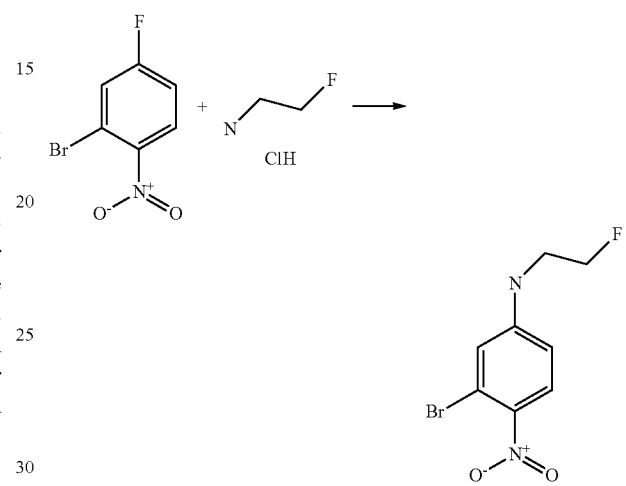

Intermediate 11, 3-bromo-N-(2-fluoroethyl)-4-nitroaniline. 2-bromo-4-fluoro-1-nitrobenzene and 1.5 eq. 2-fluoroethan-1-amine hydrochloride were dissolved in dry DMF followed by the addition of 2 eq. $K_2CO_3$. The mixture was stirred at 120° C. for 2 h. The mixture was diluted with water and extracted with ethyl acetate. The organic layer was dried, filtered and concentrated under reduced pressure. The crude product was purified by flash chromatography.

Example 16

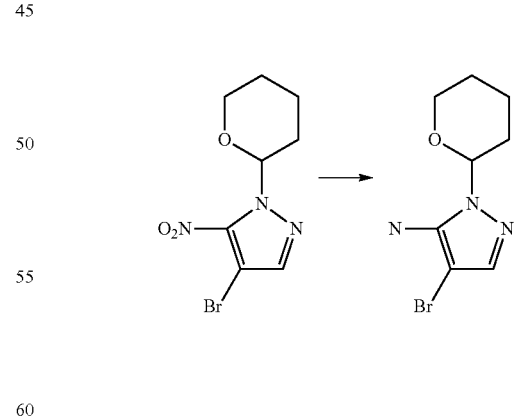

Intermediate 12, 4-bromo-1-(tetrahydro-2H-pyran-2-yl)-1H-pyrazol-5-amine. The title compound was synthesized according to the general protocol for iron reductions using 4-bromo-5-nitro-1-(tetrahydro-2H-pyran-2-yl)-1H-pyrazole as starting material.

Example 17

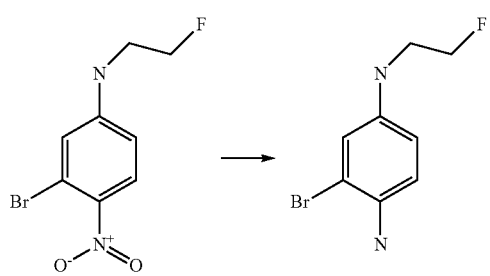 [SMILES: O=[N+]([O-])c1ccc(NCCF)cc1Br ; Nc1ccc(NCCF)cc1Br]

Intermediate 13, 3-bromo-N₁-(2-fluoroethyl)benzene-1,4-diamine. The title compound was synthesized according to the general protocol for iron reductions using 3-bromo-N-(2-fluoroethyl)-4-nitroaniline as starting material.

Example 18

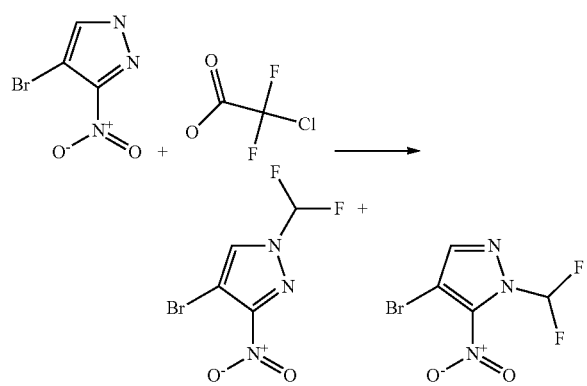

Intermediate 14, 4-bromo-1-(difluoromethyl)-3-nitro-1H-pyrazole and 4-bromo-1-(difluoromethyl)-5-nitro-1H-pyrazole. 4-bromo-3-nitro-1H-pyrazole was dissolved in DMF and water (4/1 v/v). 6 eq. $K_2CO_3$ and 1.2 eq. 2-chloro-2,2-difluoroacetic acid were added. The mixture was stirred at 120° C. o.n. Additional 1.2 eq. 2-chloro-2,2-difluoroacetic acid were added and the mixture was stirred for 3d at 120° C. The mixture was cooled to r.t., diluted with water and extracted with ethyl acetate. The organic layers were washed with NaOH 1M aq., water and brine, died over $Na_2SO_4$, filtered and concentrated under reduced pressure. The crude product was purified by flash chromatography. The isomers were used as mix for the next step.

Example 19

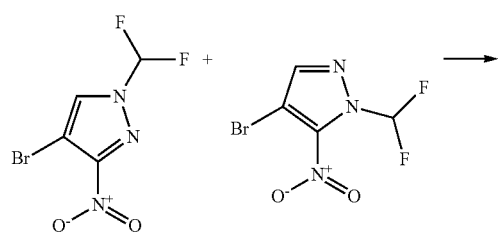

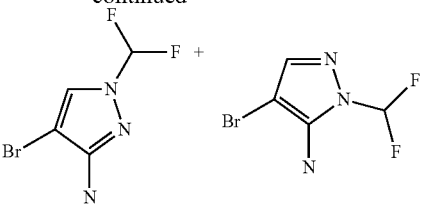

Intermediate 15, 4-bromo-1-(difluoromethyl)-1H-pyrazol-3-amine and 4-bromo-1-(difluoromethyl)-1H-pyrazol-5-amine. The title compounds were synthesized according to the general protocol for iron reductions using a mix of 4-bromo-1-(difluoromethyl)-3-nitro-1H-pyrazole and 4-bromo-1-(difluoromethyl)-5-nitro-1H-pyrazole as starting materials. The material was used as isomer mixture.

Example 20

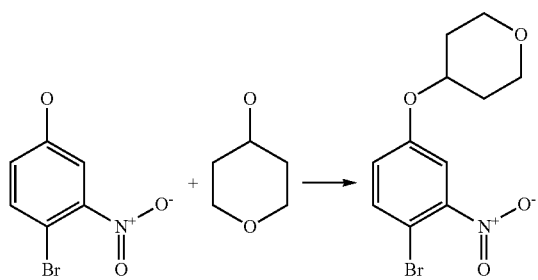

Intermediate 16, 4-(4-bromo-3-nitrophenoxy)tetrahydro-2H-pyran. 1 eq. tetrahydro-2H-pyran-4-ol, 4-bromo-3-nitrophenol and 2.6 eq. $PPh_3$ were dissolved in dry THF. The mixture was cooled to 0° C. and 2.3 eq. DBAD dissolved in dry THF was added slowly. The mixture was warmed to r.t. and stirred o.n. Additional 0.3 eq. tetrahydro-2H-pyran-4-ol, 0.3 eq. $PPh_3$, and DBAD were added and the mixture stirred for 4 h at r.t. TFA (20% v/v) was added and the mixture partitioned in between water and ethyl acetate. The organic layer was dried over $Na_2SO_4$, filtered and concentrated under reduced pressure. The crude product was purified by flash chromatography.

Example 21

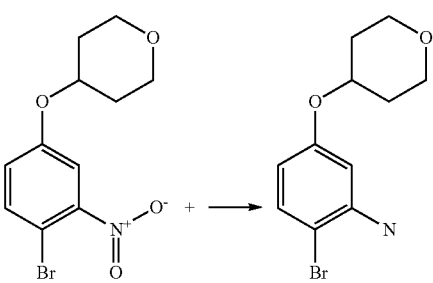 [SMILES: O=[N+]([O-])c1cc(OC2CCOCC2)ccc1Br ; Nc1cc(OC2CCOCC2)ccc1Br]

Intermediate 17, 2-bromo-5-((tetrahydro-2H-pyran-4-yl)oxy)aniline. The title compound was synthesized according to the general protocol for iron reductions using 4-(4-bromo-3-nitrophenoxy)tetrahydro-2H-pyran as starting material.

Example 22

General protocol for reductions using H2/Pd/C: The aromatic nitro compound is dissolved in ethanol. 0.05 eq. Pd, 10% w/w/ on charcoal, is added and the mixture stirred under a hydrogen atmosphere overnight. The mixture is filter over celite and the filtrate concentrated under reduced pressure. The product is used without further purification.

Example 23

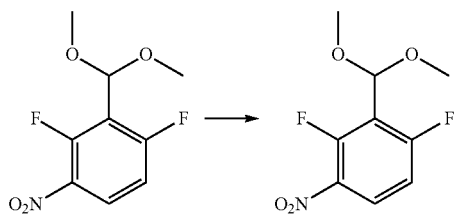 [SMILES: COC(OC)c1c(F)ccc([N+](=O)[O-])c1F ; COC(OC)c1c(F)ccc([N+](=O)[O-])c1F]

Intermediate 18, 3-(dimethoxymethyl)-2,4-difluoroaniline (representative example of H2/Pd/C reduction reaction). 2-(dimethoxymethyl)-1,3-difluoro-4-nitrobenzene was dissolved in ethanol, 0.05 eq. Pd/C (10% w/w) was added and the mixture was stirred at r.t. o.n. The mixture was filtered over celite and the filtrate concentrated under reduced pressure. The mixture was used without further purification.

Example 24

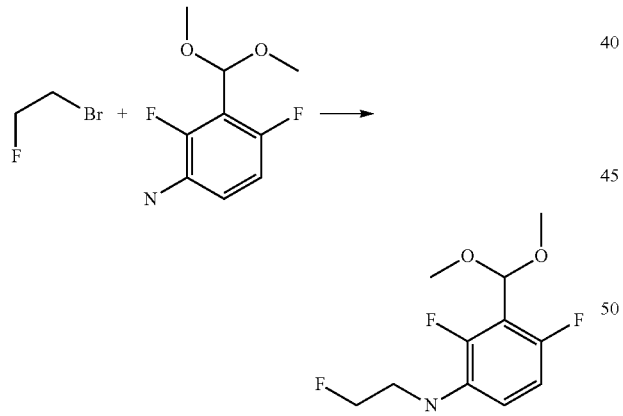

Intermediate 19, 3-(dimethoxymethyl)-2,4-difluoro-N-(2-fluoroethyl)aniline. 3-(dimethoxymethyl)-2,4-difluoroaniline, 1.2 eq. 1-bromo-2-fluoroethane, 2 eq. $Cs_2CO_3$, and 1.5 eq. DIPEA were dissolved in dry DMF. The mixture was heated under microwave conditions for 30 min 140° C. then for 30 min at 160° C., then, after addition of 1 eq. 1-bromo-2-fluoroethane again for 30 min at 160° C. The mixture was diluted with ethyl acetate, washed with water and brine, then dried over $Na_2SO_4$, filtered and concentrated under reduced pressure. The crude product was purified by flash chromatography.

Example 25

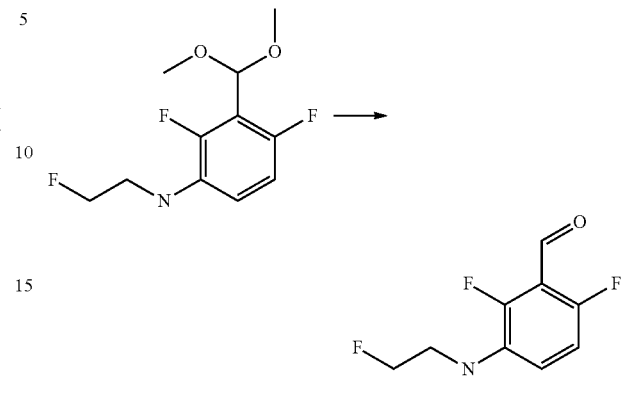

Intermediate 20, 2,6-difluoro-3-((2-fluoroethyl)amino)benzaldehyde. 3-(dimethoxymethyl)-2,4-difluoro-N-(2-fluoroethyl)aniline was dissolved in THF, 10% v/v of 6M HCl was added, and the mixture was stirred o.n. The mixture was basified with NaOH 6M aq. and extracted with ethyl acetate. The organic layer is washed with brine, dried over $Na_2SO_4$, filtered and concentrated under reduced pressure. The crude product was purified by flash chromatography.

Example 26

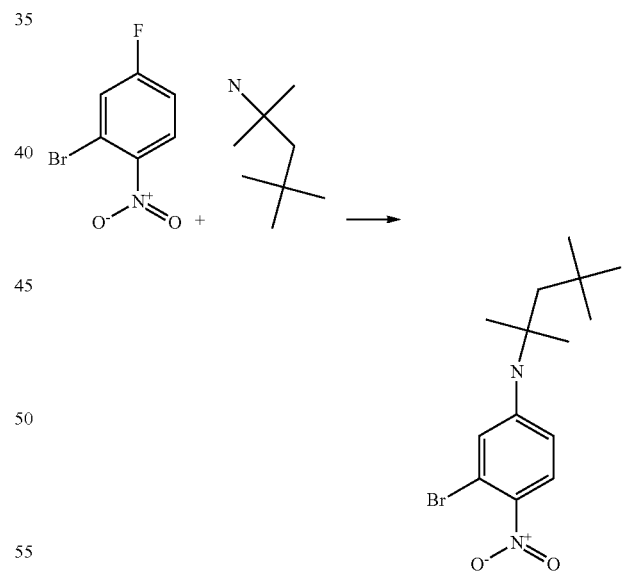

Intermediate 21, 3-bromo-4-nitro-N-(2,4,4-trimethylpentan-2-yl)aniline. 1.5 eq. 2-bromo-4-fluoro-1-nitrobenzene, 2,4,4-trimethylpentan-2-amine and 2 eq. $K_2CO_3$ are dissolved in DMF. The mixture is heated at 120° C. o.n. The reaction mixture is diluted with water and extracted with ethyl acetate. The organic layer is washed with brine, dried over $Na_2SO_4$, filtered and concentrated under reduced pressure. The crude reaction mixture is purified by flash chromatography.

Example 27

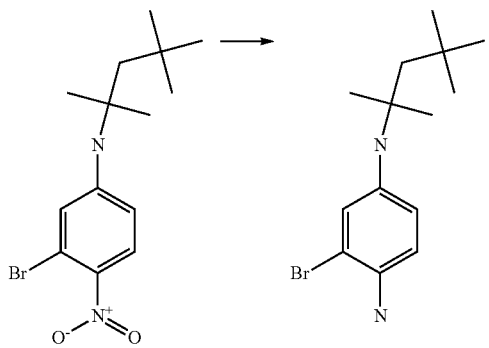 [SMILES: CC(C)(C)CC(C)(C)Nc1ccc([N+](=O)[O-])c(Br)c1 ; CC(C)(C)CC(C)(C)Nc1ccc(N)c(Br)c1]

Intermediate 22, 3-bromo-$N_1$-(2,4,4-trimethylpentan-2-yl)benzene-1,4-diamine. The title compound was synthesized according to the general protocol for iron reductions using 3-bromo-4-nitro-N-(2,4,4-trimethylpentan-2-yl)aniline as starting material.

Example 28

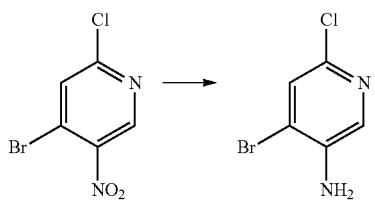 [SMILES: O=[N+]([O-])c1cnc(Cl)cc1Br ; Nc1cnc(Cl)cc1Br]

Intermediate 23, 4-bromo-6-chloropyridin-3-amine. The title compound was synthesized according to the general protocol for iron reductions using 4-bromo-2-chloro-5-nitropyridine as starting material.

Example 29

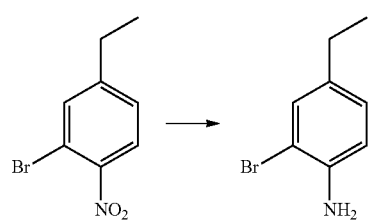

Intermediate 24, 2-bromo-4-ethyl-6-fluoroaniline 1-bromo-5-ethyl-3-fluoro-2-nitrobenzene. The title compound was synthesized according to the general protocol for iron reductions using 1-bromo-5-ethyl-3-fluoro-2-nitrobenzene as starting material.

Example 30

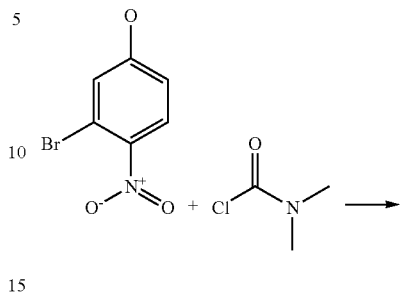

Intermediate 25, 3-bromo-4-nitrophenyl dimethylcarbamate. 3-bromo-4-nitrophenol was dissolved in dry acetonitrile 1.5 eq. $K_2CO_3$ solid and 1.2 eq. dimethylcarbamic chloride were added. The mixture was stirred at r.t. o.n. then 2 h at 100° C. The mixture was diluted with DCM, washed with brine, dried over $Na_2SO_4$, filtered and concentrated under reduced pressure. The crude product was purified by flash chromatography.

Example 31

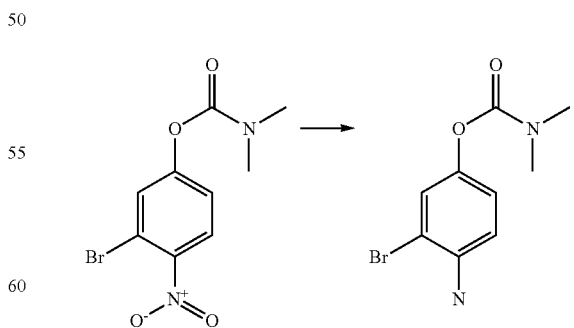

Intermediate 26, 4-amino-3-bromophenyl dimethylcarbamate. The title compound was synthesized according to the general protocol for iron reductions using 3-bromo-4-nitrophenyl dimethylcarbamate as starting material.

Example 32

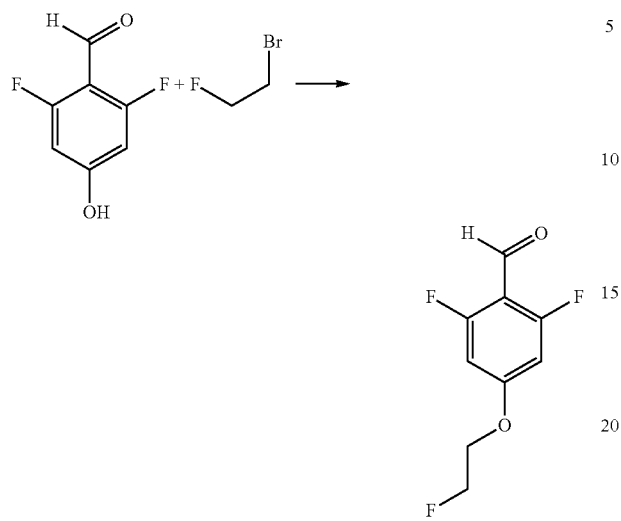

Intermediate 27, 2,6-difluoro-4-(2-fluoroethoxy)benzaldehyde. 2,6-difluoro-4-hydroxybenzaldehyde, 1.1 eq. 1-bromo-2-fluoroethane and 1.5 eq. K₂CO₃ were dissolved in dry DMF. The reaction was heated under microwave conditions for 5 min at 140° C. The heating was repeated after adding additional 0.5 eq. 1-bromo-2-fluoroethane. The mixture was diluted with water, extracted with ethyl acetate. The organic layer was washed with 2M HCl and water, dried over Na₂SO₄, filtered and concentrated under reduced pressure. The crude material was purified by flash chromatography.

Example 33

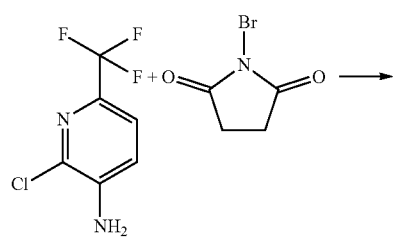

Intermediate 28, 4-bromo-2-chloro-6-trifluoromethyl-pyridin-3-ylamine. 2-Chloro-6-trifluoromethyl-pyridin-3-ylamine was dissolved in MeCN, and 1 eq. NBS was added. The mixture was heated to 80° C. for two hours. The mixture was cooled to r.t., then concentrated under reduced pressure and triturated with diethyl ether. The crude reaction mixture was purified by gradient flash chromatography.

Example 34

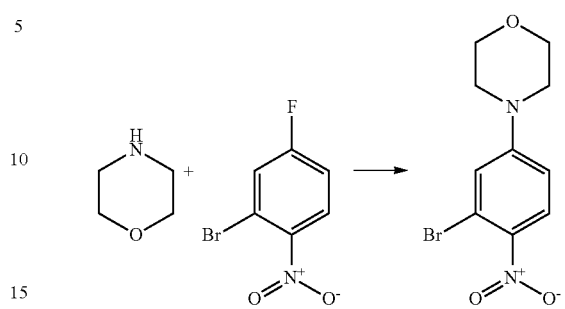

Intermediate 29, 4-(3-bromo-4-nitro-phenyl)-morpholine. 2-Bromo-4-fluoro-1-nitro-benzene was dissolved in DMF, and 1.3 eq. morpholine and 2 eq. K₂CO₃ were added. The mixture was stirred at r.t. over night. The mixture was diluted with water, extracted with ethyl acetate and DCM. The combined organics were dried, filtered, and concentrated under reduced pressure. The crude product was used without further purification.

Example 35

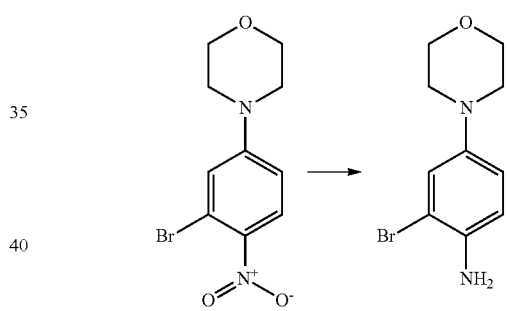

Intermediate 30, 4-(3-bromo-4-nitro-phenyl)-morpholine. The title compound was synthesized according to the general protocol for iron reductions using 4-(3-bromo-4-nitro-phenyl)-morpholine as starting material.

Example 36

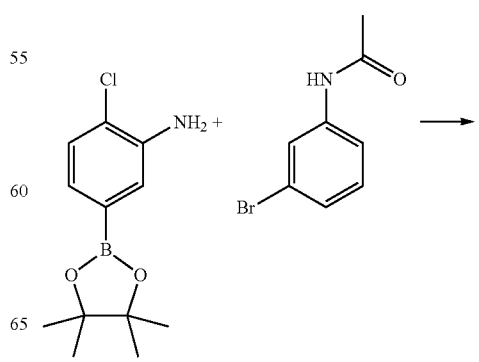

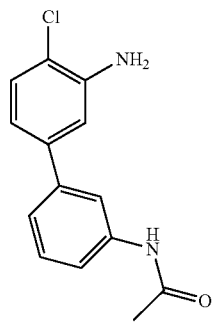

Intermediate 31, N-(3'-amino-4'-chloro-[1,1'-biphenyl]-3-yl)acetamide. 2-chloro-5-(4,4,5,5-tetramethyl-1,3,2-dioxaborolan-2-yl)aniline and 1 eq. N-(3-bromophenyl)acetamide were dissolved in dioxane, 0.1 eq. Pd dppf and 4 eq. 2M $Na_2CO_3$ in water were added. The mixture was heated under microwave conditions for 10 min at 135° C. The mixture was filtered over celite, washed with MeOH and water and concentrated under reduced pressure. The mixture was redissolved in DCM, washed with water dried over $Na_2SO_4$, filtered and concentrated under reduced pressure. The crude material was purified with gradient flash chromatography.

Example 37

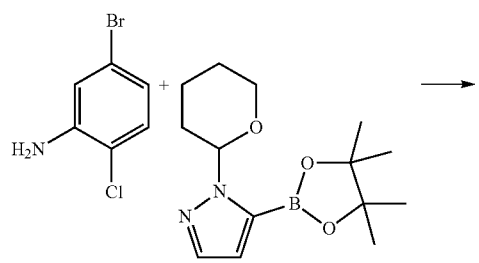

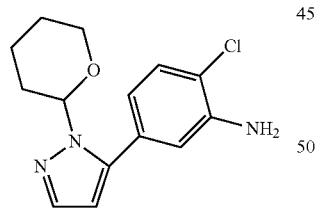

Intermediate 32, 2-chloro-5-(1-(tetrahydro-2H-pyran-2-yl)-1H-pyrazol-5-yl)aniline. 1-(tetrahydro-2H-pyran-2-yl)-5-(4,4,5,5-tetramethyl-1,3,2-dioxaborolan-2-yl)-1H-pyrazole and 1 eq. 5-bromo-2-chloroaniline were dissolved in dioxane, 0.1 eq. Pd dppf and 4 eq. 2M $Na_2CO_3$ in water were added. The mixture was heated under microwave conditions for 10 min at 135° C. The mixture was filtered through celite, washed with MeOH and water and concentrated under reduced pressure. The mixture was redissolved in DCM, washed with water dried over $Na_2SO_4$, filtered and concentrated under reduced pressure. The crude material was purified with gradient flash chromatography.

Example 38

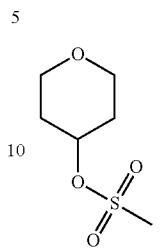

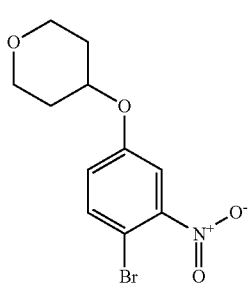

Intermediate 33, 4-(4-bromo-3-nitrophenoxy)tetrahydro-2H-pyran. Tetrahydro-2H-pyran-4-yl methanesulfonate and 1 eq. 4-bromo-3-nitrophenol were dissolved in dry DMF. 1.5 eq. $K_2CO_3$ were added. The mixture was heated under microwave irritation for 30 min at 150° C. The mixture was diluted with water and extracted with ethyl acetate. The organic layer was washed with 2M HCl, $NaHCO_3$, saturated aq. solution, and brine. The combined organic phase was dried over $Na_2SO_4$, filtered and concentrated under reduced pressure. The crude mixture was purified with gradient flash chromatography.

Example 39

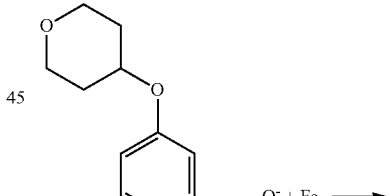

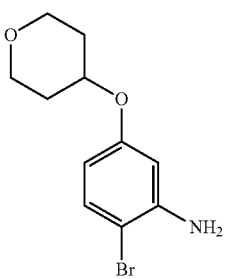

Intermediate 34, 2-bromo-5-((tetrahydro-2H-pyran-4-yl)oxy)aniline. The title compound was synthesized according to the general protocol for iron reductions using 4-(4-bromo-3-nitrophenoxy)tetrahydro-2H-pyran as starting material.

Example 40
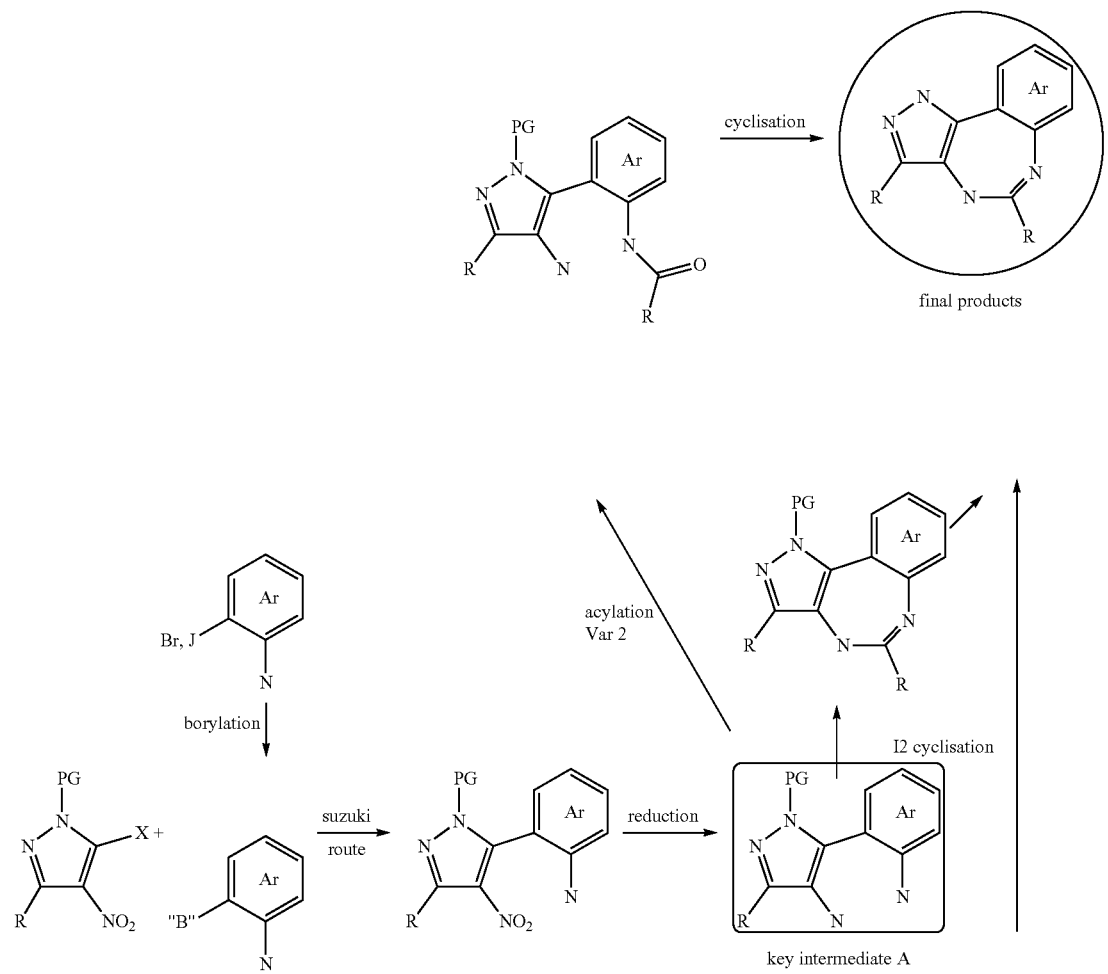
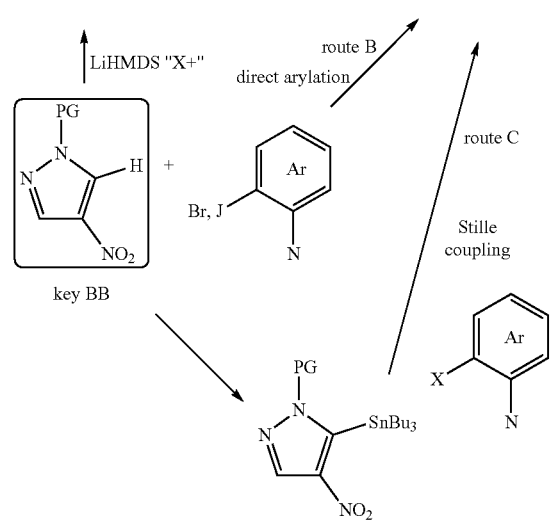
General routes to 1H-[1,3]Diazepine cpd class (7-Rings)

optionally substituted 5- or 6-member aryl or heteroaryl

R: H, Hal, Ar, Alk

PG: PMB, 2-THP

"B": B(OH)$_2$, Bpin

X+: C$_2$Cl$_6$, C$_2$Cl$_2$Br$_2$, I$_2$, ICl

General routes to 1H-[1,2]Diazepine compound class.

Example 41

Route A: Aryl-Aryl Bond Formation.

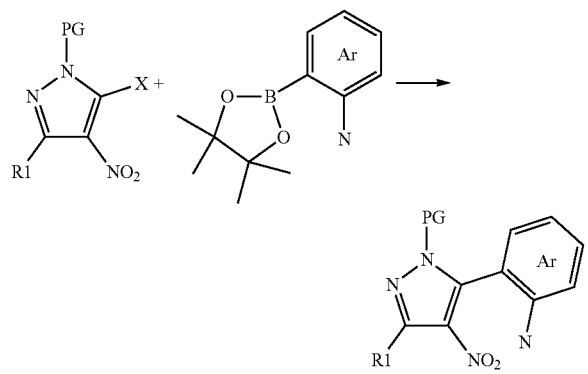

2-[4-Nitro-2-(tetrahydro-pyran-2-yl)-2H-pyrazol-3-yl]-phenylamine (representative example of Route A: Suzuki coupling from commercial boron esters or acids from commercial boron pinacolesters). 1 eq. 5-Chloro-4-nitro-1-(tetrahydro-pyran-2-yl)-1H-pyrazole was dissolved in dioxane followed by 1.2 eq. 2-(4,4,5,5-Tetramethyl-[1,3,2]dioxaborolan-2-yl)-phenylamine, 0.1 eq. Pd dppf, and 3 eq. 2M Na$_2$CO$_3$. The mixture was degassed with N$_2$ and heated at 80° C. o.n. The mixture was filtered over celite, washed with MeOH. The filtrate was extracted with DCM (3×). The combined organic phases were dried over Na$_2$SO$_4$ filtered and concentrated under reduced pressure. The crude product was purified by flash chromatography.

Example 42

Route B: Aryl-Aryl Bond Formation.

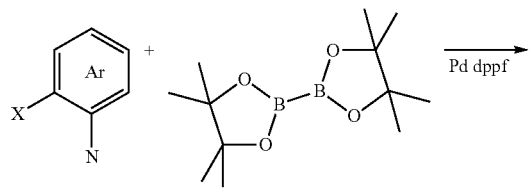

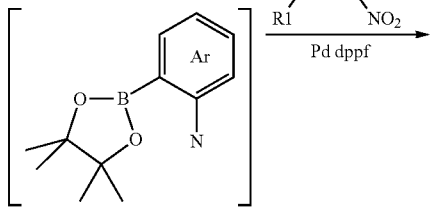

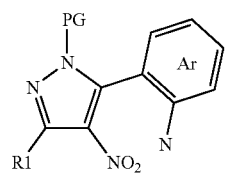

2-Methoxy-6-[4-nitro-2-(tetrahydro-pyran-2-yl)-2H-pyrazol-3-yl]-phenylamine (representative example of Route B: Sequential borylation/Suzuki coupling using 4,4,5,5,4',4',5',5'-Octamethyl-[2,2']bi[[1,3,2]dioxaborolanyl].
The two steps were performed in a "two step-one pot" reaction.). 1 eq. 2-Bromo-6-methoxy-phenylamine and 4 eq. potassium acetate were dissolved in dry dioxane, the mixture was degassed with N$_2$ then 0.1 eq. Pd dppf, after additional degassing with N$_2$, 2 eq. diborolan were added. This mixture was heated o.n. at 80° C. 0.8 eq. 5-Chloro-4-nitro-1-(tetrahydro-pyran-2-yl)-1H-pyrazole and 3 eq. 2M Na$_2$CO$_3$ were added to this mixture. The mixture was flushed with N$_2$ again, before adding additional 0.05 eq. Pd dppf. The mixture was stirred at 80° C. o.n. The reaction mixture was filtered over celite, the solids were washed with MeOH. The filtrate was concentrated under reduced pressure, diluted with water and extracted with ethyl acetate 3×. The combined organics were dried over Na$_2$SO$_4$, filtered and concentrated under reduced pressure. The crude product was purified by flash chromatography.

Example 43

Route C: Aryl-Aryl Bond Formation.

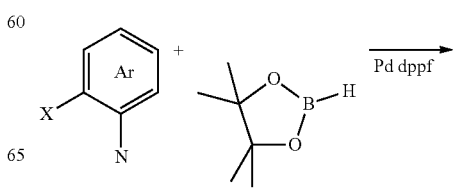

-continued

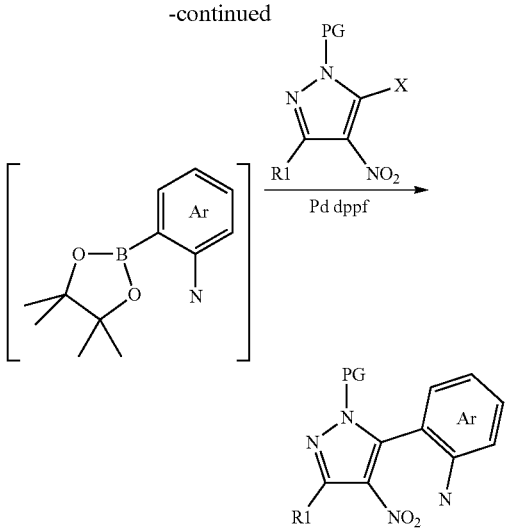

3-Methoxy-2-[4-nitro-2-(tetrahydro-pyran-2-yl)-2H-pyrazol-3-yl]-phenylamine (representative example of Route C: Stille coupling using 4,4,5,5-Tetramethyl-[1,3,2] dioxaborolane). 1 eq. 2-Bromo-3-methoxy-phenylamine and 3 eq. triethylamine were dissolved in dry dioxane. The mixture was flushed with N₂, then 0.1 eq. Pd dppf and after additional degassing with N₂, 3 eq. pinacolboran were added. This mixture was heated for 2 h under microwave conditions at 140° C. 0.8 eq. 5-chloro-4-nitro-1-(tetrahydro-pyran-2-yl)-1H-pyrazole and 3 eq. 2M Na₂CO₃ solution were added to this mixture. The mixture was flushed with N₂ again, before adding additional 0.1 eq. Pd dppf. The mixture was stirred at 80° C. o.n. The reaction mixture was filtered over celite, the solids were washed with MeOH. The filtrate was concentrated under reduced pressure, dilute with water and extracted with DCM 3×. The combined organics were dried over Na₂SO₄, filtered and concentrated under reduced pressure. The crude product was purified by flash chromatography.

Example 44

Route D: Aryl-Aryl Bond Formation.

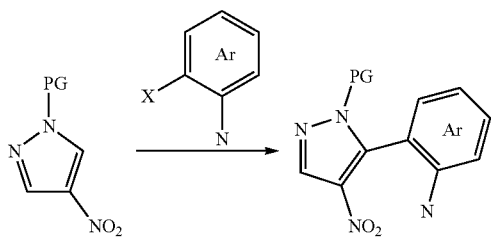

6-Methoxy-2-[2-(4-methoxy-benzyl)-4-nitro-2H-pyrazol-3-yl]-pyridin-3-ylamine (representative example of Route D: Direct arylation). 4-Nitro-1-(4-methoxy-benzyl)-1H-pyrazole, 1 eq. 2-bromo-6-methoxy-pyridin-3-ylamine, 0.3 eq. pivalic acid and 3 eq. K₂CO₃ were dissolved in dry DMF. The mixture was degassed with N₂, followed by the addition of 0.15 eq. catacxiumA and Pd(OAc)₂. The mixture was degassed and stirred o.n. at 115° C. The mixture was filtered over celite and the solids washed with methanol. After concentration under reduced pressure the mixture was diluted with water and extracted with DCM. The combined organic layers were washed with brine, dried over Na₂SO₄, filtered and concentrated under reduced pressure. The crude product was purified by flash chromatography.

Example 45

Route E: Hydrogenation.

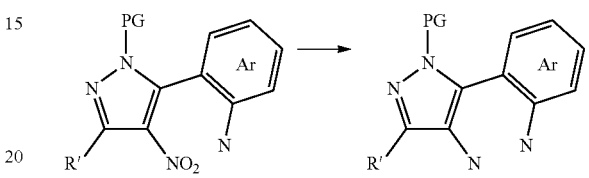

5-(2-Amino-5-methyl-phenyl)-1-(tetrahydro-pyran-2-yl)-1H-pyrazol-4-ylamine (representative example of Route E: hydrogenation). 4-Methyl-2-[4-nitro-2-(tetrahydro-pyran-2-yl)-2H-pyrazol-3-yl]-phenylamine was dissolved in methanol, 0.07 eq. Pd/C, 10% w/w, were added. The mixture was stirred at r.t. Under a hydrogen atmosphere (balloon) for 5 h. The mixture was filtered through celite, the solids washed with MeOH. The filtrate was concentrated under reduced pressure to yield the title product. It was used without further purification.

Example 46

Route F: Basic Hydrogenation.

4-(4-amino-1-(4-methoxybenzyl)-1H-pyrazol-5-yl)-6-(trifluoromethyl)pyridin-3-amine (representative example of Route F: basic hydrogenation). 2-chloro-4-(1-(4-methoxybenzyl)-4-nitro-1H-pyrazol-5-yl)-6-(trifluoromethyl)pyridin-3-amine was dissolved in 32 mL of dry iPrOH. The system was evacuated and backfilled with N₂ 3 times. Then 1.2 eq. triethylamine and 1 eq. Pd on charcoal (10% w) were quickly added. The mixture was stirred under hydrogen atmosphere (balloon) at r.t overnight. The mixture was filtered over celite and washed well with MeOH. The filtrate was then concentrated under reduced pressure. The material was used without further purification.

Example 47

Route G: Reduction with Iron.

5-(2-Amino-6-methoxy-phenyl)-1-(tetrahydro-pyran-2-yl)-1H-pyrazol-4-ylamine (representative example of Method G: reduction with iron). 3-Methoxy-2-[4-nitro-2-(tetrahydro-pyran-2-yl)-2H-pyrazol-3-yl]-phenylamine was dissolved in ethanol/water 10/4 v/v, 10 eq. iron and NH₄Cl and some drops 2M HCl were added. The mixture was heated at 50° C. for 1 h. The mixture was filtered through celite, the solids were washed with MeOH and water. The mixture was concentrated, basified with NaOH, 15% w/v aq. solution, to pH 10 and extracted with ethyl acetate 3×. The combined organic layers were washed with brine, dried over Na₂SO₄, filtered and concentrated under reduced pressure. The crude product was used without further purification.

Example 48

Procedure for Cyclization/Deprotection Using the Described Aryl-Aryl Diamines and Corresponding Aldehydes.

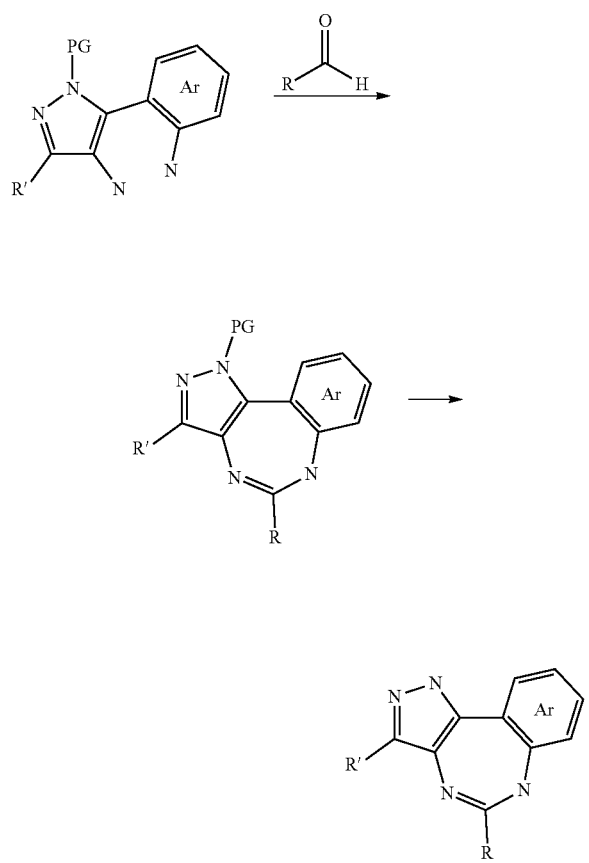

Example 49

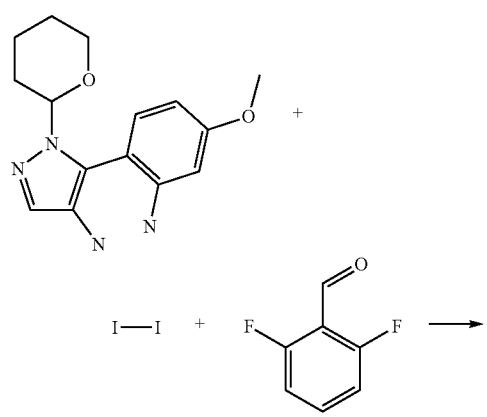

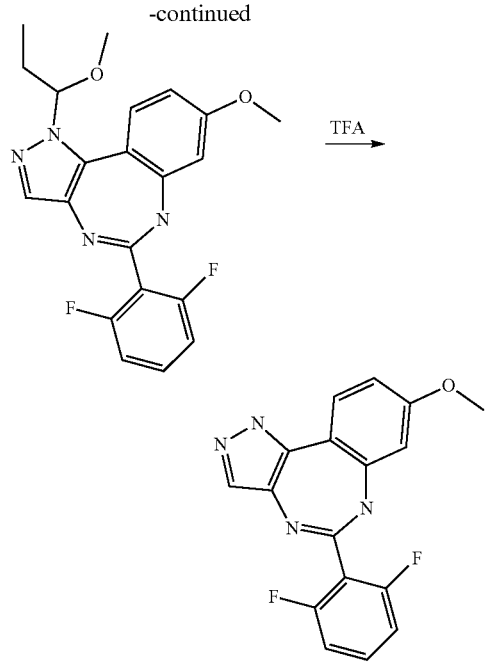

5-(2,6-difluorophenyl)-8-methoxy-1,4-dihydrobenzo[d]pyrazolo[3,4-f][1,3]diazepine from 5-(2,6-difluorophenyl)-8-methoxy-1-(tetrahydro-2H-pyran-2-yl)-1,4-dihydrobenzo[d]pyrazolo[3,4-f][1,3]diazepine. 5-(2-amino-4-methoxyphenyl)-1-(tetrahydro-2H-pyran-2-yl)-1H-pyrazol-4-amine and 1 eq. 2,6-difluoro-benzaldehyde were dissolved in tert.-butanol. 3 eq. iodine and 3 eq. K₂CO₃ were added. The mixture was stirred o.n. at r.t. A Na₂S₂O₃ 5% w/v aq. solution was added. After stirring for 30 min the solution was diluted with water and extracted with DCM. The organic layer was evaporated. The product was used in the following step without further purification. The product of the step above was dissolved in TFA. The mixture was stirred at r.t. for 3 h. The mixture was concentrated under reduced pressure and purified by SEMIprep reversed phase chromatography Example 50

The following HPLC Methods were used:
Method: HPLC-MS A
  col: 'Waters ACQUITY UPLC HSS T3 50×2.1 1.8 μm PN:186003538'
  grad: '2%-4.0 min->95%-1.0 min->95%-0.1 min->2%-2.9 min->2%; ACN/H2O+0.1% HCOOH'
  flow: '0.6 mL/min'
  ms: 'ESI positiv & negativ'
Method: HPLC-MS B
  col: 'Waters ACQUITY UPLC CSH C18 50×2.1 1.7 μm PN:186005296'
  grad: '5%-4.0 min->95%-1.0 min->95%-0.1 min->5%-2.9 min->5%; ACN/H2O+0.1% HCOOH'
  flow: '0.6 mL/min'
  ms: 'ESI positiv and negativ'
Method: HPLC-MS C
  col: 'Waters ACQUITY UPLC CSH C18 50×2.1 1.7 μm PN:186005296' grad: '4%-4.0 min->96%-1.0 min->96%-0.1 min->4%-2.9 min->4%; ACN/H2O+1 mM NH₄Ac-Buffer pH 9.2'
Method: HPLC-MS D
col: 'Waters CORTECS UPLC C18+50×2.1 1.6 μm PN:186007114'
grad: '5%-4.0 min->95%-1.0 min->95%-0.1 min->5%-2.9 min->5%; ACN/H2O+0.1% HCOOH'
flow: '0.6 mL/min'
ms: 'ESI positiv & negativ'

Method: HPLC-MS E
col: 'Waters ACQUITY UPLC CSH C18 50×2.1 1.7 m PN:186005296'
grad: '5%-0.75 min->95%-0.5 min->95%-0.05 min->5%-1.2 min->5%; ACN/H2O+0.1% HCOOH'
flow: '1.2 mL/min'
ms: 'ESI positiv'

The products listed in Table 3 were synthesized according to the cyclization/deprotection method.

TABLE 3

| Compound-No | IUPAC-Name | HPLC-MS-Method | retention time (min) | m + H Found |
|---|---|---|---|---|
| Compound 1 | 5-phenyl-1,6-dihydrobenzo[d]pyrazolo[3,4-f][1,3]diazepine | HPLC-MS A | 2.52 | 261.0 |
| Compound 2 | 5-(pyridin-2-yl)-1,6-dihydrobenzo[d]pyrazolo[3,4-f][1,3]diazepine | HPLC-MS B | 2.29 | 262.0 |
| Compound 3 | 5-(2-methoxyphenyl)-1,6-dihydrobenzo[d]pyrazolo[3,4-f][1,3]diazepine | HPLC-MS B | 2.11 | 291.0 |
| Compound 4 | 5-(furan-2-yl)-1,6-dihydrobenzo[d]pyrazolo[3,4-f][1,3]diazepine | HPLC-MS C | 2.77 | 251.0 |
| Compound 5 | 5-(furan-3-yl)-1,6-dihydrobenzo[d]pyrazolo[3,4-f][1,3]diazepine | HPLC-MS A | 2.36 | 251.0 |
| Compound 6 | 5-(thiophen-2-yl)-1,6-dihydrobenzo[d]pyrazolo[3,4-f][1,3]diazepine | HPLC-MS C | 3.07 | 267.0 |
| Compound 7 | 5-(1-methyl-1H-pyrazol-3-yl)-1,6-dihydrobenzo[d]pyrazolo[3,4-f][1,3]diazepine | HPLC-MS A | 2.23 | 265.0 |
| Compound 8 | 5-(2,6-difluorophenyl)-1,6-dihydrobenzo[d]pyrazolo[3,4-f][1,3]diazepine | HPLC-MS A | 2.51 | 297.0 |
| Compound 9 | 5-(2-(trifluoromethyl)phenyl)-1,6-dihydrobenzo[d]pyrazolo[3,4-f][1,3]diazepine | HPLC-MS A | 2.80 | 329.0 |
| Compound 10 | 5-phenyl-1,4-dihydropyrazolo[4,3-d]pyrido[3,2-f][1,3]diazepine | HPLC-MS C | 2.95 | 262.0 |
| Compound 11 | 5-(2,6-difluorophenyl)-1,4-dihydropyrazolo[4,3-d]pyrido[3,2-f][1,3]diazepine | HPLC-MS B | 2.62 | 298.0 |
| Compound 12 | 5-(2-methoxyphenyl)-1,4-dihydropyrazolo[4,3-d]pyrido[3,2-f][1,3]diazepine | HPLC-MS A | 2.50 | 292.0 |
| Compound 13 | 3-(1,4-dihydrobenzo[d]pyrazolo[3,4-f][1,3]diazepin-5-yl)-2,4-difluorobenzonitrile | HPLC-MS A | 2.92 | 322.0 |
| Compound 14 | 3-(1,4-dihydropyrazolo[4,3-d]pyrido[3,2-f][1,3]diazepin-5-yl)-2,4-difluorobenzonitrile | HPLC-MS A | 2.89 | 323.2 |
| Compound 15 | 2-(1,4-dihydropyrazolo[4,3-d]pyrido[3,2-f][1,3]diazepin-5-yl)benzoic acid | HPLC-MS A | 2.35 | 306.1 |
| Compound 16 | 5-(4-bromo-1H-pyrazol-3-yl)-1,4-dihydrobenzo[d]pyrazolo[3,4-f][1,3]diazepine | HPLC-MS A | 2.22 | 329.0 |
| Compound 17 | 5-(3-fluoropyridin-2-yl)-1,6-dihydrobenzo[d]pyrazolo[3,4-f][1,3]diazepine | HPLC-MS A | 2.49 | 280.1 |
| Compound 18 | 5-(3-chloro-2,6-difluorophenyl)-1,4-dihydrobenzo[d]pyrazolo[3,4-f][1,3]diazepine | HPLC-MS A | 3.00 | 331.0 |
| Compound 19 | 2-(1,6-dihydrobenzo[d]pyrazolo[3,4-f][1,3]diazepin-5-yl)benzoic acid | HPLC-MS A | 2.39 | 305.0 |
| Compound 20 | 5-(4-bromo-1-methyl-1H-pyrazol-5-yl)-1,4-dihydrobenzo[d]pyrazolo[3,4-f][1,3]diazepine | HPLC-MS C | 2.99 | 343.0 |
| Compound 21 | 5-(4-bromo-1-methyl-1H-pyrazol-3-yl)-1,4-dihydrobenzo[d]pyrazolo[3,4-f][1,3]diazepine | HPLC-MS A | 2.54 | 343.0 |
| Compound 22 | 5-(1H-pyrrolo[2,3-b]pyridin-3-yl)-1,4-dihydrobenzo[d]pyrazolo[3,4-f][1,3]diazepine | HPLC-MS C | 2.35 | 301.2 |
| Compound 23 | 5-(1H-indazol-3-yl)-1,4-dihydrobenzo[d]pyrazolo[3,4-f][1,3]diazepine | HPLC-MS A | 2.71 | 301.2 |
| Compound 24 | 5-(3-fluoropyridin-4-yl)-1,6-dihydrobenzo[d]pyrazolo[3,4-f][1,3]diazepine | HPLC-MS C | 2.72 | 280.1 |
| Compound 25 | 9-chloro-5-(2,6-difluorophenyl)-1,4-dihydrobenzo[d]pyrazolo[3,4-f][1,3]diazepine | HPLC-MS A | 3.01 | 331.0 |
| Compound 26 | 2-(9-chloro-1,4-dihydrobenzo[d]pyrazolo[3,4-f][1,3]diazepin-5-yl)benzoic acid | HPLC-MS A | 2.67 | 339.0 |
| Compound 27 | 5-(2-chloro-6-fluorophenyl)-1,4-dihydrobenzo[d]pyrazolo[3,4-f][1,3]diazepine | HPLC-MS A | 2.70 | 313.0 |
| Compound 28 | 3-(1,4-dihydrobenzo[d]pyrazolo[3,4-f][1,3]diazepin-5-yl)pyridin-2(1H)-one | HPLC-MS A | 2.33 | 278.1 |
| Compound 29 | 5-(3-chloro-2,6-difluorophenyl)-1,4-dihydropyrazolo[4,3-d]pyrido[3,2-f][1,3]diazepine | HPLC-MS A | 3.09 | 332.0 |
| Compound 30 | 5-(2-chloro-6-fluorophenyl)-1,4-dihydropyrazolo[4,3-d]pyrido[3,2-f][1,3]diazepine | HPLC-MS A | 2.76 | 314.0 |
| Compound 31 | 5-(2,3,6-trifluorophenyl)-1,4-dihydropyrazolo[4,3-d]pyrido[3,2-f][1,3]diazepine | HPLC-MS A | 2.88 | 316.0 |
| Compound 32 | 5-(2,3,6-trifluorophenyl)-1,4-dihydrobenzo[d]pyrazolo[3,4-f][1,3]diazepine | HPLC-MS A | 2.80 | 315.0 |
| Compound 33 | 5-(2,6-difluorophenyl)-9-fluoro-1,6-dihydrobenzo[d]pyrazolo[3,4-f][1,3]diazepine | HPLC-MS B | 2.32 | 315.0 |
| Compound 34 | 5-(2-chloro-6-fluorophenyl)-9-fluoro-1,6-dihydrobenzo[d]pyrazolo[3,4-f][1,3]diazepine | HPLC-MS B | 2.48 | 331.0 |
| Compound 35 | 5-(2-chloro-6-fluorophenyl)-9-methyl-1,6-dihydrobenzo[d]pyrazolo[3,4-f][1,3]diazepine | HPLC-MS B | 2.50 | 327.0 |
| Compound 36 | 5-(2,6-difluorophenyl)-9-methyl-1,6-dihydrobenzo[d]pyrazolo[3,4-f][1,3]diazepine | HPLC-MS B | 2.38 | 311.2 |
| Compound 37 | 9-chloro-5-(2-chloro-6-fluorophenyl)-1,4-dihydrobenzo[d]pyrazolo[3,4-f][1,3]diazepine | HPLC-MS B | 2.83 | 348.0 |
| Compound 38 | 5-(2,6-difluorophenyl)-9-methoxy-1,6-dihydrobenzo[d]pyrazolo[3,4-f][1,3]diazepine | HPLC-MS A | 2.72 | 327.2 |
| Compound 39 | 5-(2-chloro-6-fluorophenyl)-9-methoxy-1,6-dihydrobenzo[d]pyrazolo[3,4-f][1,3]diazepine | HPLC-MS A | 2.80 | 343.2 |
| Compound 40 | 5-(2,6-difluorophenyl)-9-(trifluoromethoxy)-1,6-dihydrobenzo[d]pyrazolo[3,4-f][1,3]diazepine | HPLC-MS B | 3.02 | 381.0 |
| Compound 41 | 5-(2-chloro-6-fluorophenyl)-9-(trifluoromethoxy)-1,6-dihydrobenzo[d]pyrazolo[3,4-f][1,3]diazepine | HPLC-MS B | 3.18 | 397.0 |
| Compound 42 | 9-(difluoromethoxy)-5-(2,6-difluorophenyl)-1,6-dihydrobenzo[d]pyrazolo[3,4-f][1,3]diazepine | HPLC-MS B | 2.60 | 363.0 |
| Compound 43 | 5-(2-chloro-6-fluorophenyl)-9-(difluoromethoxy)-1,6-dihydrobenzo[d]pyrazolo[3,4-f][1,3]diazepine | HPLC-MS B | 2.70 | 379.0 |
| Compound 44 | 5-(2,6-difluorophenyl)-9-ethyl-1,6-dihydrobenzo[d]pyrazolo[3,4-f][1,3]diazepine | HPLC-MS B | 2.60 | 325.2 |
| Compound 45 | 5-(2-chloro-6-fluorophenyl)-9-ethyl-1,6-dihydrobenzo[d]pyrazolo[3,4-f][1,3]diazepine | HPLC-MS B | 2.71 | 341.2 |
| Compound 46 | 5-(2,6-difluorophenyl)-9-(trifluoromethyl)-1,6-dihydrobenzo[d]pyrazolo[3,4-f][1,3]diazepine | HPLC-MS B | 3.16 | 365.2 |
| Compound 47 | 5-(2-chloro-6-fluorophenyl)-9-(trifluoromethyl)-1,6-dihydrobenzo[d]pyrazolo[3,4-f][1,3]diazepine | HPLC-MS B | 3.34 | 381.0 |
| Compound 48 | 5-(2,6-difluorophenyl)-7-methoxy-1,6-dihydrobenzo[d]pyrazolo[3,4-f][1,3]diazepine | HPLC-MS C | 3.24 | 327.2 |
| Compound 49 | 5-(2,6-difluorophenyl)-8-methoxy-1,4-dihydrobenzo[d]pyrazolo[3,4-f][1,3]diazepine | HPLC-MS A | 2.74 | 327.0 |
| Compound 50 | (5-(2,6-difluorophenyl)-1,6-dihydrobenzo[d]pyrazolo[3,4-f][1,3]diazepin-9-yl)methanol | HPLC-MS B | 1.82 | 327.0 |
| Compound 51 | 5-(2,6-difluorophenyl)-9-(fluoromethyl)-1,6-dihydrobenzo[d]pyrazolo[3,4-f][1,3]diazepine | HPLC-MS C | 2.96 | 329.0 |
| Compound 52 | 5-(2,6-difluorophenyl)-8-methyl-4,8-dihydro-1H-dipyrazolo[3,4-d:3',4'-f][1,3]diazepine | HPLC-MS A | 2.25 | 300.0 |
| Compound 53 | 5-(2,6-difluorophenyl)-1,4-dihydropyrazolo[4,3-d]pyrido[3,4-f][1,3]diazepine | HPLC-MS C | 1.96 | 298.0 |
| Compound 54 | 5-(2,6-difluorophenyl)-10-methoxy-1,4-dihydrobenzo[d]pyrazolo[3,4-f][1,3]diazepine | HPLC-MS C | 2.94 | 327.0 |
| Compound 55 | 5-(2,6-difluorophenyl)-9-methoxy-1,4-dihydropyrazolo[4,3-d]pyrido[2,3-f][1,3]diazepine | HPLC-MS A | 3.17 | 328.0 |

TABLE 3-continued

| Compound-No | IUPAC-Name | HPLC-MS-Method | retention time (min) | m + H Found |
|---|---|---|---|---|
| Compound 56 | (5-(2,6-difluorophenyl)-1,4-dihydrobenzo[d]pyrazolo[3,4-f][1,3]diazepin-8-yl)(morpholino)methanone | HPLC-MS A | 2.49 | 410.2 |
| Compound 57 | 5-(2,6-difluorophenyl)-1,6-dihydropyrazolo[4,3-d]pyrido[2,3-f][1,3]diazepine | HPLC-MS A | 2.43 | 298.0 |
| Compound 58 | 5-(2,6-difluorophenyl)-N-(tetrahydro-2H-pyran-4-yl)-1,4-dihydrobenzo[d]pyrazolo[3,4-f][1,3]diazepine-8-carboxamide | HPLC-MS A | 2.46 | 314.0 |
| Compound 59 | 5-(2,6-difluorophenyl)-8-isopropyl-4,8-dihydro-1H-dipyrazolo[3,4-d:3',4'-f][1,3]diazepine | HPLC-MS B | 2.15 | 392.2 |
| Compound 60 | 5-(2,6-difluorophenyl)-8-(tetrahydro-2H-pyran-4-yl)-6,8-dihydro-1H-dipyrazolo[3,4-d:3',4'-f][1,3]diazepine | HPLC-MS C | 2.63 | 371.0 |
| Compound 61 | 5-(2,6-difluorophenyl)-9-methyl-1,6-dihydropyrazolo[4,3-d]pyrido[3,2-f][1,3]diazepine | HPLC-MS B | 2.41 | 312.0 |
| Compound 62 | 9-methyl-5-phenyl-1,6-dihydropyrazolo[4,3-d]pyrido[3,2-f][1,3]diazepine | HPLC-MS C | 3.10 | 276.1 |
| Compound 63 | 5-(2,6-difluorophenyl)-9-(trifluoromethyl)-1,6-dihydropyrazolo[4,3-d]pyrido[3,2-f][1,3]diazepine | HPLC-MS B | 3.48 | 366.0 |
| Compound 64 | 9-chloro-5-(2,6-difluorophenyl)-1,6-dihydropyrazolo[4,3-d]pyrido[3,2-f][1,3]diazepine | HPLC-MS B | 3.08 | 332.0 |
| Compound 65 | 8-(difluoromethyl)-5-(2,6-difluorophenyl)-4,8-dihydro-1H-dipyrazolo[3,4-d:3',4'-f][1,3]diazepine | HPLC-MS A | 2.60 | 337.0 |
| Compound 66 | 5-(2,6-difluorophenyl)-4,9-dihydro-1H-dipyrazolo[4,3-d:3',4'-f][1,3]diazepine | HPLC-MS A | 2.04 | 287.0 |
| Compound 67 | 5-(2,6-difluorophenyl)-9-(3,6-dihydro-2H-pyran-4-yl)-1,6-dihydropyrazolo[4,3-d]pyrido[3,2-f][1,3]diazepine | HPLC-MS B | 2.74 | 380.0 |
| Compound 68 | 5-(2,6-difluorophenyl)-8-phenyl-6,8-dihydro-1H-dipyrazolo[3,4-d:3',4'-f][1,3]diazepine | HPLC-MS C | 3.32 | 363.0 |
| Compound 69 | 3-bromo-5-(2,6-difluorophenyl)-1,6-dihydrobenzo[d]pyrazolo[3,4-f][1,3]diazepine | HPLC-MS C | 3.44 | 374.8 |
| Compound 70 | 7-(difluoromethyl)-5-(2,6-difluorophenyl)-4,7-dihydro-1H-dipyrazolo[3,4-d:3',4'-f][1,3]diazepine | HPLC-MS C | 2.60 | 337.0 |
| Compound 71 | 5-(2,6-difluorophenyl)-1,4-dihydropyrazolo[4,3-d]pyrido[4,3-f][1,3]diazepine | HPLC-MS C | 2.54 | 298.0 |
| Compound 72 | 5-(2,6-difluorophenyl)-6,7-dihydro-1H-dipyrazolo[3,4-d:3',4'-f][1,3]diazepine | HPLC-MS C | 2.11 | 287.0 |
| Compound 73 | 5-(2,6-difluorophenyl)-1,4-dihydrobenzo[d]pyrazolo[3,4-f][1,3]diazepine-8-carboxylic acid | HPLC-MS C | 2.23 | 341.0 |
| Compound 74 | 8-(tert-butyl)-5-(2,6-difluorophenyl)-4,8-dihydro-1H-dipyrazolo[3,4-d:3',4'-f][1,3]diazepine | HPLC-MS C | 3.10 | 343.2 |
| Compound 75 | 5-(2,6-difluorophenyl)-1,6-dihydropyrazolo[4,3-d]pyrido[3,2-f][1,3]diazepine-9-carbonitrile | HPLC-MS B | #N/A | 323.0 |
| Compound 76 | 5-(2,6-difluorophenyl)-3-methyl-1,4-dihydrobenzo[d]pyrazolo[3,4-f][1,3]diazepine | HPLC-MS C | 3.19 | 310.8 |
| Compound 77 | 5-(2,6-difluorophenyl)-8,9-dimethoxy-1,6-dihydrobenzo[d]pyrazolo[3,4-f][1,3]diazepine | HPLC-MS A | 2.67 | 357.2 |
| Compound 78 | (5-(2-chloro-6-fluorophenyl)-1,4-dihydrobenzo[d]pyrazolo[3,4-f][1,3]diazepin-8-yl)(morpholino)methanone | HPLC-MS A | 2.57 | 426.2 |
| Compound 79 | (5-(2,6-dichlorophenyl)-1,4-dihydrobenzo[d]pyrazolo[3,4-f][1,3]diazepin-8-yl)(morpholino)methanone | HPLC-MS A | 2.64 | 443.2 |
| Compound 80 | morpholino(5-(3-(trifluoromethyl)pyridin-2-yl)-2,4-dihydrobenzo[d]pyrazolo[3,4-f][1,3]diazepin-8-yl)methanone | HPLC-MS A | 2.66 | 443.2 |
| Compound 81 | 5-(2,6-difluorophenyl)-1,4-dihydrobenzo[d]pyrazolo[3,4-f][1,3]diazepine-8-carboxamide | HPLC-MS C | 2.37 | 340.0 |
| Compound 82 | (5-(2,6-difluorophenyl)-1,6-dihydrobenzo[d]pyrazolo[3,4-f][1,3]diazepin-9-yl)(morpholino)methanone | HPLC-MS C | 2.51 | 410.2 |
| Compound 83 | (5-(2-chloro-6-fluorophenyl)-1,6-dihydrobenzo[d]pyrazolo[3,4-f][1,3]diazepin-9-yl)(morpholino)methanone | HPLC-MS C | 2.61 | 426.2 |
| Compound 84 | 5-(2-chloro-6-fluorophenyl)-8-isopropyl-4,8-dihydro-1H-dipyrazolo[3,4-d:3',4'-f][1,3]diazepine | HPLC-MS A | 2.69 | 345.0 |
| Compound 85 | N-(5-(2,6-difluorophenyl)-1,6-dihydropyrazolo[4,3-d]pyrido[3,2-f][1,3]diazepin-9-yl)acetamide | HPLC-MS B | 2.41 | 355.2 |
| Compound 86 | 5-(2,6-difluorophenyl)-9-(tetrahydro-2H-pyran-4-yl)-1,6-dihydropyrazolo[4,3-d]pyrido[3,2-f][1,3]diazepine | HPLC-MS B | 2.60 | 382.2 |
| Compound 87 | 5-(2,6-difluorophenyl)-9-(1H-pyrrol-2-yl)-1,6-dihydropyrazolo[4,3-d]pyrido[3,2-f][1,3]diazepine | HPLC-MS B | 2.79 | 363.2 |
| Compound 88 | 3-bromo-5-(2-chloro-6-fluorophenyl)-1,6-dihydropyrazolo[4,3-d]pyrido[3,2-f][1,3]diazepine | HPLC-MS B | 3.35 | 392.0 |
| Compound 89 | 5-(2-chloro-6-fluorophenyl)-4,9-dihydro-1H-dipyrazolo[4,3-d:3',4'-f][1,3]diazepine | HPLC-MS B | 0.28 | 301.1 |
| Compound 90 | 5-(2,6-dichlorophenyl)-9-(difluoromethoxy)-1,6-dihydrobenzo[d]pyrazolo[3,4-f][1,3]diazepine | HPLC-MS B | 2.82 | 395.0 |
| Compound 91 | 5-(2,6-difluorophenyl)-1,4-dihydrobenzo[d]pyrazolo[3,4-f][1,3]diazepine-9-carboxylic acid | HPLC-MS C | 2.70 | 341.2 |
| Compound 92 | 5-(2-chloro-6-fluorophenyl)-1,4-dihydrobenzo[d]pyrazolo[3,4-f][1,3]diazepine-9-carboxylic acid | HPLC-MS C | 2.81 | 357.0 |
| Compound 93 | 5-(2,6-difluorophenyl)-1,4-dihydrobenzo[d]pyrazolo[3,4-f][1,3]diazepine-9-carboxamide | HPLC-MS C | 2.42 | 340.2 |
| Compound 94 | 5-(2-chloro-6-fluorophenyl)-1,6-dihydrobenzo[d]pyrazolo[3,4-f][1,3]diazepine-9-carboxamide | HPLC-MS C | 2.56 | 356.2 |
| Compound 95 | 5-(2,6-difluorophenyl)-N-(tetrahydro-2H-pyran-4-yl)-1,4-dihydrobenzo[d]pyrazolo[3,4-f][1,3]diazepine-8-carboxamide | HPLC-MS C | 2.66 | 424.2 |
| Compound 96 | 6-(2,6-difluorophenyl)-7,8-dihydropyrazolo[3,4-d]pyrido[2,3-f][1,3]diazEpin-2(1H)-one | HPLC-MS A | 2.62 | 314.2 |
| Compound 97 | 5-(2-chloro-6-fluorophenyl)-N-(2-fluoroethyl)-1,4-dihydrobenzo[d]pyrazolo[3,4-f][1,3]diazepine-9-carboxamide | HPLC-MS C | 2.81 | 402.2 |
| Compound 98 | 2-(5-(2,6-difluorophenyl)-1,6-dihydrobenzo[d]pyrazolo[3,4-f][1,3]diazepin-8-yl)propan-2-ol | HPLC-MS C | 2.69 | 355.2 |
| Compound 99 | 5-(2,6-difluorophenyl)-8-((tetrahydro-2H-pyran-4-yl)oxy)-1,4-dihydrobenzo[d]pyrazolo[3,4-f][1,3]diazepine | HPLC-MS A | 2.85 | 397.2 |
| Compound 100 | 5-(2,6-difluorophenyl)-8-isopropoxy-1,6-dihydrobenzo[d]pyrazolo[3,4-f][1,3]diazepine | HPLC-MS C | 3.10 | 355.2 |
| Compound 101 | 5-(2,6-difluorophenyl)-N-(2-fluoroethyl)-1,4-dihydrobenzo[d]pyrazolo[3,4-f][1,3]diazepine-9-carboxamide | HPLC-MS C | 2.80 | 386.2 |

TABLE 3-continued

| Compound-No | IUPAC-Name | HPLC-MS-Method | retention time (min) | m + H Found |
|---|---|---|---|---|
| Compound 102 | 5-(2,6-difluorophenyl)-9-((tetrahydro-2H-pyran-4-yl)oxy)-1,6-dihydrobenzo[d]pyrazolo[3,4-f][1,3]diazepine | HPLC-MS C | 3.02 | 397.2 |
| Compound 103 | 5-(2,6-difluorophenyl)-1,6-dihydrobenzo[d]pyrazolo[3,4-f][1,3]diazepin-9-amine | HPLC-MS C | 3.71 | 312.2 |
| Compound 104 | 5-(2,6-difluorophenyl)-1,6-dihydrobenzo[d]pyrazolo[3,4-f][1,3]diazepin-8-amine | HPLC-MS C | 2.54 | 312.2 |
| Compound 105 | 5-(2,6-difluorophenyl)-N-(tetrahydro-2H-pyran-4-yl)-1,4-dihydropyrazolo[4,3-d]pyrido[3,2-f][1,3]diazepine-8-carboxamide | HPLC-MS A | 2.99 | 425.2 |
| Compound 106 | 5-(2-fluoro-6-nitrophenyl)-1,6-dihydrobenzo[d]pyrazolo[3,4-f][1,3]diazepine | HPLC-MS A | 2.71 | 324.2 |
| Compound 107 | 5-(2,6-difluoro-3-nitrophenyl)-1,6-dihydrobenzo[d]pyrazolo[3,4-f][1,3]diazepine | HPLC-MS A | 3.02 | 342.0 |
| Compound 108 | 5-(2-fluoro-6-nitrophenyl)-1,6-dihydropyrazolo[4,3-d]pyrido[3,2-f][1,3]diazepine | HPLC-MS A | 2.70 | 325.2 |
| Compound 109 | 5-(2,6-difluoro-3-nitrophenyl)-1,6-dihydropyrazolo[4,3-d]pyrido[3,2-f][1,3]diazepine | HPLC-MS A | 2.59 | 343.2 |
| Compound 110 | (5-(2,6-difluorophenyl)-1,4-dihydrobenzo[d]pyrazolo[3,4-f][1,3]diazepin-9-yl)(3-fluoroazetidin-1-yl)methanone | HPLC-MS C | 2.84 | 398.2 |
| Compound 111 | 5-(2-fluoro-6-iodophenyl)-1,4-dihydrobenzo[d]pyrazolo[3,4-f][1,3]diazepine | HPLC-MS A | 2.81 | 405.0 |
| Compound 112 | 5-(2,6-difluorophenyl)-N-(2-fluoroethyl)-1,6-dihydropyrazolo[4,3-d]pyrido[4,3-f][1,3]diazepine-9-carboxamide | HPLC-MS C | 2.87 | 387.2 |
| Compound 113 | 5-(2,6-difluorophenyl)-N-(2-fluoroethyl)-N-methyl-1,4-dihydrobenzo[d]pyrazolo[3,4-f][1,3]diazepine-9-carboxamide | HPLC-MS C | 2.85 | 400.2 |
| Compound 114 | 5-(2-fluoro-6-methoxyphenyl)-1,6-dihydrobenzo[d]pyrazolo[3,4-f][1,3]diazepine | HPLC-MS A | 2.63 | 309.2 |
| Compound 115 | 5-(2,6-difluorophenyl)-N-(2-fluoroethyl)-1,6-dihydrobenzo[d]pyrazolo[3,4-f][1,3]diazepin-9-amine | HPLC-MS C | 2.92 | 385.2 |
| Compound 116 | 5-(2,6-difluorophenyl)-N-(2-fluoroethyl)-1,6-dihydrobenzo[d]pyrazolo[3,4-f][1,3]diazepin-8-amine | HPLC-MS C | 2.25 | 358.2 |
| Compound 117 | 4-(5-(2,6-difluorophenyl)-1,4-dihydrobenzo[d]pyrazolo[3,4-f][1,3]diazepin-9-yl)morpholine | HPLC-MS C | 2.93 | 382.2 |
| Compound 118 | 4-(5-(2,6-difluorophenyl)-1,4-dihydrobenzo[d]pyrazolo[3,4-f][1,3]diazepin-8-yl)morpholine | HPLC-MS C | 3.29 | 382.2 |
| Compound 119 | 5-(2-fluoro-6-methoxyphenyl)-1,6-dihydropyrazolo[4,3-d]pyrido[3,2-f][1,3]diazepine | HPLC-MS A | 2.46 | 310.2 |
| Compound 120 | 5-(2-chloro-6-fluorophenyl)-9-(3,6-dihydro-2H-pyran-4-yl)-1,6-dihydropyrazolo[4,3-d]pyrido[3,2-f][1,3]diazepine | HPLC-MS C | 3.23 | 396.2 |
| Compound 121 | 5-(2,6-difluoro-4-(2-fluoroethoxyphenyl)-9-(3,6-dihydro-2H-pyran-4-yl)-1,6-dihydropyrazolo[4,3-d]pyrido[3,2-f][1,3]diazepine | HPLC-MS C | 3.26 | 442.2 |
| Compound 122 | 5-(2,6-difluorophenyl)-7-methyl-1,6-dihydrobenzo[d]pyrazolo[3,4-f][1,3]diazepine | HPLC-MS A | 2.99 | 311.2 |
| Compound 123 | 9-(3,6-dihydro-2H-pyran-4-yl)-5-(2-fluoro-6-nitrophenyl)-1,6-dihydropyrazolo[4,3-d]pyrido[3,2-f][1,3]diazepine | HPLC-MS A | 3.12 | 407.2 |
| Compound 124 | 4-(9-(3,6-dihydro-2H-pyran-4-yl)-1,4-dihydropyrazolo[4,3-d]pyrido[3,2-f][1,3]diazepin-5-yl)-3,5-difluoro-N-(2-fluoroethyl)aniline | HPLC-MS A | 2.93 | 441.2 |
| Compound 125 | 5-(2-fluoro-6-nitrophenyl)-9-methyl-1,6-dihydrobenzo[d]pyrazolo[3,4-f][1,3]diazepine | HPLC-MS D | 2.44 | 338.2 |
| Compound 126 | 3,5-difluoro-N-(2-fluoroethyl)-4-(9-methyl-1,6-dihydrobenzo[d]pyrazolo[3,4-f][1,3]diazepin-5-yl)aniline | HPLC-MS D | 2.49 | 372.2 |
| Compound 127 | 5-(2,6-difluorophenyl)-9-methoxy-1,6-dihydropyrazolo[4,3-d]pyrido[4,3-f][1,3]diazepine | HPLC-MS B | 2.16 | 328.2 |
| Compound 128 | 5-(2,6-difluorophenyl)-9-(1-(2-fluoroethyl)-1,2,3,6-tetrahydropyridin-4-yl)-1,6-dihydropyrazolo[4,3-d]pyrido[3,2-f][1,3]diazepine | HPLC-MS B | 1.75 | 425.0 |
| Compound 129 | 3-(9-(3,6-dihydro-2H-pyran-4-yl)-1,4-dihydropyrazolo[4,3-d]pyrido[3,2-f][1,3]diazepin-5-yl)-2,4-difluoro-N-(2-fluoroethyl)aniline | HPLC-MS A | 3.13 | 441.2 |
| Compound 130 | 2,4-difluoro-N-(2-fluoroethyl)-3-(9-methyl-1,4-dihydrobenzo[d]pyrazolo[3,4-f][1,3]diazepin-5-yl)aniline | HPLC-MS A | 2.95 | 372.0 |
| Compound 131 | 5-(2,6-difluorophenyl)-9-(1,2,3,6-tetrahydropyridin-4-yl)-1,6-dihydropyrazolo[4,3-d]pyrido[3,2-f][1,3]diazepine | HPLC-MS C | 2.32 | 379.2 |
| Compound 132 | 2-(4-(5-(2,6-difluorophenyl)-1,6-dihydropyrazolo[4,3-d]pyrido[3,2-f][1,3]diazepin-9-yl)-5,6-dihydropyridin-1(2H)-yl)ethan-1-ol | HPLC-MS E | 0.56 | 423.0 |
| Compound 133 | 5-(2,6-difluorophenyl)-9-(3,6-dihydro-2H-pyran-4-yl)-1,4-dihydrobenzo[d]pyrazolo[3,4-f][1,3]diazepine | HPLC-MS A | 2862 | 379.2 |
| Compound 134 | 5-(2,6-difluorophenyl)-9-methoxy-1,4-dihydropyrazolo[4,3-d]pyrido[2,3-f][1,3]diazepine | HPLC-MS A | 2.57 | 328.2 |
| Compound 135 | 3-chloro-5-(2,6-difluorophenyl)-1,4-dihydrobenzo[d]pyrazolo[3,4-f][1,3]diazepine | HPLC-MS C | 3.36 | 331.1 |
| Compound 136 | 5-(2,6-difluorophenyl)-1,4-dihydrobenzo[d]pyrazolo[3,4-f][1,3]diazepin-9-yl dimethylcarbamate | HPLC-MS B | 2.388 | 384 |
| Compound 137 | 3-cyclopropyl-5-(2,6-difluorophenyl)-1,6-dihydrobenzo[d]pyrazolo[3,4-f][1,3]diazepine | HPLC-MS C | 3.47 | 337.2 |
| Compound 138 | 5-(2,6-difluorophenyl)-7-fluoro-9-methyl-1,4-dihydrobenzo [d]pyrazolo[3,4-f][1,3]diazepine | HPLC-MS C | 3.444 | 329.2 |
| Compound 139 | 5-(2,6-difluorophenyl)-9-isopropyl-1,6-dihydrobenzo[d]pyrazolo[3,4-f][1,3]diazepine | HPLC-MS A | 3.136 | 339.2 |
| Compound 140 | 5-(2,6-difluorophenyl)-1,6-dihydropyrazolo[4,3-d]pyrido[3,2-f][1,3]diazepine-9-carboxamide | HPLC-MS A | 2.502 | 341.2 |
| Compound 141 | 1-(5-(2,6-difluorophenyl)-1,4-dihydrobenzo[d]pyrazolo[3,4-f][1,3]diazepin-9-yl)-3-methylimidazolidin-2-one | HPLC-MS A | 2.625 | 395.23 |
| Compound 142 | 5-(2,6-difluorophenyl)-10-methoxy-1,4-dihydropyrazolo[4,3-d]pyrido[3,4-f][1,3]diazepine | HPLC-MS A | 2.77 | 328.2 |
| Compound 143 | 3-chloro-5-(2,6-difluorophenyl)-9-methyl-1,4-dihydrobenzo[d]pyrazolo [3,4-f][1,3]diazepine | HPLC-MS C | 3.57 | 345.2 |
| Compound 144 | 5-(2,6-difluorophenyl)-1,6-dihydropyrazolo[4,3-d]pyrido[3,4-f][1,3]diazepin-9-ol | HPLC-MS C | 2.208 | 314 |
| Compound 145 | 5-(2,6-difluorophenyl)-9-methyl-3-(methylthio)-1,4-dihydrobenzo[d]pyrazolo[3,4-f][1,3]diazepine | HPLC-MS C | 3.62 | 357.2 |
| Compound 146 | 5-(2,6-difluorophenyl)-3-(methylthio)-1,4-dihydrobenzo[d]pyrazolo [3,4-f][1,3]diazepine | HPLC-MS C | 3.43 | 343.2 |
| Compound 147 | 9-chloro-5-(2,6-difluorophenyl)-1,6-dihydropyrazolo[4,3-d]pyrido[4,3-f][1,3]diazepine | HPLC-MS B | 2.62 | 332 |
| Compound 148 | 7-chloro-5-(2,6-difluorophenyl)-9-(trifluoromethyl)-1,4-dihydropyrazolo[4,3-d]pyrido[4,3-f][1,3]diazepine | HPLC-MS A | 4.058 | 400.2 |

TABLE 3-continued

| Compound-No | IUPAC-Name | HPLC-MS-Method | retention time (min) | m + H Found |
|---|---|---|---|---|
| Compound 149 | 5-(2,6-difluorophenyl)-9-(3,6-dihydro-2H-pyran-4-yl)-1,6-dihydropyrazolo[4,3-d]pyrido[4,3-f][1,3]diazepine | HPLC-MS B | 1.73 | 380 |
| Compound 150 | 2-((4-(2,6-dihydrobenzo[d]pyrazolo[3,4-f][1,3]diazepin-5-yl)-3,5-difluorophenyl)amino)ethan-1-ol | HPLC-MS A | 2.515 | 356.2 |
| Compound 151 | 5-(2,6-difluorophenyl)-9-(trifluoromethyl)-1,4-dihydropyrazolo[4,3-d]pyrido [4,3-f][1,3]diazepine | HPLC-MS A | 2.515 | 356.2 |
| Compound 152 | 5-(2,6-dichlorophenyl)-9-methyl-1,4-dihydrobenzo[d]pyrazolo[3,4-f][1,3]diazepine | HPLC-MS C | 3.42 | 344.2 |
| Compound 153 | 4-(5-(2,6-difluorophenyl)-1,6-dihydropyrazolo[4,3-d]pyrido[4,3-f][1,3]diazepin-7-yl)morpholine | HPLC-MS B | 2.64 | 383 |
| Compound 154 | 5-(2,6-difluorophenyl)-3-(6-methylpyrimidin-4-yl)-1,4-dihydrobenzo [d]pyrazolo[3,4-f][1,3]diazepine | HPLC-MS A | 3.115 | 389.2 |
| Compound 155 | 5-(2-chloro-6-fluorophenyl)-8-((tetrahydro-2H-pyran-4-yl)oxy)-1,4-dihydrobenzo[d]pyrazolo[3,4-f][1,3]diazepine | HPLC-MS A | 2.919 | 413.2 |
| Compound 156 | 5-(2,6-difluorophenyl)-9-methyl-1,6-dihydrobenzo[d]pyrazolo[3,4-f][1,3]diazepine-8-carboxylic acid | HPLC-MS C | 2.04 | 355.0 |
| Compound 157 | 5-(2,6-difluorophenyl)-9-methyl-N-(tetrahydro-2H-pyran-4-yl)-1,4-dihydrobenzo[d]pyrazolo[3,4-f][1,3]diazepine-8-carboxamide | HPLC-MS C | 2.74 | 438.2 |
| Compound 158 | 5-(2-chloro-6-fluorophenyl)-8-methoxy-1,4-dihydrobenzo[d]pyrazolo[3,4-f][1,3]diazepine | HPLC-MS A | 2.818 | 343 |
| Compound 159 | 5-(2,6-difluorophenyl)-8-(1H-pyrazol-5-yl)-1,4-dihydrobenzo[d]pyrazolo[3,4-f][1,3]diazepine | HPLC-MS A | 2.628 | 363.2 |
| Compound 160 | 5-(2-chloro-6-fluorophenyl)-8-(1H-pyrazol-5-yl)-1,4-dihydrobenzo[d]pyrazolo[3,4-f][1,3]diazepine | HPLC-MS A | 2.705 | 379 |
| Compound 161 | 5-(2-bromo-6-fluorophenyl)-9-methyl-1,4-dihydrobenzo[d]pyrazolo[3,4-f][1,3]diazepine | HPLC-MS A | 2.884 | 373 |
| Compound 162 | N-(3-(5-(2,6-difluorophenyl)-1,4-dihydrobenzo[d]pyrazolo[3,4-f][1,3]diazepin-8-yl)phenyl)acetamide | HPLC-MS B | 2.549 | 430.4 |
| Compound 163 | 5-(2-fluoro-6-iodophenyl)-9-methyl-1,4-dihydrobenzo[d]pyrazolo[3,4-f][1,3]diazepine | HPLC-MS B | 2.501 | 419 |
| Compound 164 | methyl(5-(2,6-difluorophenyl)-2,4-dihydrobenzo[d]pyrazolo[3,4-f][1,3]diazepin-8-yl)carbamate | HPLC-MS A | 2.611 | 370 |
| Compound 165 | methyl(5-(2,6-difluorophenyl)-1,4-dihydrobenzo[d]pyrazolo[3,4-f][1,3]diazepin-9-yl)carbamate | HPLC-MS A | 2.61 | 370.3 |
| Compound 166 | 3-chloro-5-(2,6-difluorophenyl)-7-fluoro-9-methyl-1,4-dihydrobenzo[d]pyrazolo[3,4-f][1,3]diazepine | HPLC-MS B | 3.67 | 363 |
| Compound 167 | 5-(2,6-difluorophenyl)-9-ethyl-7-fluoro-1,4-dihydrobenzo[d]pyrazolo[3,4-f][1,3]diazepine | HPLC-MS B | 3.03 | 343 |
| Compound 168 | 3-chloro-5-(2,6-difluorophenyl)-9-ethyl-7-fluoro-1,4-dihydrobenzo[d]pyrazolo[3,4-f][1,3]diazepine | HPLC-MS B | 3.91 | 377 |
| Compound 169 | 5-(2,6-difluorophenyl)-7-fluoro-8-methoxy-1,4-dihydrobenzo[d]pyrazolo[3,4-f][1,3]diazepine | HPLC-MS A | 2.976 | 345 |
| Compound 170 | 5-(2,6-difluorophenyl)-7,8-difluoro-1,4-dihydrobenzo[d]pyrazolo[3,4-f][1,3]diazepine | HPLC-MS A | 3.331 | 333.2 |
| Compound 171 | 3,9-dichloro-5-(2,6-difluorophenyl)-1,6-dihydropyrazolo[4,3-d]pyrido[4,3-f][1,3]diazepine | HPLC-MS B | 3.89 | 366 |
| Compound 172 | 5-(2-fluoro-6-methylphenyl)-9-methyl-1,6-dihydrobenzo[d]pyrazolo[3,4-f][1,3]diazepine | HPLC-MS B | 3.371 | 307.2 |
| Compound 173 | 5-(2,6-difluoro-4-methoxyphenyl)-9-methyl-1,6-dihydrobenzo[d]pyrazolo[3,4-f][1,3]diazepine | HPLC-MS C | 3.44 | 341.2 |
| Compound 174 | 3,5-difluoro-N,N-dimethyl-4-(9-methyl-1,6-dihydrobenzo[d]pyrazolo[3,4-f][1,3]diazepin-5-yl)aniline | HPLC-MS C | 3.43 | 354.2 |
| Compound 175 | 9-methyl-5-(2,4,6-trifluorophenyl)-1,6-dihydrobenzo[d]pyrazolo[3,4-f][1,3]diazepine | HPLC-MS A | 2.843 | 329 |
| Compound 176 | 5-(4-bromo-2,6-difluorophenyl)-9-methyl-1,6-dihydrobenzo[d]pyrazolo[3,4-f][1,3]diazepine | HPLC-MS A | 3.077 | 391 |
| Compound 177 | 2,4-difluoro-3-(9-methyl-1,6-dihydrobenzo[d]pyrazolo[3,4-f][1,3]diazepin-5-yl)aniline | HPLC-MS C | 2.99 | 326 |
| Compound 178 | 5-(2,6-difluoro-3-methylphenyl)-9-methyl-2,4-dihydrobenzo[d]pyrazolo[3,4-f][1,3]diazepine | HPLC-MS C | 3.43 | 325 |
| Compound 179 | 5-(2,6-difluoro-4-methylphenyl)-9-methyl-2,4-dihydrobenzo[d]pyrazolo[3,4-f][1,3]diazepine | HPLC-MS C | 3.43 | 325 |
| Compound 180 | 5-(2,6-difluoro-3-methoxyphenyl)-9-methyl-2,4-dihydrobenzo[d]pyrazolo[3,4-f][1,3]diazepine | HPLC-MS C | 3.43 | 325 |
| Compound 181 | 2,4-difluoro-N,N-dimethyl-3-(9-methyl-1,4-dihydrobenzo[d]pyrazolo[3,4-f][1,3]diazepin-5-yl)aniline | HPLC-MS C | 3.29 | 341.2 |
| Compound 182 | 9-methyl-5-(2,3,6-trifluorophenyl)-1,4-dihydrobenzo[d]pyrazolo [3,4-f][1,3]diazepine | HPLC-MS C | 3.36 | 329.0 |
| Compound 183 | 5-(3-bromo-2-chloro-6-fluorophenyl)-9-methyl-1,4-dihydrobenzo [d]pyrazolo[3,4-f][1,3]diazepine | HPLC-MS C | 3.65 | 406.9 |
| Compound 184 | 5-(3-bromo-6-chloro-2-fluorophenyl)-9-methyl-1,4-dihydrobenzo [d]pyrazolo[3,4-f][1,3]diazepine | HPLC-MS C | 3.67 | 407 |
| Compound 185 | 5-(2-chloro-3,6-difluorophenyl)-9-methyl-1,4-dihydrobenzo[d]pyrazolo[3,4-f][1,3]diazepine | HPLC-MS C | 3.44 | 345.0 |
| Compound 186 | 5-(6-chloro-2,3-difluorophenyl)-9-methyl-1,4-dihydrobenzo[d]pyrazolo[3,4-f][1,3]diazepine | HPLC-MS C | 3.46 | 345.0 |
| Compound 187 | 4-(5-(2-chloro-6-fluorophenyl)-1,6-dihydrobenzo[d]pyrazolo[3,4-f][1,3]diazepin-9-yl)morpholine | HPLC-MS C | 3.059 | 398.01 |
| Compound 188 | 5-(2-chloro-6-fluorophenyl)-9-(trifluoromethyl)-1,4-dihydropyrazolo[4,3-d]pyrido[4,3-f][1,3]diazepine | HPLC-MS B | 3.32 | 382 |
| Compound 189 | 9-(trifluoromethyl)-5-(2,4,6-trifluorophenyl)-1,4-dihydrobenzo[d]pyrazolo[3,4-f][1,3]diazepine | HPLC-MS C | 3.71 | 383.2 |
| Compound 190 | 9-chloro-5-(2-chloro-6-fluorophenyl)-2,4-dihydropyrazolo[4,3-d]pyrido[4,3-f][1,3]diazepine | HPLC-MS A | 3.098 | 350 |
| Compound 191 | 5-(2,6-difluorophenyl)-9-(4,4-difluoropiperidin-1-yl)-1,6-dihydrobenzo[d]pyrazolo[3,4-f][1,3]diazepine | HPLC-MS C | 3.52 | 416.2 |

TABLE 3-continued

| Compound-No | IUPAC-Name | HPLC-MS-Method | retention time (min) | m + H Found |
|---|---|---|---|---|
| Compound 192 | 5-(2-chloro-6-fluorophenyl)-9-(4,4-difluoropiperidin-1-yl)-1,6-dihydrobenzo[d]pyrazolo[3,4-f][1,3]diazepine | HPLC-MS C | 3.6 | 432 |
| Compound 193 | 9-(4,4-difluoropiperidin-1-yl)-5-(2,4,6-trifluorophenyl)-1,6-dihydrobenzo[d]pyrazolo[3,4-f][1,3]diazepine | HPLC-MS C | 3.61 | 434 |
| Compound 194 | 9-chloro-5-(2,4,6-trifluorophenyl)-2,4-dihydrobenzo[d]pyrazolo[3,4-f][1,3]diazepine | HPLC-MS B | 2.86 | 349.2 |
| Compound 195 | 9-(3,3-difluoroazetidin-1-yl)-5-(2,6-difluorophenyl)-1,6-dihydrobenzo[d]pyrazolo[3,4-f][1,3]diazepine | HPLC-MS C | 3.35 | 388 |
| Compound 196 | 5-(2-chloro-6-fluorophenyl)-9-(3,3-difluoroazetidin-1-yl)-1,6-dihydrobenzo[d]pyrazolo[3,4-f][1,3]diazepine | HPLC-MS B | 2.67 | 404 |
| Compound 197 | 9-(difluoromethoxy)-5-(2,6-difluorophenyl)-2,4-dihydropyrazolo[4,3-d]pyrido[4,3-f][1,3]diazepine | HPLC-MS B | 2.8 | 364 |
| Compound 198 | 9-chloro-5-(2,6-difluorophenyl)-1,6-dihydrobenzo[d]pyrazolo[3,4-f][1,3]diazepine-8-carboxylic acid | HPLC-MS D | 2.18 | 375.2 |
| Compound 199 | 9-chloro-5-(2,6-difluorophenyl)-N-(tetrahydro-2H-pyran-4-yl)-2,6-dihydrobenzo[d]pyrazolo[3,4-f][1,3]diazepine-8-carboxamide | HPLC-MS A | 2.68 | 458.2 |
| Compound 200 | 9-chloro-5-(2,6-difluorophenyl)-N-ethyl-2,6-dihydrobenzo[d]pyrazolo[3,4-f][1,3]diazepine-8-carboxamide | HPLC-MS A | 2.71 | 402.2 |
| Compound 201 | N-(tert-butyl)-9-chloro-5-(2,6-difluorophenyl)-2,6-dihydrobenzo[d]pyrazolo[3,4-f][1,3]diazepine-8-carboxamide | HPLC-MS A | 3.22 | 430.2 |
| Compound 202 | 9-chloro-5-(2,6-difluorophenyl)-N-(2,2,2-trifluoroethyl)-2,6-dihydrobenzo[d]pyrazolo[3,4-f][1,3]diazepine-8-carboxamide | HPLC-MS A | 3.08 | 456.2 |
| Compound 203 | 9-fluoro-5-(2,4,6-trifluorophenyl)-1,6-dihydrobenzo[d]pyrazolo[3,4-f][1,3]diazepine | HPLC-MS B | 2.44 | 333 |
| Compound 204 | 5-(2,6-difluorophenyl)-9-(2-fluoroethyl)-2,4-dihydrobenzo[d]pyrazolo[3,4-f][1,3]diazepine | HPLC-MS C | 3.23 | 343.2 |
| Compound 205 | 5-(2,6-difluoro-4-(trifluoromethyl)phenyl)-9-methyl-2,4-dihydrobenzo[d]pyrazolo[3,4-f][1,3]diazepine | HPLC-MS B | 3.125 | 379 |
| Compound 206 | 5-(2-fluoro-6-(trifluoromethyl)phenyl)-9-methyl-2,4-dihydrobenzo[d]pyrazolo[3,4-f][1,3]diazepine | HPLC-MS C | 3.60 | 361.0 |
| Compound 207 | benzyl(5-(2,6-difluorophenyl)-2,4-dihydrobenzo[d]pyrazolo[3,4-f][1,3]diazepin-9-yl)carbamate | HPLC-MS C | 3.77 | 446.2 |
| Compound 208 | 2-(5-(2,6-difluorophenyl)-2,4-dihydrobenzo[d]pyrazolo[3,4-f][1,3]diazepin-9-yl)ethan-1-ol | HPLC-MS C | 2.74 | 341.20 |
| Compound 209 | 9-(2-chloroethyl)-5-(2,6-difluorophenyl)-2,4-dihydrobenzo[d]pyrazolo[3,4-f][1,3]diazepine | HPLC-MS C | 3.45 | 359.10 |
| Compound 210 | 5-(2,6-difluorophenyl)-1,6-dihydro-[1,3]dioxolo[4',5':4,5]benzo[1,2-d]pyrazolo[3,4-f][1,3]diazepine | HPLC-MS B | 2.45 | 341 |
| Compound 211 | 5-(2,6-difluorophenyl)-N-ethyl-9-fluoro-2,6-dihydrobenzo[d]pyrazolo[3,4-f][1,3]diazepine-8-carboxamide | HPLC-MS D | 2.57 | 386.2 |
| Compound 212 | 5-(2,6-difluorophenyl)-3,9-dimethyl-2,4-dihydrobenzo[d]pyrazolo[3,4-f][1,3]diazepine | HPLC-MS C | 3.38 | 325.2 |
| Compound 213 | 5-(2,6-difluorophenyl)-1,4-dihydropyrazolo[4,3-d]pyrimido[5,4-f][1,3]diazepine | HPLC-MS C | 2.55 | 299.20 |
| Compound 214 | 5-(2,6-difluoro-4-(trifluoromethoxy)phenyl)-9-fluoro-2,4-dihydrobenzo[d]pyrazolo[3,4-f][1,3]diazepine | HPLC-MS C | 3.76 | 399 |
| Compound 215 | 5-(4-(difluoromethoxy)-2,6-difluorophenyl)-9-fluoro-1,6-dihydrobenzo[d]pyrazolo[3,4-f][1,3]diazepine | HPLC-MS C | 3.52 | 381.2 |
| Compound 216 | 5-(2,6-difluorophenyl)-9-fluoro-N-(2-fluoroethyl)-2,6-dihydrobenzo[d]pyrazolo[3,4-f][1,3]diazepine-8-carboxamide | HPLC-MS A | 2.67 | 404.2 |
| Compound 217 | 5-(2,6-difluoro-3-(trifluoromethyl)phenyl)-9-methyl-2,4-dihydrobenzo[d]pyrazolo[3,4-f][1,3]diazepine | HPLC-MS C | 3.71 | 379.2 |
| Compound 218 | 5-(2,6-difluorophenyl)-2,4-dihydropyrazolo[4,3-d]pyrimido[5,4-f][1,3]diazepin-8-amine | HPLC-MS C | 2.43 | 314.20 |
| Compound 219 | 5-(2,6-difluorophenyl)-8-(4-methylpiperazin-1-yl)-2,4-dihydropyrazolo[4,3-d]pyrimido[5,4-f][1,3]diazepine | HPLC-MS C | 2.54 | 397.2 |
| Compound 220 | 5-(2,6-difluorophenyl)-9-fluoro-8-((tetrahydro-2H-pyran-4-yl)oxy)-2,4-dihydrobenzo[d]pyrazolo[3,4-f][1,3]diazepine | HPLC-MS D | 2.62 | 415.2 |
| Compound 221 | 5-(2-chloro-6-fluorophenyl)-9-fluoro-8-((tetrahydro-2H-pyran-4-yl)oxy)-2,4-dihydrobenzo[d]pyrazolo[3,4-f][1,3]diazepine | HPLC-MS D | 2.74 | 431.2 |
| Compound 222 | 5-(2,6-dichlorophenyl)-9-fluoro-8-((tetrahydro-2H-pyran-4-yl)oxy)-2,4-dihydrobenzo[d]pyrazolo[3,4-f][1,3]diazepine | HPLC-MS C | 3.44 | 447.2 |
| Compound 223 | 9-fluoro-5-(2-fluoro-6-(trifluoromethyl)phenyl)-8-((tetrahydro-2H-pyran-4-yl)oxy)-2,4-dihydrobenzo[d]pyrazolo[3,4-f][1,3]diazepine | HPLC-MS C | 3.45 | 465.2 |
| Compound 224 | 5-(2-chloro-6-(trifluoromethyl)phenyl)-9-fluoro-8-((tetrahydro-2H-pyran-4-yl)oxy)-2,4-dihydrobenzo[d]pyrazolo[3,4-f][1,3]diazepine | HPLC-MS C | 3.51 | 481.2 |
| Compound 225 | 5-(2,6-difluorophenyl)-9-fluoro-8-(pyridazin-3-yl)-2,4-dihydrobenzo[d]pyrazolo[3,4-f][1,3]diazepine | HPLC-MS C | 2.96 | 393.2 |
| Compound 226 | 5-(2,6-difluorophenyl)-9-fluoro-8-(pyridazin-4-yl)-2,4-dihydrobenzo[d]pyrazolo[3,4-f][1,3]diazepine | HPLC-MS C | 2.9 | 393.2 |
| Compound 227 | 5-(2,6-dichlorophenyl)-9-fluoro-8-(pyridazin-3-yl)-2,4-dihydrobenzo[d]pyrazolo[3,4-f][1,3]diazepine | HPLC-MS B | 2.56 | 425 |
| Compound 228 | 5-(2-chloro-6-fluorophenyl)-9-fluoro-8-(pyridazin-3-yl)-2,4-dihydrobenzo[d]pyrazolo[3,4-f][1,3]diazepine | HPLC-MS B | 2.49 | 409.2 |
| Compound 229 | 5-(2,6-dichlorophenyl)-9-fluoro-8-(pyridazin-4-yl)-2,4-dihydrobenzo[d]pyrazolo[3,4-f][1,3]diazepine | HPLC-MS B | 2.55 | 425 |
| Compound 230 | 5-(2-chloro-6-fluorophenyl)-9-fluoro-8-(pyridazin-4-yl)-2,4-dihydrobenzo[d]pyrazolo[3,4-f][1,3]diazepine | HPLC-MS B | 2.48 | 409.2 |
| Compound 231 | 5-(2,6-difluorophenyl)-9-fluoro-8-phenyl-2,4-dihydrobenzo[d]pyrazolo[3,4-f][1,3]diazepine | HPLC-MS B | 3.19 | 391.2 |

TABLE 3-continued

| Compound-No | IUPAC-Name | HPLC-MS-Method | retention time (min) | m + H Found |
|---|---|---|---|---|
| Compound 232 | 5-(2-chloro-6-fluorophenyl)-9-fluoro-8-(pentan-3-yloxy)-2,6-dihydrobenzo[d]pyrazolo[3,4-f][1,3]diazepine | HPLC-MS C | 4.06 | 417.2 |
| Compound 233 | 5-(2,6-difluorophenyl)-8-(2-fluorophenyl)-2,4-dihydrobenzo[d]pyrazolo[3,4-f][1,3]diazepine | HPLC-MS C | 3.75 | 391.2 |
| Compound 234 | 5-(2-chloro-6-fluorophenyl)-8-(2-fluorophenyl)-2,4-dihydrobenzo[d]pyrazolo[3,4-f][1,3]diazepine | HPLC-MS C | 3.83 | 407.2 |
| Compound 235 | 5-(2-chloro-6-fluorophenyl)-9-fluoro-8-isopropoxy-2,6-dihydrobenzo[d]pyrazolo[3,4-f][1,3]diazepine | HPLC-MS C | 3.67 | 389.2 |
| Compound 236 | 5-(2,6-dichlorophenyl)-8-(2-fluorophenyl)-2,4-dihydrobenzo[d]pyrazolo[3,4-f][1,3]diazepine | HPLC-MS C | 3.9 | 423.2 |
| Compound 237 | 5-(2,6-difluorophenyl)-8-(4-fluorophenyl)-2,4-dihydrobenzo[d]pyrazolo[3,4-f][1,3]diazepine | HPLC-MS C | 3.79 | 391.2 |
| Compound 238 | 5-(2-chloro-6-fluorophenyl)-8-(4-fluorophenyl)-2,4-dihydrobenzo[d]pyrazolo[3,4-f][1,3]diazepine | HPLC-MS C | 3.87 | 407.2 |
| Compound 239 | 8-(sec-butoxy)-5-(2-chloro-6-fluorophenyl)-9-fluoro-2,6-dihydrobenzo[d]pyrazolo[3,4-f][1,3]diazepine | HPLC-MS C | 3.87 | 403.2 |
| Compound 240 | 5-(2,6-difluorophenyl)-8-(3-fluorophenyl)-2,4-dihydrobenzo[d]pyrazolo[3,4-f][1,3]diazepine | HPLC-MS C | 3.81 | 391.2 |
| Compound 241 | 5-(2-chloro-6-fluorophenyl)-8-(3-fluorophenyl)-2,4-dihydrobenzo[d]pyrazolo[3,4-f][1,3]diazepine | HPLC-MS C | 3.89 | 407.2 |
| Compound 242 | 5-(2,6-dichlorophenyl)-8-(4-fluorophenyl)-2,4-dihydrobenzo[d]pyrazolo[3,4-f][1,3]diazepine | HPLC-MS C | 3.94 | 423.2 |
| Compound 243 | 5-(2,6-dichlorophenyl)-8-(3-fluorophenyl)-2,4-dihydrobenzo[d]pyrazolo[3,4-f][1,3]diazepine | HPLC-MS C | 3.97 | 423.2 |
| Compound 244 | 5-(2-chloro-6-fluorophenyl)-9-fluoro-8-phenoxy-2,4-dihydrobenzo[d]pyrazolo[3,4-f][1,3]diazepine | HPLC-MS D | 3.56 | 423.2 |
| Compound 245 | 5-(2-chloro-6-fluorophenyl)-8-(cyclopentyloxy)-9-fluoro-2,4-dihydrobenzo[d]pyrazolo[3,4-f][1,3]diazepine | HPLC-MS D | 3.23 | 415.2 |
| Compound 246 | 5-(2-chloro-6-fluorophenyl)-8-(1-ethyl-1H-imidazol-2-yl)-2,4-dihydrobenzo[d]pyrazolo[3,4-f][1,3]diazepine | HPLC-MS D | 1.80 | 407.2 |
| Compound 247 | (S)-8-(sec-butoxy)-5-(2-chloro-6-fluorophenyl)-9-fluoro-2,6-dihydrobenzo[d]pyrazolo[3,4-f][1,3]diazepine | HPLC-MS D | 3.17 | 403.2 |
| Compound 248 | (R)-8-(sec-butoxy)-5-(2-chloro-6-fluorophenyl)-9-fluoro-2,6-dihydrobenzo[d]pyrazolo[3,4-f][1,3]diazepine | HPLC-MS D | 3.17 | 403.2 |

The following Compounds from Table 3 were synthesized with additional steps.

Example 52

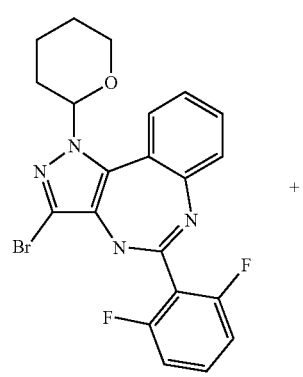

+

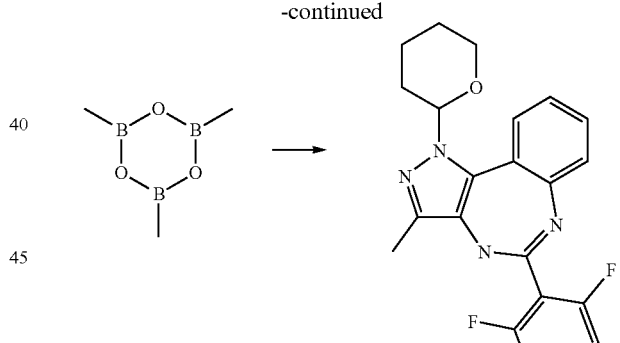

Intermediate 35, 5-(2,6-difluorophenyl)-3-methyl-1-(tetrahydro-2H-pyran-2-yl)-1,4-dihydrobenzo[d]pyrazolo[3,4-f][1,3]diazepine. 3-bromo-5-(2,6-difluorophenyl)-1-(tetrahydro-2H-pyran-2-yl)-1,4-dihydrobenzo[d]pyrazolo[3,4-f][1,3]diazepine, purified by flash chromatography, was dissolved in dioxan. 1 eq. 2,4,6-trimethyl-1,3,5,2,4,6-trioxatriborinane, 2 eq. $Cs_2CO_3$, and 0.2 eq. $Pd(PPh_3)_4$ were added. The mixture was degassed and heated under microwave conditions at 140° C. for 20 min. The mixture was filtered the solids washed with MeOH. After concentration under reduced pressure the mixture was used without further purification. The further step, deprotection, was following the corresponding procedure above.

Example 53

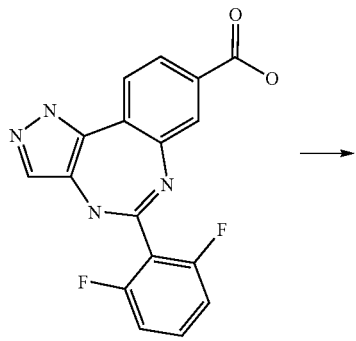

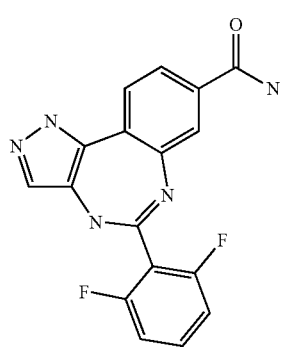

Compound 81, 5-(2,6-difluorophenyl)-1,4-dihydrobenzo[d]pyrazolo[3,4-f][1,3]diazepine-8-carboxamide. 5-(2,6-difluorophenyl)-1,4-dihydrobenzo[d]pyrazolo[3,4-f][1,3]diazepine-8-carboxylic, crude after deprotection, was dissolved in dry DMF. 1.5 eq. EDCI, 1.8 eq. HOBT, 2 eq. NH$_4$Cl, and 6 eq. triethylamine were added and the mixture stirred o.n. at r.t. The mixture was diluted with water, extracted with ethyl acetate. The combined organics were washed with brine, dried over Na$_2$SO$_4$, filtered and concentrated under reduced pressure. The crude product was purified by SEMI-prep chromatography.

Example 54

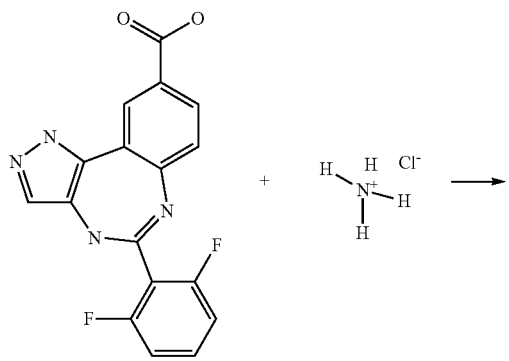

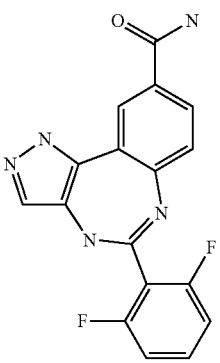

Compound 93, 5-(2,6-difluorophenyl)-1,4-dihydrobenzo[d]pyrazolo[3,4-f][1,3]diazepine-9-carboxamide. 5-(2,6-difluorophenyl)-1,4-dihydrobenzo[d]pyrazolo[3,4-f][1,3]diazepine-9-carboxamide was synthesized according to this procedure using 5-(2,6-difluorophenyl)-1,4-dihydrobenzo[d]pyrazolo[3,4-f][1,3]diazepine-9-carboxylic acid as starting material.

Example 55

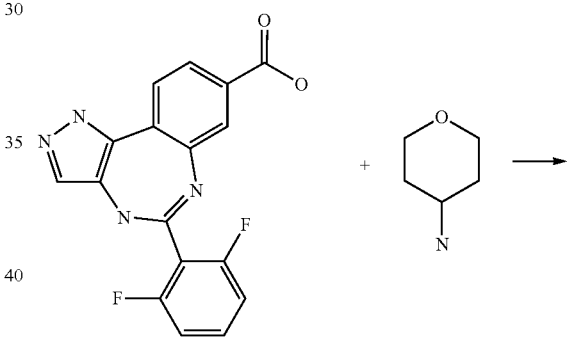

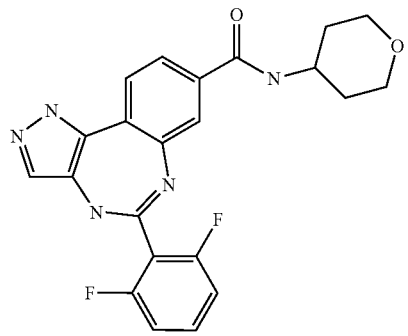

Compound 95, 5-(2,6-difluorophenyl)-N-(tetrahydro-2H-pyran-4-yl)-1,4-dihydrobenzo[d]pyrazolo[3,4-f][1,3]diazepine-8-carboxamide. 5-(2,6-difluorophenyl)-N-(tetrahydro-2H-pyran-4-yl)-1,4-dihydrobenzo[d]pyrazolo[3,4-f][1,3]diazepine-8-carboxamide was synthesized according to this procedure using tetrahydro-2H-pyran-4-amine and 5-(2,6-difluorophenyl)-1,4-dihydrobenzo[d]pyrazolo[3,4-f][1,3]diazepine-8-carboxylic acid as starting material.

Example 56

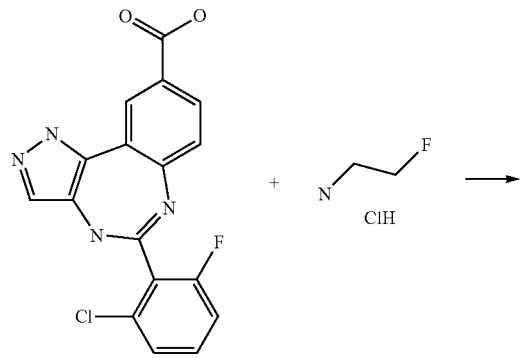

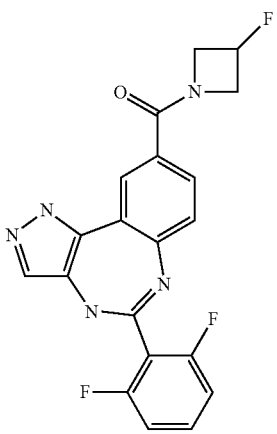

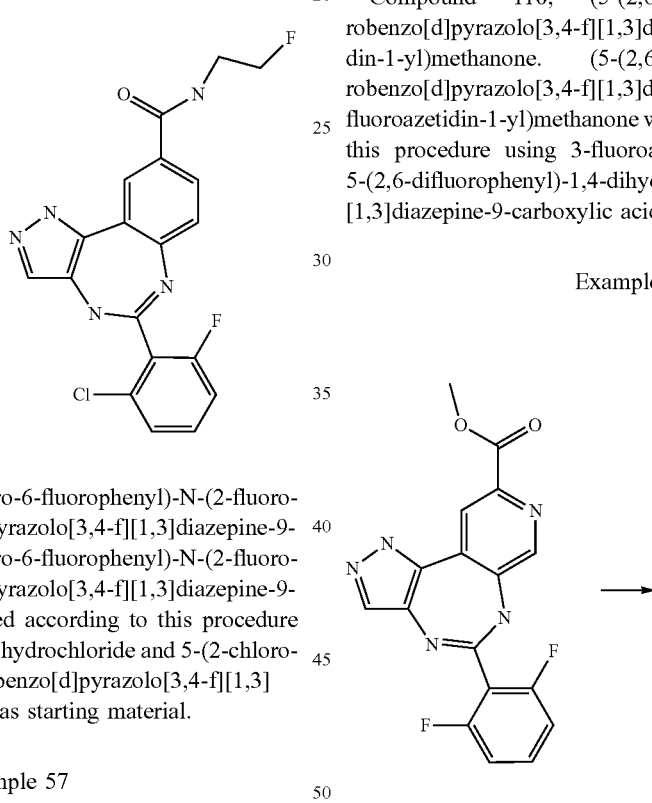

Compound 97, 5-(2-chloro-6-fluorophenyl)-N-(2-fluoroethyl)-1,4-dihydrobenzo[d]pyrazolo[3,4-f][1,3]diazepine-9-carboxamide. 5-(2-chloro-6-fluorophenyl)-N-(2-fluoroethyl)-1,4-dihydrobenzo[d]pyrazolo[3,4-f][1,3]diazepine-9-carboxamide was synthesized according to this procedure using 2-fluoroethan-1-amine hydrochloride and 5-(2-chloro-6-fluorophenyl)-1,4-dihydrobenzo[d]pyrazolo[3,4-f][1,3]diazepine-9-carboxylic acid as starting material.

Compound 110, (5-(2,6-difluorophenyl)-1,4-dihydrobenzo[d]pyrazolo[3,4-f][1,3]diazepin-9-yl)(3-fluoroazetidin-1-yl)methanone. (5-(2,6-difluorophenyl)-1,4-dihydrobenzo[d]pyrazolo[3,4-f][1,3]diazepin-9-yl)(3-fluoroazetidin-1-yl)methanone was synthesized according to this procedure using 3-fluoroazetidin hydrochloride and 5-(2,6-difluorophenyl)-1,4-dihydrobenzo[d]pyrazolo[3,4-f][1,3]diazepine-9-carboxylic acid as starting materials.

Example 57

Example 58

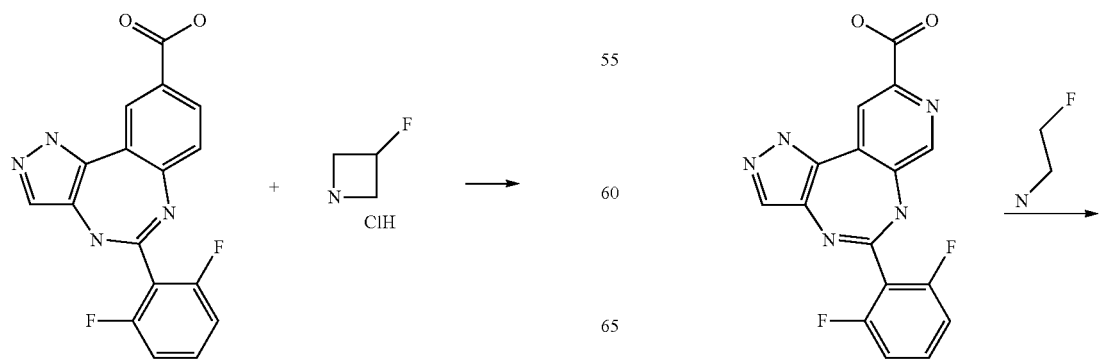

73

-continued

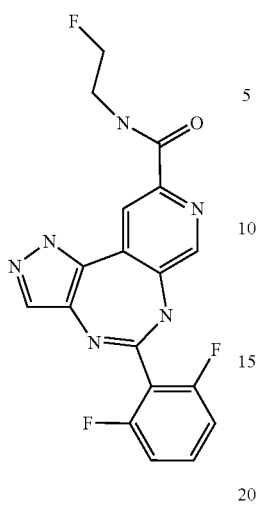

Compound 112

Step 1: 5-(2,6-difluorophenyl)-1,6-dihydropyrazolo[4,3-d]pyrido[4,3-f][1,3]diazepine-9-carboxylic acid. Methyl 5-(2,6-difluorophenyl)-1,6-dihydropyrazolo[4,3-d]pyrido[4,3-f][1,3]diazepine-9-carboxylate was dissolved in THF, sat. aq. LiOH was added and the mixture stirred at 60° C. for 3 h. The mixture was acidified and extracted with ethyl acetate. The combined organics were dried over $Na_2SO_4$, filtered and concentrated under reduced pressure. The product was used without further purification.

Step 2: 5-(2,6-difluorophenyl)-N-(2-fluoroethyl)-1,6-dihydropyrazolo[4,3-d]pyrido[4,3-f][1,3]diazepine-9-carboxamide. 5-(2,6-difluorophenyl)-N-(2-fluoroethyl)-1,6-dihydropyrazolo[4,3-d]pyrido[4,3-f][1,3]diazepine-9-carboxamide was synthesized according to this procedure using 5-(2,6-difluorophenyl)-1,6-dihydropyrazolo[4,3-d]pyrido[4,3-f][1,3]diazepine-9-carboxylic acid and 2-fluoroethan-1-amine as starting material.

Example 59

74

-continued

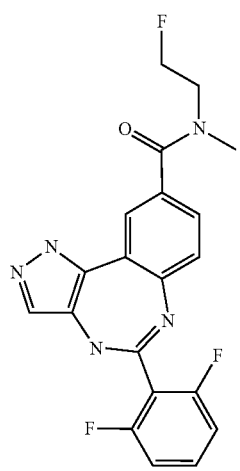

Compound 113, 5-(2,6-difluorophenyl)-N-(2-fluoroethyl)-N-methyl-1,4-dihydrobenzo[d]pyrazolo[3,4-f][1,3]diazepine-9-carboxamide. 5-(2,6-difluorophenyl)-N-(2-fluoroethyl)-N-methyl-1,4-dihydrobenzo[d]pyrazolo[3,4-f][1,3]diazepine-9-carboxamide was synthesized according to this procedure using 5-(2,6-difluorophenyl)-1,4-dihydrobenzo[d]pyrazolo[3,4-f][1,3]diazepine-9-carboxylic acid (2-Fluoro-ethyl)-methyl-amine hydro chloride as starting material.

Example 60

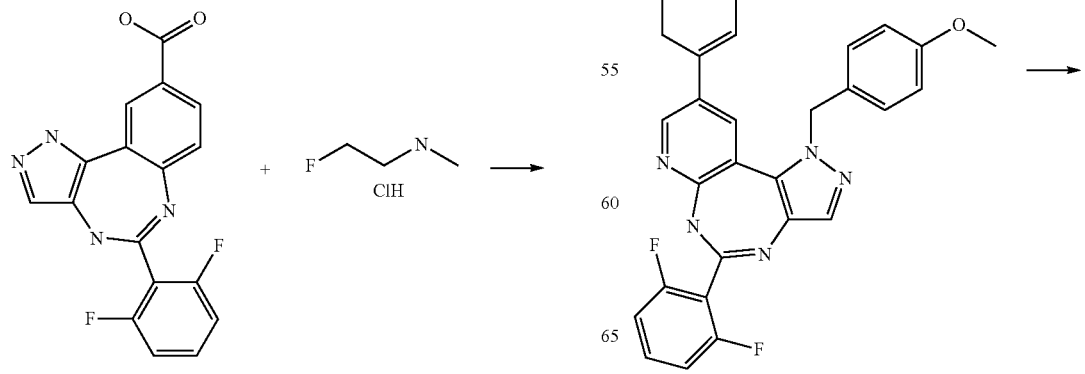

75

-continued

76

-continued

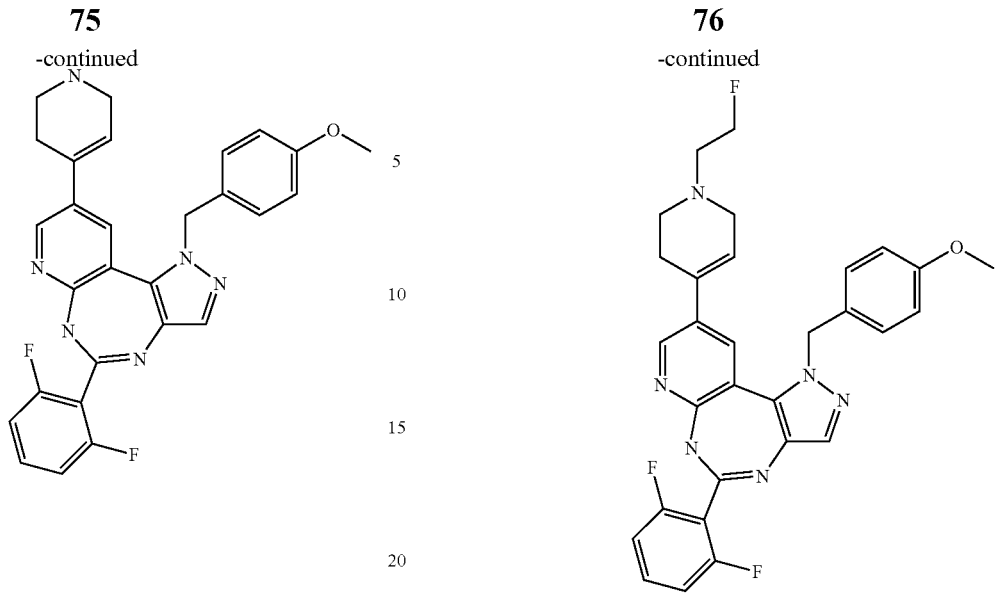

Compound 128

Step 1: 5-(2,6-difluorophenyl)-1-(4-methoxybenzyl)-9-(1,2,3,6-tetrahydropyridin-4-yl)-1,6-dihydropyrazolo[4,3-d]pyrido[3,2-f][1,3]diazepine. Tert-butyl 4-(5-(2,6-difluorophenyl)-1-(4-methoxybenzyl)-1,6-dihydropyrazolo[4,3-d]pyrido[3,2-f][1,3]diazepin-9-yl)-5,6-dihydropyridine-1(2H)-carboxylate was dissolved in 4M HCl in dioxane. The mixture was stirred o.n. at r.t. The solids were collected by filtration and used without further purification.

Step 2: 5-(2,6-difluorophenyl)-9-(1-(2-fluoroethyl)-1,2,3,6-tetrahydropyridin-4-yl)-1-(4-methoxybenzyl)-1,6-dihydropyrazolo[4,3-d]pyrido[3,2-f][1,3]diazepine. 1-bromo-2-fluoroethane and hydrogen chloride and hydrogen chloride and 5-(2,6-difluorophenyl)-1-(4-methoxybenzyl)-9-(1,2,3,6-tetrahydropyridin-4-yl)-1,6-dihydropyrazolo[4,3-d]pyrido[3,2-f][1,3]diazepine was dissolved in dry DMF, 2 eq. 1-bromo-2-fluoroethane and 4 eq. DIPEA were added. The mixture was stirred under microwave conditions for 15 min at 120° C. The heating was repeated after addition of 2 eq. 1-bromo-2-fluoroethane. The mixture was diluted with water and extracted with ethyl acetate. The combined organics were dried over Na$_2$SO$_4$, filtered and concentrated under reduced pressure. The crude product was used without further purification for the deprotection as described above.

Example 61

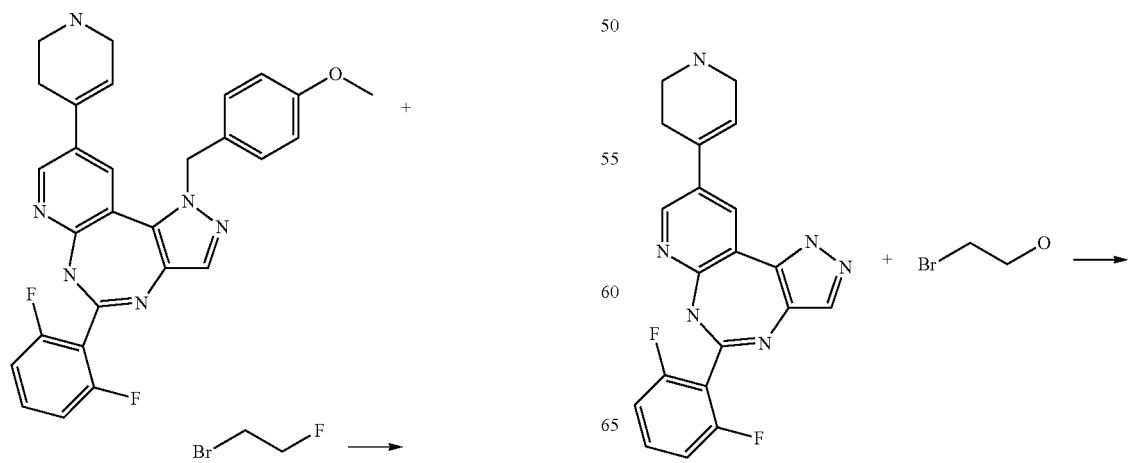

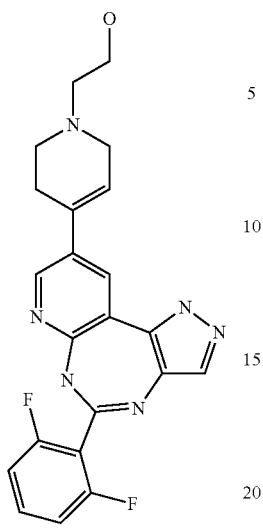

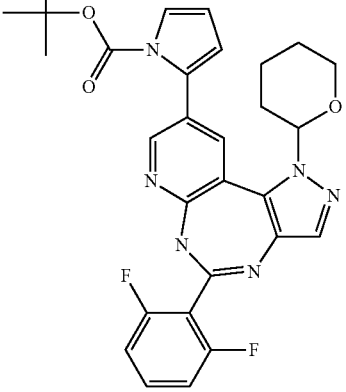

Compound 132, 2-(4-(5-(2,6-difluorophenyl)-1,6-dihydropyrazolo[4,3-d]pyrido[3,2-f][1,3]diazepin-9-yl)-5,6-dihydropyridin-1(2H)-yl)ethan-1-ol. 5-(2,6-difluorophenyl)-9-(1,2,3,6-tetrahydropyridin-4-yl)-1,6-dihydropyrazolo[4,3-d]pyrido[3,2-f][1,3]diazepine was dissolved in dry DMF. 4 eq. DIPEA and 1 eq. 2-bromoethan-1-ol were added. The mixture was stirred at r.t. o.n. Additional 3 eq. DIPEA and 2 eq. 2-bromoethan-1-ol were added and the mixture was stirred o.n. at r.t again. The mixture was concentrated under reduced pressure and purified by flash chromatography.

Example 62

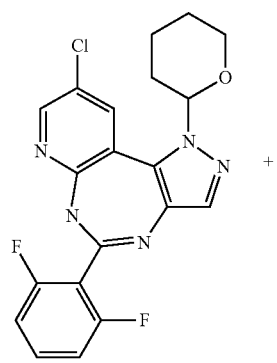
+
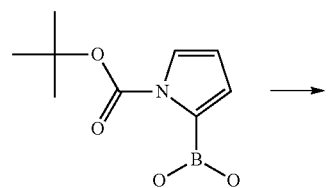

Intermediate 36, tert-butyl 2-(5-(2,6-difluorophenyl)-1-(tetrahydro-2H-pyran-2-yl)-1,6-dihydropyrazolo[4,3-d]pyrido[3,2-f][1,3]diazepin-9-yl)-1H-pyrrole-1-carboxylate. 9-chloro-5-(2,6-difluorophenyl)-1-(tetrahydro-2H-pyran-2-yl)-1,6-dihydropyrazolo[4,3-d]pyrido[3,2-f][1,3]diazepine was dissolved in dioxane. 1.5 eq. (1-(tert-butoxycarbonyl)-1H-pyrrol-2-yl)boronic acid, 12 eq. 2M Na$_2$CO$_3$ solution were added. The mixture was degassed with N$_2$ before adding 0.2 eq. Pd dppf. The mixture was heated at 140° C. for 30 min under microwave conditions. Additional 1.5 eq. (1-(tert-butoxycarbonyl)-1H-pyrrol-2-yl)boronic acid and 0.2 eq. Pd dppf 0.2 eq were added and the mixture heated again for 30 min at 140° C. und der microwave conditions. This addition and heating were repeated twice. The mixture was filtered through celite and then concentrated under reduced pressure. The next step, the deprotection, was carried under the conditions above.

Example 63

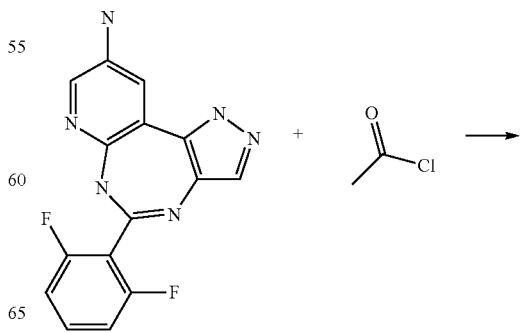

-continued

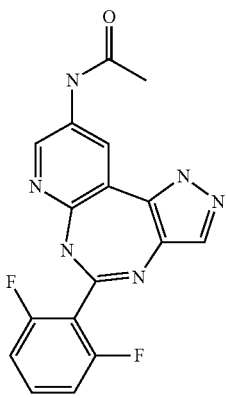

Compound 90, N-(5-(2,6-difluorophenyl)-1,6-dihydropyrazolo[4,3-d]pyrido[3,2-f][1,3]diazepin-9-yl)acetamide and N-(1-acetyl-5-(2,6-difluorophenyl)-1,6-dihydropyrazolo[4,3-d]pyrido[3,2-f][1,3]diazepin-9-yl)acetamide. 5-(2,6-difluorophenyl)-1,6-dihydropyrazolo[4,3-d]pyrido[3,2-f][1,3]diazepin-9-amine was dissolved in DCM, 4 eq. acetyl chloride and 2 eq. triethylamine were added. The mixture was stirred o.n. at r.t. The mixture was diluted with methanol and NaHCO$_3$, saturated aq. solution, then basified with NaOH solid and stirred at 40° C. for 12 h. The mixture was neutralized with 2M HCl and then concentrated under reduced pressure and purified by SEMIprep chromatography.

Example 64

The compounds in Table 3 were tested for their inhibitory effect on a set of kinases according to the following procedures.
Biochemical Assays:

The basic protocol for TR-FRET LanthaScreen Eu Kinase Binding Assay inhibitor studies were performed as follows. LanthaScreen Kinase Binding Assays (ThermoFisher/USA) to evaluate inhibitors were performed by addition of 5 µl of test compound in corresponding DMSO dilutions/5 µl of kinase/antibody mixture, 5 µl of tracer into 384 well small volume plates. After incubation for 1 hour at room temperature, plates were read. Data analysis of emission ratios was according to LanthaScreen Eu Kinase Binding Assay protocol.

Kinase and assay components were adjusted to final concentrations according to the kit protocol. For LRRK2: 5 nM wt human LRRK2, catalytic site, or G2019S human LRRK2, catalytic site (ThermoFisher/USA), 2 nM Eu-Anti-GST Antibody, 10 nM Kinase Tracer 236 in 1× Kinase Buffer A. For NUAK1: 8 nM wt human NUAK1, full length (ThermoFisher/USA), 2 nM Eu-Anti-His Antibody, 5 nM Kinase Tracer 236 in 1× Kinase Buffer A.

Basic protocol for HTRF KinEASE assay (Cisbio/FRA) inhibitor studies involved two steps:

Enzymatic step: Addition of 4 µl of test compound in corresponding DMSO dilutions, 4 µl of kinase/substrate mixture, 2 µl of ATP into 384 well small volume plates. Incubation for at least 30 minutes at room temperature.

Detection step: Addition of 5 µl antibody and 5 µl streptavidin-XL665, read plate after 60 minutes. Data analysis of emission ratios according to KinEASE assay protocol.

Kinase and assay components were adjusted to final concentrations according to the kit protocol. For TYK2: 2 nM wt human TYK2, catalytic site (SignalChem/CAN), 1 µM HTRF KinEASE-TK Substrate-biotin, 1 µM ATP in 1× Kinase Buffer Results for from biochemical tests were as follows:
Inhibitory Activity Toward LRRK2 (Wt) and LRRK2 (G2019)

The following compounds had an IC$_{50}$ lower than 10 nM: Compound 93; Compound 200; Compound 248; Compound 143; Compound 247; Compound 35; Compound 183; Compound 135; Compound 97; Compound 101; Compound 67; Compound 187; Compound 36; Compound 117; Compound 94; Compound 202; Compound 103; Compound 138; Compound 171; Compound 147; Compound 211; Compound 95; Compound 162; Compound 71; Compound 207; Compound 81; Compound 201; Compound 197; Compound 225; Compound 141; Compound 69; Compound 73; Compound 166; Compound 64; Compound 61; Compound 226; Compound 88; Compound 167; Compound 152; Compound 50; Compound 76; Compound 190; Compound 25; Compound 102; Compound 165; Compound 72; Compound 220; Compound 182; Compound 128; Compound 168; Compound 161; Compound 184; Compound 53; Compound 120; Compound 209; Compound 231; Compound 49; Compound 188; Compound 127; Compound 196; Compound 178; Compound 169; Compound 79; Compound 149; Compound 151; Compound 45; Compound 133; Compound 115; Compound 44; Compound 157; Compound 210; Compound 126; Compound 156; Compound 125; Compound 33; Compound 51; Compound 164; Compound 40; Compound 140; Compound 78; Compound 195; Compound 242; Compound 27; Compound 132; Compound 47; Compound 237; Compound 173; Compound 218; Compound 145; Compound 180; Compound 46; Compound 42; Compound 38; Compound 158; Compound 86; Compound 77; Compound 216; Compound 206; Compound 236; Compound 68; Compound 217; Compound 43; Compound 139; Compound 90; Compound 41; Compound 239; Compound 194; Compound 238; Compound 34; Compound 112; Compound 175; Compound 63; Compound 18; Compound 98; Compound 136; Compound 146; Compound 8; Compound 172; Compound 176; Compound 179; Compound 205; Compound 241; Compound 240; Compound 222; Compound 87; Compound 204; Compound 123; Compound 191; Compound 52; Compound 192; Compound 163; Compound 159; Compound 212; Compound 39; Compound 215; Compound 223; Compound 228; Compound 37; Compound 186; and Compound 198.

The following compounds had an IC$_{50}$ between 10 nM and 100 nM: Compound 234; Compound 150; Compound 124; Compound 32; Compound 99; Compound 160; Compound 219; Compound 177; Compound 185; Compound 221; Compound 131; Compound 189; Compound 105; Compound 110; Compound 100; Compound 130; Compound 137; Compound 230; Compound 232; Compound 233; Compound 208; Compound 235; Compound 203; Compound 243; Compound 245; Compound 11; Compound 199; Compound 30; Compound 214; Compound 148; Compound 13; Compound 244; Compound 193; Compound 229; Compound 224; Compound 113; Compound 107; Compound 170; Compound 142; Compound 213; Compound 181; Compound 111; Compound 122; Compound 31; Compound 129; Compound 82; Compound 155; Compound 14; Compound 84; Compound 29; Compound 104; Compound 83; Compound 227; and Compound 66.

The following compounds had an $IC_{50}$ between 100 nM and 1000 nM: Compound 56; Compound 108; Compound 114; Compound 75; Compound 144; Compound 119; Compound 59; Compound 57; Compound 118; Compound 48; Compound 60; Compound 62; Compound 1; Compound 134; Compound 174; Compound 106; Compound 3; Compound 21; Compound 89; Compound 24; Compound 17; Compound 91; Compound 92; Compound 80; Compound 116; Compound 12; and Compound 9.

Inhibitory Activity Toward TYK2

The following compounds had an $IC_{50}$ lower than 10 nM: Compound 73; Compound 242; Compound 226; Compound 229; Compound 95; Compound 230; Compound 162; Compound 222; Compound 241; Compound 157; Compound 236; Compound 81; Compound 228; and Compound 221.

The following compounds had an $IC_{50}$ between 10 nM and 100 nM: Compound 225; Compound 156; Compound 247; Compound 231; Compound 216; Compound 72; Compound 237; Compound 160; Compound 88; Compound 239; Compound 155; Compound 105; Compound 220; Compound 227; Compound 243; Compound 159; Compound 198; Compound 211; Compound 235; Compound 71; Compound 224; Compound 49; Compound 52; Compound 197; Compound 248; Compound 232; Compound 238; Compound 245; Compound 223; Compound 240; Compound 98; Compound 69; Compound 218; Compound 127; Compound 34; Compound 164; Compound 135; Compound 158; Compound 99; Compound 200; Compound 76; Compound 190; Compound 27; Compound 171; Compound 219; Compound 68; Compound 8; Compound 66; Compound 30; Compound 147; Compound 169; Compound 33; Compound 201; Compound 210; Compound 53; Compound 234; Compound 233; Compound 202; and Compound 89.

The following compounds had an $IC_{50}$ between 100 nM and 1000 nM: Compound 42; Compound 11; Compound 90; Compound 64; Compound 43; Compound 143; Compound 152; Compound 111; Compound 35; Compound 25; Compound 39; Compound 32; Compound 79; Compound 61; Compound 165; Compound 78; Compound 37; Compound 203; Compound 119; Compound 18; Compound 161; Compound 215; Compound 36; Compound 94; Compound 114; Compound 50; Compound 125; Compound 103; Compound 107; Compound 150; Compound 108; Compound 146; Compound 194; Compound 93; Compound 199; Compound 183; Compound 172; Compound 163; Compound 184; Compound 166; Compound 244; Compound 217; Compound 186; Compound 38; Compound 56; Compound 182; Compound 45; Compound 115; Compound 170; Compound 138; Compound 126; Compound 214; Compound 106; Compound 60; and Compound 168.

Inhibitory Activity Toward NUAK1

The following compounds had an $IC_{50}$ lower than 10 nM: Compound 71; Compound 165; Compound 234; Compound 237; and Compound 226

The following compounds had an $IC_{50}$ between 10 nM and 100 nM: Compound 72; Compound 36; Compound 143; Compound 53; Compound 225; Compound 171; Compound 155; Compound 164; Compound 233; Compound 127; Compound 35; Compound 135; Compound 168; Compound 126; Compound 175; Compound 231; Compound 241; Compound 211; Compound 160; Compound 228; Compound 68; Compound 218; Compound 166; Compound 69; Compound 73; Compound 125; Compound 202; Compound 115; Compound 44; Compound 76; Compound 216; Compound 235; Compound 99; Compound 42; Compound 183; Compound 27; Compound 93; Compound 158; Compound 215; Compound 162; Compound 230; Compound 194; Compound 200; Compound 147; Compound 88; Compound 207; Compound 103; Compound 238; Compound 61; Compound 159; Compound 180; Compound 186; Compound 182; Compound 34; Compound 33; Compound 184; Compound 25; Compound 64; Compound 173; Compound 138; Compound 203; Compound 197; Compound 95; Compound 98; Compound 179; Compound 240; Compound 169; Compound 210; Compound 247; Compound 94; Compound 161; Compound 209; Compound 43; Compound 178; Compound 46; Compound 190; Compound 50; Compound 11; and Compound 242

The following compounds had an $IC_{50}$ between 100 nM and 1000 nM: Compound 150; Compound 32; Compound 188; Compound 201; Compound 167; Compound 8; Compound 105; Compound 78; Compound 204; Compound 157; Compound 37; Compound 219; Compound 146; Compound 221; Compound 177; Compound 217; Compound 18; Compound 172; Compound 220; Compound 208; Compound 163; Compound 214; Compound 206; Compound 176; Compound 45; Compound 152; Compound 156; Compound 100; Compound 87; Compound 51; Compound 151; Compound 243; Compound 39; Compound 40; Compound 212; Compound 47; Compound 59; Compound 222; Compound 229; Compound 198; Compound 239; Compound 49; Compound 38; Compound 145; Compound 102; Compound 236; Compound 90; Compound 245; Compound 185; Compound 41; Compound 223; Compound 136; Compound 227; Compound 137; Compound 114; Compound 140; and Compound 205.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A compound of formula (I) below:

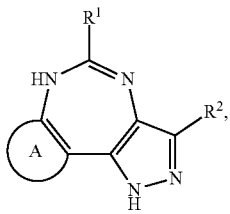

(I)

or a tautomer thereof, or a pharmaceutically acceptable salt thereof,
wherein:
$R^1$ is aryl or heteroaryl, each of which is optionally substituted;
$R^2$ is H, halo, OH, CN, $CF_3$, $C_{1-6}$ alkyl, $C_{1-6}$ alkoxy, $C_{1-6}$ haloalkyl, $C_{1-6}$ thioalkyl, $C_{3-8}$ cycloalkyl, $C_{2-8}$ heterocycloalkyl, aryl, or heteroaryl; and
A is aryl or 5- or 6-membered heteroaryl;
wherein each of the $C_{1-6}$ alkyl, $C_{1-6}$ alkoxy, $C_{1-6}$ haloalkyl, $C_{1-6}$ thioalkyl, $C_{3-8}$ cycloalkyl, $C_{2-8}$ heterocycloalkyl, aryl, and heteroaryl is optionally substituted with one or more moieties selected from the group consisting of halo, OH, CN, $CF_3$, $NH_2$, $NO_2$, $C_{1-6}$ alkyl, $C_{1-6}$ haloalkyl, $C_{1-6}$ thioalkyl, $C_{3-8}$ cycloalkyl, $C_{2-8}$ heterocycloalkyl, $C_{2-8}$ heterocycloalkenyl, $C_{2-6}$ alkenyl, $C_{2-6}$ alkynyl, $C_{1-6}$ alkoxy, $C_{1-6}$ haloalkoxy, $C_{1-6}$ alkylamino, $C_{2-6}$ dialkylamino, $C_{7-12}$ aralkyl, $C_{1-12}$ heteroaralkyl, aryl, heteroaryl, —C(O)R, —C(O)OR, —C(O)NRR', —C(O)NRS(O)$_2$R', —C(O)NRS(O)$_2$NR'R", —OR, —OC(O)NRR', —NRR', —NRC(O)R', —NRC(O)NR'R", —NRS(O)$_2$R', —NRS(O)$_2$NR'R", —S(O)$_2$R, and —S(O)$_2$NRR',
in which each of R, R', and R", independently, is H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, aryl, or heteroaryl, or R and R', or R' and R", together with the nitrogen to which they are attached, form $C_{2-8}$ heterocycloalkyl.

2. The compound of claim 1, having formula (II) shown below:

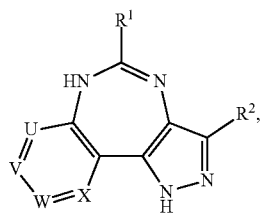

(II)

wherein
$R^1$ is aryl or heteroaryl, each of which is optionally substituted;
$R^2$ is H, halo, OH, CN, $CF_3$, $C_{1-6}$ alkyl, $C_{1-6}$ alkoxy, $C_{1-6}$ haloalkyl, $C_{1-6}$ thioalkyl, or $C_{3-8}$ cycloalkyl;
U is N or $CR_3$;
V is N or $CR_4$;
W is N or $CR_5$;
X is N or $CR_6$; and
each of $R^3$—$R^6$, independently, is H, halo, OH, CN, $CF_3$, $CHF_2$, $CH_2F$, $NH_2$, $NO_2$, $C_{1-6}$ alkyl, $C_{1-6}$ haloalkyl, $C_{2-6}$ alkenyl, $C_{3-8}$ cycloalkyl, $C_{2-8}$ heterocycloalkyl, $C_{2-8}$ heterocycloalkenyl, aryl, heteroaryl, —C(O)R, —C(O)OR, —C(O)NRR', —C(O)NRS(O)$_2$R', —C(O)NRS(O)$_2$NR'R", —OR, —OC(O)NRR', —NRR', —NRC(O)R', —NRC(O)NR'R", —NRS(O)$_2$R', —NRS(O)$_2$NR'R", —S(O)$_2$R, or —S(O)$_2$NRR',
wherein
each of R, R', and R", independently, is H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, aryl, or heteroaryl, or
R and R', or R' and R", together with the nitrogen to which they are attached, form $C_{2-8}$ heterocycloalkyl; and
at most one N is assigned to U, V, W, and X.

3. The compound of claim 2, having formula (III) shown below:

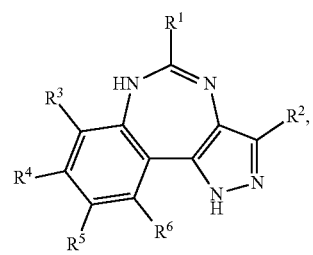

(III)

wherein
$R^1$ is aryl or heteroaryl, each of which is optionally substituted;
$R^2$ is H, halo, OH, CN, $CF_3$, $CHF_2$, $CH_2F$, $C_{1-6}$ alkyl, $C_{1-6}$ alkoxy, $C_{1-6}$ haloalkyl, $C_{1-6}$ thioalkyl, or $C_{3-8}$ cycloalkyl; and
each of $R^3$—$R^6$, independently, is H, halo, OH, CN, $CF_3$, $CHF_2$, $CH_2F$, $NH_2$, $NO_2$, $C_{1-6}$ alkyl, $C_{1-6}$ haloalkyl, $C_{2-6}$ alkenyl, $C_{3-8}$ cycloalkyl, $C_{2-8}$ heterocycloalkyl, $C_{2-8}$ heterocycloalkenyl, aryl, heteroaryl, —C(O)R, —C(O)OR, —C(O)NRR', —C(O)NRS(O)$_2$R', —C(O)NRS(O)$_2$NR'R", —OR, —OC(O)NRR', —NRR', —NRC(O)R', —NRC(O)NR'R", —NRS(O)$_2$R', —NRS(O),NR'R", —S(O)$_2$R, or —S(O)$_2$NRR', or $R^4$ and $R^5$, together with atoms to which they are attached form a ring having between 5 and 10 members,
wherein
each of R, R', and R", independently, is H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, aryl, or heteroaryl, or R and R', or R' and R", together with the nitrogen to which they are attached, form $C_{2-8}$ heterocycloalkyl.

4. The compound of claim 2, wherein one of U, V, W, and X is N.

5. The compound of claim 2, wherein $R^1$ is aryl.

6. The compound of claim 2, wherein $R^1$ is 5- or 6-membered heteroaryl.

7. The compound of claim 2, wherein $R^2$ is H, halo, $C_{1-6}$ alkyl, $C_{1-6}$ alkoxy, $C_{1-6}$ thioalkyl, or $C_{3-8}$ cycloalkyl.

8. The compound of claim 3, wherein each of $R^3$—$R^6$, independently, is H, halo, OH, CN, $CF_3$, $CHF_2$, $CH_2F$, $NH_2$, $NO_2$, $C_{1-6}$ alkyl, $C_{3-8}$ cycloalkyl, $C_{2-8}$ heterocycloalkyl, $C_{2-8}$ heterocycloalkenyl, aryl, heteroaryl, —C(O)OR, —C(O)NRR', —OR, —OC(O)NRR', —NRR', or —NRC(O)R'.

9. The compound of claim 3, wherein at least three of $R^3$—$R^6$ are each H.

10. The compound of claim 3, wherein each of $R^3$, $R^4$, and $R^6$ is H.

11. The compound of claim 3, wherein each of $R^3$—$R^6$ is H.

12. The compound of claim 3, wherein each of $R^3$ and $R^6$ is H.

13. The compound of claim 3, wherein each of $R^3$ and $R^6$ is H, and each of $R^4$ and $R^5$, independently, is halo, OH, CN, $CF_3$, $CHF_2$, $CH_2F$, $NH_2$, $NO_2$, $C_{1-6}$ alkyl, $C_{3-8}$ cycloalkyl, $C_{2-8}$ heterocycloalkyl, $C_{2-8}$ heterocycloalkenyl, aryl, heteroaryl, —C(O)OR, —C(O)NRR', —OR, —OC(O)NRR', —NRR', or —NRC(O)R'.

14. The compound of claim 3, wherein each of $R^3$, $R^4$, and $R^6$ is H, and $R^5$ is halo, OH, CN, $CF_3$, $NH_2$, $NO_2$, $C_{1-6}$ alkyl, $C_{3-8}$ cycloalkyl, $C_{2-8}$ heterocycloalkyl, $C_{2-8}$ heterocycloalkenyl, aryl, heteroaryl, —C(O)OR, —C(O)NRR', —OR, —OC(O)NRR', —NRR', or —NRC(O)R'.

15. The compound of claim 8, wherein each of $R^3$—$R^6$, independently, is H, halo, $CF_3$, $C_{1-6}$ alkyl, $C_{2-8}$ heterocycloalkyl, $C_{2-8}$ heterocycloalkenyl, OR, —C(O)OR, or —C(O)NRR'.

16. The compound of claim 8, wherein each of $R^3$ and $R^6$ is H, and each of $R^4$ and $R^5$, independently, is halo, $CF_3$, $CHF_2$, $CH_2F$, $C_{1-6}$ alkyl, $C_{2-8}$ heterocycloalkyl, $C_{2-8}$ heterocycloalkenyl, —OR, —C(O)OR, or —C(O)NRR'.

17. The compound of claim 16, wherein each of $R^4$ and $R^5$, independently, is F, $C_1$, $CF_3$, $CHF_2$, $CH_2F$, $C_{1-6}$ alkyl, $C_{2-8}$ heterocycloalkyl, $C_{2-8}$ heterocycloalkenyl, —OR, —C(O)OR, or —C(O)NRR', in which each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

18. The compound of claim 8, wherein each of $R^3$, $R^4$, and $R^6$ is H, and $R^5$ is halo, $CF_3$, $CHF_2$, $CH_2F$, $C_{1-6}$ alkyl, $C_{2-8}$ heterocycloalkyl, $C_{2-8}$ heterocycloalkenyl, —OR, —C(O)OR, or —C(O)NRR'.

19. The compound of claim 18, wherein $R^5$ is F, Cl, $CF_3$, $CHF_2$, $CH_2F$, $C_{1-6}$ alkyl, $C_{2-8}$ heterocycloalkyl, $C_{2-8}$ heterocycloalkenyl, —OR, —C(O)OR, or —C(O)NRR', in which each of R and R', independently, is H, $C_{1-6}$ alkyl, $C_{1-6}$ haloalkyl, $C_{3-8}$ cycloalkyl, or $C_{2-8}$ heterocycloalkyl, or R and R', together with the nitrogen to which they are attached, form $C_{2-8}$ heterocycloalkyl.

20. The compound of claim 4, wherein U is N.

* * * * *